US009670473B2

(12) United States Patent
Acharya et al.

(10) Patent No.: US 9,670,473 B2
(45) **Date of Patent: *Jun. 6, 2017**

(54) CRYSTALS OF ANGIOTENSIN-CONVERTING ENZYME (ACE)

(71) Applicant: ANGIODESIGN (UK) LTD., Wiltshire (GB)

(72) Inventors: Ravi Acharya, Bath (GB); Edward Sturrock, Cape Town (ZA)

(73) Assignee: Angiodesign (UK) Limited, Wiltshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/228,108

(22) Filed: Aug. 4, 2016

(65) Prior Publication Data

US 2016/0333334 A1 Nov. 17, 2016

Related U.S. Application Data

(63) Continuation of application No. 14/297,500, filed on Jun. 5, 2014, now Pat. No. 9,434,933, which is a continuation of application No. 12/160,562, filed as application No. PCT/GB2007/000064 on Jan. 10, 2017, now Pat. No. 8,796,006.

(30) Foreign Application Priority Data

Jan. 10, 2006 (GB) .................................. 0600406.3

(51) Int. Cl.

| | |
|---|---|
| ***C12N 9/48*** | (2006.01) |
| ***C07K 14/70*** | (2006.01) |
| ***A61K 38/48*** | (2006.01) |
| ***C12Q 1/37*** | (2006.01) |
| ***C07K 14/705*** | (2006.01) |
| *A61K 38/00* | (2006.01) |

(52) U.S. Cl.

CPC .......... *C12N 9/485* (2013.01); *A61K 38/4813* (2013.01); *C07K 14/70596* (2013.01); *C12N 9/48* (2013.01); *C12Q 1/37* (2013.01); *C12Y 304/15001* (2013.01); *A61K 38/00* (2013.01); *C07K 2299/00* (2013.01)

(58) Field of Classification Search

None

See application file for complete search history.

(56) References Cited

U.S. PATENT DOCUMENTS

| | | | |
|---|---|---|---|
| 3,832,337 | A | 8/1974 | Ondetti et al. |
| 3,891,616 | A | 6/1975 | Ondetti |
| 3,947,575 | A | 3/1976 | Ondetti |
| 4,052,511 | A | 10/1977 | Cushman et al. |
| 4,053,651 | A | 10/1977 | Ondetti et al. |
| 7,704,319 | B2 | 4/2010 | Acharya et al. |
| 2004/0033532 | A1 | 2/2004 | Ehlers et al. |
| 2006/0174816 | A1 | 8/2006 | Acharya et al. |

FOREIGN PATENT DOCUMENTS

| | | | |
|---|---|---|---|
| EP | 0096430 | A1 | 12/1983 |
| EP | 0134048 | A1 | 3/1985 |
| EP | 0184438 | A2 | 6/1986 |
| EP | 0253455 | A1 | 1/1988 |
| EP | 0301670 | A1 | 2/1989 |
| EP | 0444605 | A2 | 9/1991 |
| WO | WO-86/06097 | A1 | 10/1986 |
| WO | WO-91/00354 | A1 | 1/1991 |
| WO | WO-91/11172 | A1 | 8/1991 |
| WO | WO-94/02518 | A1 | 2/1994 |
| WO | WO-98/55148 | A1 | 12/1998 |
| WO | WO-2004/024765 | A1 | 3/2004 |

OTHER PUBLICATIONS

Guy et al., Angiotensin-converting enzyme-2 (ACE2): Comparative modeling of the active site, specificity requirements, and chloride dependence. *Biochemistry*, 42: 13185-92 (2003).

Abrahams et al., Methods used in the structure determination of bovine mitochondrial F1 ATPase, *Acta Crystallogr*. 52: 30-42 (1996).

Aghahari et al., Structural basis of alpha-amylase activation by chloride, *Protein Sci*. 11: 1435-41 (2002).

Altschul et al., Basic local alignment search tool, *J. Mol. Biol*. 215: 403-10 (1990).

Andújar-Sánchez et al., A calorimetric study of the binding of lisinopril, enalaprilat and captopril to angiotensin-converting enzyme, *Biophys. Chem*. 111: 183-9 (2004).

Ausubel et al, Short Protocols in Molecular Biology, 4th edition, p. 7-58 to 7-60, chapter 18 (1999).

Azizi et al., Acute angiotensin-converting enzyme inhibition increases the plasma level of the natural stem cell regulator N-acetyl-serly-aspartyl-lysyl-proline, *J. Clin. Invest*. 97: 839-44 (1996).

Balyasnikova et al, Localization of an N-domain region of angiotensin-converting enzyme involved in the regulation of ectodomain shedding using monoclonal antibodies, *J. Proteome Res*. 4: 258-67 (2005).

Bartlett et al., CAVEAT: A program to facilitate the structure-derived design of biologically active molecules, in Molecular Recognition: Chemical and Biological Problems, Roberts D. M. (ed), Royal Society of Chemistry, London, special publication No. 78:182-196 (1989).

Beldent et al., Proteolytic release of human angiotensin-converting enzyme. Localization of the cleavage site, *J. Parh. Sci*. 66 (1):1-19 (1977).

Beldent et al., Proteolytic release of human angiotensin-converting enzyme. Localization of the cleavage site. *J. Biol. Chem*. 268: 26428-34 (1993).

(Continued)

*Primary Examiner* — Suzanne M Noakes

(74) *Attorney, Agent, or Firm* — Marshall, Gerstein & Borun LLP

(57) ABSTRACT

The present invention relates to a crystal. In particular the present invention relates to a crystal of the N-domain of ACE protein. The present invention also relates to methods, processes, domain specific modulators, pharmaceutical compositions and uses of the N-domain crystal and the structure co-ordinates thereof.

11 Claims, 4 Drawing Sheets

(56) References Cited

OTHER PUBLICATIONS

Berge et al., Pharmaceutical salts, *J. Pharm. Sci*. 66(1): 1-19 (1977).
Binevski et al., Evidence for the negative cooperativity of the two active sites within bovine somatic angiotensin-converting enzyme, *FEBS Lett*. 550: 84-8 (2003).
Bohm, The computer program LUDI: a new method for the de novo design of enzyme inhibitors, *J. Comput. Aided Mol. Des*. 6: 61-78 (1992).
Brenner et al., Diverse biological actions of atrial natriuretic peptide. *Physiol Rev*. 70(3): 665-99 (1990).
Brown et al., Black Americans have an increased rate of angiotensin converting enzyme inhibitor-associated angioedema, *Clin. Pharmacol. Ther*. 60: 8-13(1996).
Brown et al., Structure of neurolysin reveals a deep channel that limits substrate access, *Proc. Natl. Acad. Sci. USA*, 98: 3127-32 (2001).
Brunger et al., Crystallography & NMR system: A new software suite for macromolecular structure determination, *Acta Crystallogr. D. Biol. Crystallogr*. 54: 905-21 (1998).
Brunger, Free R value: a novel statistical quantity for assessing the accuracy of crystal structures, *Nature*, 355: 472-5 (1992).
Bunning et al., Activation of angiotensin converting enzyme by monovalent anions, *Biochemistry*, 22: 110-16 (1983).
Chubb et al., Defining the boundaries for the testis angiotensin I-converting enzyme ectodomain, *Biochem. Biophys. Res. Commun*. 297: 1225-30 (2002).
Cohen et al, Molecular modeling software and methods for medicinal chemistry, *J. Med. Chem*. 33 (3): 883-94 (1990).
Collaborative Computational project . No. 4, The CCP4 Suite: Programs for Protein Crystallography, Acta Crystallogr. D. Biol. Crystallogr. 50:760-63 (1994).
Combined International Search Repost and Written Opinion, PCT/GB2007/000064, European Patent Office, Sep. 3, 2007.
Corradi et al., Crystal structure of the N domain of human somatic angiotensin I-converting enzyme provides a structural basis for domain-specific inhibitor design, *J. Mol. Biol*. 357: 964-74 (2006).
Corvol et al., Peptigyl dipeptidase A: Angiotension I-converting enzyme, *Methods Enzymol*. 248: 283-305 (1995).
Couvineau et al., Mutagenesis of N-glycosylation sites in the human vasoactive intestinal peptide 1 receptor. Evidence that asparagine 58 or 69 is crucial for correct delivery of the receptor to plasma membrane, *Biochemistry*, 35: 1745-52 (1996).
Cushman et al., Design of potent competitive inhibitors of angiotensin-converting enzyme carboxyalkanoyl and mercaptoalkanoyl amino acids, *Biochemistry*, 16(25): 5484-91 (1977).
Danilov et al., Structure-function analysis of angiotensin I-converting enzyme using monoclonal antibodies, *J. Biol. Chem*. 269: 26806-14 (1994).
Davis et al., Ligand binding by the immunoglobulin superfamily recognition molecule CD2 is glycosylation-independent, *J. Biol. Chem*. 270: 369-75 (1995).
de La Fortelle et al., Maximum-likelihood heavy-atom parameter refinement for multiple isomorphous replacement and multiwavelength anomalous defection methods, *Methods Enzymol*. 276: 472-94 (1997).
Declaration of Edward David Sturrock under 37 C.F.R. §1.132 submitted in connection with U.S. Appl. No. 12/160,562, dated Mar. 3, 2014.
Deddish et al., Differences in the hydrolysis of enkephalin congeners by the two domains of angiotensin converting enzyme, *Biochem. Pharmacol*. 53(10): 1459-63 (1997).
Deddish et al., N-domain-specific substrate and C-domain inhibitors of angiotensin-converting enzyme angiotensin-(1-7) and keto-ACE, *Hypertension*, 31: 912-7 (1998).
Devereux et al., A comprehensive set of sequence analysis programs for the VAX, *Nucl. Acids Res*. 12: 387-95 (1984).
Dive et al., RXP407, a phosphinic peptide, is a potent inhibitor of angiotensin I converting enzyme able to differentiate between its two active sites, *Proc. Natl. Acad. Sci. USA*, 96: 4330-5 (1999).
Ehlers et al., Angiotensin-converting enzyme: Zinc- and inhibitor-binding stoichimetrics of the somatic and testis enzymes, *Biochemistry*, 30: 7118-25 (1991).
Ehlers et al., Molecular cloning of human testicular angiotension-converting enzyme: the testis isozyme is identical to the C-terminal half of endothelial angiotensin-converting enzyme, *Proc. Natl. Acad. Sci. USA*, 86: 7741-5 (1989).
Ehlers et al., Proteolytic release of membrane-bound angiotensin-converting enzyme: role of the juxtamembrane stalk sequence, *Biochemistry*, 35: 9549-59 (1996).
Ehlers et al., Spontaneous solubilization of membrane-bound human testis angiotensin-converting enzyme expressed in Chinese hamster ovary cells, *Proc. Natl. Acad. Sci. USA*, 88: 1009-13 (1991).
Ehlers et al., The unique N-terminal sequence of testis angiotensin-converting enzyme is heavily O-glycosylated and unessential for activity or stability, *Biochm. Biophys. Res. Commun*. 183: 199-205 (1992).
Emsley P. et al., COOT—Model building tools for molecular graphics, Acta Crystallogr., 60, 2126-2132 (2004).
Esther et al., The critical role of tissue angiotensin-converting enzyme as revealed by gene targeting in mice, *J. Clin. Invest*. 99: 2375-85 (1997).
Exner et al., Lesser response to angiotensin-converting-enzyme inhibitor therapy in black as compared with white patients with left ventricular dysfunction, *N. Engl. J. Med*. 344(18): 1351-7 (2001).
Fuchs et al., Role of the N-terminal catalytic domain of ACE investigated by targeted inactivation in mice, *J. Biol. Chem*. 279: 15946-53 (2004).
Goodford, A computational procedure for determining energetically favorable binding site on biologically important macromolecules, *J. Med. Chem*. 28: 849-7 (1985).
Goodsell et al., Automated docking of substrates to proteins by simulated annealing, *Proteins*, 8: 195-202 (1990).
Gordon et al., Degycosylation processing and crystallization of human testis angiotensin-converting enzyme, *Biochem. J*. 371: 437-42 (2003).
Gschwend et al., Molecular docking towards drug discovery, *J. Mol. Recognit*. 9: 175-86 (1996).
Hagaman et al., Angiotensin-converting enzyme and male fertility, *Proc. Natl. Acad. Sci. USA*, 95: 2552-7 (1998).
Holm et al., Protein folds and families: sequence and structure alignments, *Nucl. Acids Res*. 27: 244-7 (1999).
Hooper et al., An ACE structure, *Nat. Struct. Biol*. 10: 155-7 (2003).
Hooper, Families of zinc metalloproteases, *FEBS Lett*. 354: 1-6 (1994).
Horwell, The 'peptoid' approach to the design of non-peptide, small molecule agonists and antagonists of neuropeptides, *Trends Biotechnol*. 13: 132-4 (1995).
Howard et al., Transcription of testicular angiotensin-converting enzyme (ACE) is in initiated within the 12th intron of the somatic ACE Gene, *Mol. Cell Biol.*, 10: 4294-302 (1990).
Huang et al., Genetically increased angiotensin I-converting enzyme level and renal complications in the diabetic mouse, *Proc. Natl. Acad. Sci. USA*, 98: 13330-4 (2001).
Jaspard et al., Differences in the properties and enzymatic specificities of the two active sites of angiotensin I-converting enzyme (kininase II). Studies with bradykinin and other natural peptides, *J. Biol. Chem*. 268: 9496-503 (1993).
Jeunemaitre et al., Absence of linkage between the angiotensin convering enzyme locus and human essential hypertension, *Nat. Genet*. 1: 72-5 (1992).
Jones et al., Improved methods for building protein models in electron density maps and the location of errors in these models, *Acta Crystallogr. A*, 47: 110-19 (1991).
Junot et al., RXP 407, a selective inhibitor of the N-domain of angiotensin I-converting enzyme, blocks in vivo the degradation of hemoregularotry peptide acetyl-Ser-Asp-Lys-Pro with no effect on angiotensin I hydrolysis, *J. Pharmacol. Exp. Ther*. 297: 606-11 (2001).
Kasturi et al., Role of glycosylation in the biosynthesis and activity of rabbit testicular angio-tensin-converting enzyme, *Biochemistry*, 33: 6228-34 (1994).

(56) References Cited

OTHER PUBLICATIONS

Kasturi et al., The hydroxy amino acid in an Asn-X-Ser/Thr sequon can influence N-linked core glycosylation efficiency and the level of expression of a cell surface glycoprotein, *J. Biol. Chem.* 270: 14756-61 (1995).
Kim et al., Crystal structure of Drosophila angiotension I-converting enzyme bound to captotril and lisinopril, *FEBS Letters*, 538: 65-70 (2003).
Kobata, Use of endo- and exoglycosidases for structural studies of glycoconjugates, *Anal. Biochem.* 100: 1-14 (1979).
Kondoh et al., Angiotensin-converting enzyme is a GPI-anchored protein releasing factor crucial for fertilization, *Nat. Med.* 11: 160-6 (2005).
Kornfeld et al., Assembly of asparagine-linked oligosaccharides, *Annu. Rev. Biochem.* 54: 631-64 (1985).
Kost et al., Epitope-dependent blocking of the angiotensin-converting enzyme dimerization by monoclonal antibodies of the N-terminal domain of ACE: possible link of ACE dimerization and shedding from the cell surface, *Biochemistry*, 42: 6965-76 (2003).
Kraulis, Rastor3D Version 2.0. A program for photorealistic molecular graphics, *J. Appl. Crystallogr.* 24: 946-50 (1991).
Krege et al., Male-female differences in fertility and blood pressure in ACE-deficient mice, *Nature*, 375: 146-8 (1995).
Kroll et al., A multifunctional prokaryotic protein expression system: overproduction, affinity purification, and selective detection, *DNA Cell Biol.* 12: 441-53 (1993).
Kumar et al., Structure of testicular angiotensin-converting enzyme. A segmental mosaic isozyme, *J. Biol. Chem.* 264: 16754-8 (1989).
Kuraya et al., Release of O-linked sugar chains from glycoproteins with anhydrous hydrazine and pyridylamination of the sugar chains with improved reaction conditions, *Biochemistry*, 112: 122-6 (1992).
Laskowski et al., PROCHECK—A program to check the stereochemical quality of protein structures, *J. Appl. Crystallogr.* 26: 283-91 (1993).
Liu et al, Arg (1098) is critical for the chloride dependence of human angiotensin-1 converting enzyme C-domain catalytic activity, *J. Biol. Chem.* 276: 33518-25 (2001).
Marcic et al., Effects of the N-terminal sequence of ACE on the properties of its C-domain, *Hypertension*, 36: 116-21 (2000).
Marshall et al., Three-dimensional structure-activity relationships, *Trends Pharmacol. Sci.* 285-9 (1988).
Martin, 3D database searching in drug design, *J. Med. Chem*, 35: 2145-54 (1992).
Mattel et al., Cytogenet. Cell Genet., 51:1041 (1989).
Meng et al., Automated docking with grid-based energy evaluation, *J. Comp. Chem.*, 13(4): 505-24 (1992).
Merritt et al., Raster3D: photorealistic molecular graphics, *Methods Enzymol.* 277: 505-24 (1997).
Miranker et al., Functionality maps of binding sides: a multiple copy simultaneous search method, *Proteins*, 11: 29-34 (1991).
Misago et al., Suppressive effects of swainsonine and N-butyldeoxymojirimycin on human bone marrow neurtophil maturation, *Biochem. Biophys. Res. Commun.* 269: 219-25 (2000).
Murshudov, Refinement of macromolecular structures by the maximum-likelihood method, *Acta Crystallogr.* D53: 240-55 (1997).
Nachon et al., Engineering of a monomeric and low-glycosylated form of human butyrylcholinesterase: expression, purification, characterization and crystallization, *Eur. J. Biochem.* 269: 630-7 (2002).
Natesh et al., Crystal structure of the human angiotensin-converting enzyme-lisinopril complex, *Nature*, 421: 551-4 (2003).
Natesh et al., Database Protein Data Bank, Crystal structure of humane ACE (native), Feb. 7, 2003.
Natesh et al., Structural details on the binding of antihypertensive drugs captopril and enalaprilat to human testicular angiotensin I-converting enzyme, *Biochemistry*, 43: 8718-24 (2004).
Navia et al., Use of structural information in drug design, *Curr. Opin. Struct. Biol.* 2: 202-10 (1992).
Nishibata et al., Automatic creation of drug candidate structures based on receptor structure. Starting point for artificial lead generation, *Tetrahedron*, 47(43): 8985-90 (1991).
Oba et al., the N-terminal active center of human angiontensin-converting enzyme degrades Alzheimer amyloid beta-peptide, *Eur. J. Neurosci.* 21(3): 733-40 (2005).
Otwinowski et al., Processing of x-ray diffraction data collected in oscillation mode, *Methods Enzymol.* 276: 307-26 (1997).
Pang et al., Roles of the juxtamembrane and extracellular domains of angiotensin-converting enzyme in ectodomain shedding, *Biochem. J.* 358: 185-92 (2001).
Porath, Immobilized metal ion affinity chromatography, *Protein Expr. Purif.*, 3: 263-81 (1992).
Ramaraj et al., Selective restoration of male fertility in mice lacking angiotensin-converting enzymes by sperm-specific expression of the testicular isozyme, *J. Clin. Invest.* 102: 371-8 (1998).
Rawlings et al., Evolutionary families of metallopeptidases, *Methods Enzymol.*, 248: 183-228 (1995).
Roberge et al., A strategy for a convergent synthesis of N-linked glycopeptides on a solid support, *Science*, 269: 202-4 (1995).
Rousseau et al., The hemoregulatory peptide N-acetyl-Ser-Asp-Lys-Pro is a natural and specific substrate of the N-terminal active site of human angiotensin-converting enzyme, *J. Biol. Chem.* 270: 3656-61 (1995).
Sadhukhan et al., Different glycosylation requirements for the synthesis of enzymatically active angiotension-converting enzyme in mammalian cells and yeast, *J. Biol. Chem.* 271: 6429-34 (1996).
Schwager et al., Cleavage of disulfide-bridged stalk domains during shedding of angiotension-converting enzyme occurs at multiple juxtamembrane sites, *Biochemistry*, 40: 15624-30 (2001).
Schwager et al., Modulation of juxtamembrane cleavage ("shedding") of angiotensin-converting enzyme by stalk glycosylation: evidence for an alternative shedding protease, *Biochemistry*, 38: 10388-97 (1999).
Schwager et al., Phorbol ester-induced juxtamembrane cleavage of angiotensin-converting enzyme is not inhibited by a stalk containing intrachain disulfides, *Biochemistry*, 37: 15449-56 (1998).
Search report, PCT/GB03/03966, Feb. 25, 2004.
Shapiro et al., Anion activation of angiotensin converting enzyme: dependence on nature of substrate, *Biochemistry*, 22: 3850-7 (1983).
Simon et al., Peptoids: a modular approach to drug discovery, *Proc. Natl. Acad. Sci. USA*, 89: 9367-71 (1992).
Soubrier et al., Two putative active centers in human angiotensin I-converting enzyme revealed by molecular cloning, *Proc. Natl. Acad. Sci. USA*, 85: 9386-90 (1988).
Sturrock et al., Assignment of free and disulfide-bonded cysteine residues in testis angiotensin-converting enzyme: functional implications, *Biochemistry*, 35: 9560-6 (1996).
Sturrock et al., Limited proteolysis of human kidney angiotensin-converting enzyme and generation of catalytically active N- and C-terminal domains, *Biochem. Biophys. Res. Commun.* 236(1): 16-9 (1997).
Tarentino et al., Enzymatic deglycosylation of asparagine-linked glycans: purification, properties, and specificity of oligosaccharide-cleaving enzymes from Flavobacterium meningosepticum. *Methods Enzymol.* 230: 44-57 (1994).
Tatusova et al., BLAST 2 Sequences, a new tool for comparing protein and nucleotide sequence, *FEMS Microbiol. Lett.* 174: 247-50 (1999).
Thornberry et al., Determination of caspase specificities using a peptide combinatorial library, *Methods Enzymol.* 322: 100-10 (2000).
Towler et al., ACE2 X-ray structures reveal a large hinge-bending motion important for inhibitor binding and catalysis, *J. Biol. Chem.* 279: 17996-8007 (2004).
Trimble et al., Identification of distinct endoglycosidase (endo) activities in Flavobacterium meningsepticum: endo F1, endo F2, and endo F3. Endo F1 and endo H hydrolyze only high mannose and hybrid glycans, *J. Biol. Chem.* 266: 1646-51 (1991).
Two bright new faces in gene therapy, *Nat. Biotechnol.* 14: 556-51 (1996).

(56) References Cited

OTHER PUBLICATIONS

Ukeda et al., Peptides from peptic hydrolyzate of heated sardine meat that inhibit angiotensin I converting enzyme, Journal of Japan Society for Bioscience, Biotechnology and Agrochemistry, 66: 25-29 (1992) [Translation of abstract only].

Vagin et al., An approach to multi-copy search in molecular replacement, *Acta Crystallography*, D56: 1622-4 (2000).

Voronov et al., Temperature-induces selective death of the C-domain within angiotensin-converting enzyme molecule, *FEBS Letters*, 522: 77-82 (2002).

Waller et al., Three-dimensional quantitative structure-activity relationship of angiotensin-converting enzyme and thermolysin inhibitors. II. A comparison of CoMFA models incorporating molecular orbital fields and desolvation free energies based on active-analog and complementary-receptor-field alignment rules, *J. Med. Chem* 36: 2390-403 (1993).

Wei et al., The two homologous domains of human angiotensin I-converting enzyme are both catalytically active, *J. Biol Chem*. 266: 9002-8 (1991).

Wei et al., The two homologous domains of human angiotensin I-converting enzyme interact differently with competitive inhibitors, J. Biol Chem. 267: 13389-405 (1992).

Wheeler et al., Comparison on the N-linked glycans from soluble and GPI-anchored CD59 expressed in CHO cells, *Glycobiology*, 12: 261-71 (2002).

Whittle et al., Protein structure-based drug design, *Annu. Rev. Biophys Biomol. Struct*. 23: 349-75 (1994).

Wiencek, New strategies for protein crystal growth, *Annu. Rev. Biomed. Eng*. 1: 505-34 (1999).

Williams et al., Identification of two active site residues in human angiotensin I-converting enzyme, J. Biol. Chem. 269: 29430-4 (1994).

Wolff et al., The Cambrian peroid of nonviral gene delivery, *Nat. Biotechnol*. 16: 421-2 (1998).

Woodman et al., The N domain of somatic angiotensin-converting enzyme negatively regulates ectodomain shedding and catalytic activity, *Biochem. J*. 389: 739-44 (2005).

Yu et al., Identification of N-lined glycosylation sites in human testis angiotensin-converting enzyme and expression of an active deglycosylated form, *J. Biol. Chem*. 272: 3511-19 (1997).

Zhou et al., Role of asparagine-linked oligosaccharides in the function of the rat PTH/PTHrP receptor, *Biochemistry*, 39: 6514-20 (2000).

CRYSTALS OF ANGIOTENSIN-CONVERTING ENZYME (ACE)

This application is a continuation of U.S. patent application Ser. No. 14/297,500, filed Jun. 5, 2014, which is a continuation of U.S. patent application Ser. No. 12/160,562 (now U.S. Pat. No. 8,796,006), which is the U.S. national phase of International Patent Application No. PCT/GB2007/000064, filed Jan. 10, 2007, incorporated herein by reference in its entirety, which claims the benefit of priority of Great Britain Patent Application No. 0600406.3, filed Jan. 10, 2006.

Incorporated herein by reference in their entirety are computer-readable forms of a Sequence Listing and Tables A and B identified as follows: ASCII text file named "44091B SeqListing.txt"; 14,903 bytes; created Jul. 27, 2016 and "Tables.txt"' 1,469,829 bytes, created Jul. 27, 2016, respectively.

physiological roles and that they have negative effect on each other (Woodman et al., 2005).

Substrates such as the hemoregulatory peptide AcSDKP (Rousseau et al., 1995), angiotensin 1-7 (Deddish et al., 1998), and the enkephalin precursor $Met^5$-Enk-$Arg^6$-$Phe^7$ (Deddish et al., 1997) are specific for the N-domain, whereas the physiological substrates bradykinin and angiotensin I are hydrolysed with similar catalytic efficiency as compared with the C-domain.

It has been reported that the N-domain preferentially hydrolyses the A beta peptide of the amyloid precursor protein resulting in inhibition of A beta aggregation and cytotoxicity (Oba et al., 2005). The widely-used ACE inhibitor captopril shows modest selectivity for the N-domain (Wei et al., 1992); however, the phosphinic peptide inhibitor RXP-407 has a dissociation constant three orders of magnitude lower for the N-domain of the enzyme (Dive et al., 1999).

LENGTHY TABLES

The patent contains a lengthy table section. A copy of the table is available in electronic form from the USPTO web site (http://seqdata.uspto.gov/?pageRequest=docDetail&DocID=US09670473B2). An electronic copy of the table will also be available from the USPTO upon request and payment of the fee set forth in 37 CFR 1.19(b)(3).

FIELD OF INVENTION

The present invention relates to a crystal. In particular the present invention relates to a crystal of the N-domain of ACE protein.

The present invention also relates to methods, processes, domain specific modulators, pharmaceutical compositions and uses of the N-domain crystal and the structure co-ordinates thereof.

BACKGROUND TO THE INVENTION

Angiotensin-converting enzyme (peptidyl dipeptidase A, EC 3.4.15.1, ACE) is a zinc-dependent dipeptidyl carboxypeptidase with diverse physiological functions, including that of blood pressure regulation via angiotensin II production and bradykinin inactivation.

Somatic ACE (sACE), a type I transmembrane protein, is composed of two homologous catalytic domains (N- (SEQ ID NO: 1) and C- domains) arising from a gene duplication event (Soubrier et al., 1988). The germinal form of ACE (testis ACE, (tACE) SEQ ID NO: 2) (Ehlers et al., 1989) originates from the same gene as sACE , but has a tissue-specific promoter located within intron 12. Testis ACE (SEQ ID NO: 2) plays a crucial role in reproduction (Hagaman et al., 1998).

Despite sharing ~60% sequence identity with the C-domain, the N-domain has its own distinctive physicochemical and functional properties. It is thermally more stable than the C-domain (Voronov et al., 2002), more resistant to proteolysis under denaturing conditions and is less dependent on chloride activation relative to the C-domain (Wei et al., 1991; Jaspard et al., 1993). The N- and the C-domains are joined by a linker that is susceptible to proteolysis (Sturrock et al., (1997), *Biochem. Biophys. Res.* 236, 16-19). It has also been suggested that the N- and the C-domains have unique The N-domain has 10 N-linked sites of which 7 are unique to the N-domain. The different glycan profile of the N-domain is likely responsible for the carbohydrate-mediated dimerisation of sACE which has been described under certain conditions (Kost et al., 2003). Moreover, the difference in glycosylation could impact on the structural basis for epitope recognition and epitope mapping of the N-domain has revealed a region that might play a role in the relatively inefficient ectodomain shedding of sACE compared to its germinal isoform (Balyasnikova et al., 2005).

Both the N- and the C-domains of ACE protein are heavily glycosylated in nature, a feature that has hampered 3D structural determination of the protein and of each of the domains.

We previously described the 3D structure of the ACE protein (International Patent Application PCT/GB03/03966 (published as WO 04/024765). This 3D structure was that of the underglycosylated C-domain of ACE protein.

This underglycosylated 3D structure, however, provides limited information on the structure of the N-domain of ACE, nor is it ideal for screening or designing domain specific modulators suitable for pharmaceutical use nor indeed for studying the functional interaction between the N- and the C-domains of ACE protein.

Therefore there is a need to obtain a crystal of the N-domain of ACE protein with sufficient quality to allow crystallographic data to be obtained. Further, there is a need for such a crystal to allow the determination of the crystal structure of the N-domain of ACE. Finally there is a need for procedures for studying the interplay between the N- and the C-domains and screening for domain specific modulators using the 3D structural information of the N-domain of ACE protein.

SUMMARY OF THE INVENTION

The present inventors have now for the first time been able to describe the three-dimensional structure of the N-domain (SEQ ID NO: 1) of sACE protein.

According to a first aspect of the present invention there is provided a crystal of the N-domain (SEQ ID NO: 1) of ACE protein. Preferably the N-domain of ACE protein is minimally glycosylated.

Preferably, the N-domain of ACE protein is minimally glycosylated by incorporating one or more glycosylation sites and/or one or more partially glycosylated sites. More preferably, the minimally glycosylated N-domain of ACE protein is minimally glycosylated at amino acids 25, 45, 117, 289 and 480 of SEQ ID NO: 1.

Preferably the N-domain of ACE protein comprises an inter-domain linker region. This linker region joins the N- and the C-domains and has been reported to be susceptible to proteolysis (Sturrock et al., (1997), *Biochem. Biophys. Res.* 236, 16-19). No one has previously visualised this linker region in a 3D structure. No one has previously analysed the physiological role of this linker region and no one has previously studies the role of the linker in the functional interplay between the N- and the C-domains based on 3D structural data.

Preferably, the crystal of the N-domain of ACE protein (SEQ ID NO: 1) comprises atoms arranged in a spatial relationship represented by at least a portion of the structural coordinates set forth in Table A (SEQ ID NOs: 5 and 6) or Table B (SEQ ID NOs: 7 and 8).

Preferably, the crystal belongs to the space group $C222_1$.

Preferably, the crystal has the unit cell dimensions: a=101.12 Å, b=211.32 Å, c=171.27 Å.

Preferably, the crystal is a crystal of the N-domain of human ACE protein (SEQ ID NO: 1).

Preferably, the crystal of the N-domain of ACE protein comprises a ligand bound to the N-domain of ACE protein or a portion thereof. More preferably the ligand modulates the activity of the N-domain of ACE protein. More preferably the ligand is an inhibitor of the N-domain of ACE protein such as lisinopril or a derivative thereof. More preferably the crystal of the N-domain of ACE protein comprising lisinopril comprises atoms arranged in a spatial relationship represented by at least a portion of the structural co-ordinates set forth in Table B (SEQ ID NOs: 7 and 8).

Preferably the crystal of the N-domain of the ACE protein comprising the inhibitor lisinopril has the unit cell dimensions of: a=101.32 Å, b=211.90 Å, c=171.03 Å.

In a second aspect, the present invention relates to a method of preparing a crystal of the N-domain of ACE protein comprising the steps of: (a) culturing host cells expressing N-domain of ACE protein; (b) purifying the N-domain of ACE protein; and (c) crystallising the N-domain of ACE protein.

Preferably, the N-domain of ACE protein is crystallised using about 5 mM HEPES and about 0.1 mM PMSF with an equal volume of a reservoir solution containing about 0.2M lithium sulphate, about 15% PEG 4000, about 100 mM $CH_3COONa.3H_2O$ pH 4.9 and about 10 μM $ZnSO_4.7H_2O$.

Preferably, the crystal that is prepared has a structure defined by at least a portion of the structural co-ordinates set forth in Table A (SEQ ID NOs: 5 and 6) or Table B (SEQ ID NOs: 7 and 8).

Preferably, the crystal belongs to the space group $C222_1$.

Preferably, the crystal has the unit cell dimensions: a=101.12 Å, b=211.32 Å, c=171.27 Å.

Preferably, the N-domain of ACE protein is the N-domain of human ACE protein (SEQ ID NO:1).

Preferably, the N-domain of ACE protein is crystallised in the presence of a ligand. More preferably the ligand is a modulator of the N-domain of ACE protein. More preferably the ligand is an inhibitor of the N-domain of ACE protein such as lisinopril or a derivative thereof. More preferably the crystal of the N-domain of ACE protein comprising lisinopril comprises atoms arranged in a spatial relationship represented by at least a portion of the structural co-ordinates set forth in Table B (SEQ ID NOs: 7 and 8).

Preferably the crystal of the N-domain of the ACE protein comprising the inhibitor lisinopril has the unit cell dimensions of: a=101.32 Å, b=211.90 Å, c=171.03 Å.

Preferably the crystal of the N-domain of ACE protein that is prepared in the presence of a ligand is crystallised using about 5 mM HEPES and about 0.1 mM PMSF with an equal volume of a reservoir solution containing about 0.2M lithium sulphate, 18% PEG 4000, about 100 mM $CH_3COONa.3H_2O$ pH 4.9 and about 10 μM $ZnSO_4.7H_2O$.

In a third aspect, the present invention relates to a method of screening for a modulator of the N-domain of ACE protein wherein the method comprises the use of a crystal according to the present invention. Preferably, the screening method comprises the steps of: (a) providing at least a portion of the structural co-ordinates set forth in Table A (SEQ ID NOs: 5 and 6) or Table B (SEQ ID NOs: 7 and 8); (b) employing at least a portion of the structural coordinates set forth in Table A (SEQ ID NOs: 5 and 6) or Table B (SEQ ID NOs: 7 and 8) to design or select or synthesise a putative modulator of the N-domain of ACE protein; (c) contacting the putative modulator of the N-domain with the N-domain or a mutant, variant, homologue, derivative or fragment thereof in the presence of a substrate; and (d) screening the putative modulator of the N-domain of ACE protein in an assay for the potential to modulate the N-domain.

Comparisons of the 3D structures of the N-domain of ACE protein and C-domain of ACE protein show that the two domains are structurally very similar.

Therefore, according to a fourth aspect, the present invention relates to a method of screening for a modulator of the C-domain of ACE protein wherein the method comprises the use of a crystal according to the present invention. Preferably, the screening method comprises the steps of: (a) providing at least a portion of the structural co-ordinates set forth in Table A (SEQ ID NOs: 5 and 6) or Table B (SEQ ID NOs: 7 and 8); (b) employing at least a portion of the structural co-ordinates set forth in Table A (SEQ ID NOs: 5 and 6) or Table B (SEQ ID NOs: 7 and 8) to design or select or synthesise a putative modulator of the C-domain of ACE protein; (c) contacting the putative modulator of the C-domain with the C-domain or a mutant, variant, homologue, derivative or fragment thereof; and (d) screening the putative modulator of the C-domain of ACE protein in an assay for the potential to modulate the C-domain.

Preferably, at least a portion of the structural co-ordinates set forth in Table A (SEQ ID NOs: 5 and 6) or Table B (SEQ ID NOs: 7 and 8) and/or the putative modulator of the N-domain of ACE protein or C-domain of ACE protein and/or the substrate are provided on a machine-readable data storage medium comprising a data storage material encoded with machine readable data.

Preferably, the putative N-domain of ACE protein modulator or C-domain of ACE protein modulator is selected from a library of compounds. More preferably, the putative N-domain of ACE protein modulator or C-domain of ACE protein modulator is selected from a database. More preferably, the putative N-domain of ACE protein modulator or C-domain of ACE protein modulator is designed de novo. More preferably, the putative N-domain of ACE protein modulator or C-domain of ACE protein modulator is designed from a known ACE modulator. More preferably, the design or selection of the putative N-domain of ACE protein modulator or C-domain of ACE protein modulator is performed in conjunction with computer modelling.

Preferably, the putative N-domain of ACE protein modulator or C-domain of ACE protein modulator is useful in the prevention and/or treatment of ACE related disorder. More preferably, the ACE related disorder is hypertension, myocardial infarction or congestive heart failure.

In a fifth aspect, the present invention relates to a process comprising the steps of: (a) performing the method according to the third aspect and/or the fourth aspect of the present invention; (b) identifying one or more modulators of the N-domain and/or C-domain; and (c) preparing a quantity of those one or more N-domain modulators and/or C-domain modulators.

In a sixth aspect, the present invention relates to a process comprising the steps of: (a) performing the method according to the third aspect and/or the fourth aspect of the present invention; (b) identifying one or more N-domain modulators and/or C-domain modulators; and (c) preparing a pharmaceutical composition comprising those one or more N-domain modulators and/or C-domain modulators.

In a seventh aspect, the present invention relates to a process comprising the steps of: (a) performing the method according to the third aspect and/or the fourth aspect of the present invention; (b) identifying one or more N-domain modulators and/or C-domain modulators; (c) modifying those one or more N-domain modulators and/or C-domain modulators; and (d) optionally preparing a pharmaceutical composition comprising those one or more N-domain modulators and/or C-domain modulators.

In an eighth aspect, the present invention relates to a method of obtaining structural information about a molecule or a molecular complex of unknown structure by using at least a portion of the structure co-ordinates of the N-domain of ACE protein, comprising the steps of: (a) generating X-ray diffraction data from a crystallised molecule or molecular complex; (b) applying at least a portion of the structure co-ordinates of the N-domain of ACE protein to said X-ray diffraction pattern to generate a three dimensional electron density map of at least a portion of the molecule or molecular complex; and (c) using all or a portion of the structure co-ordinates of the N-domain of ACE protein to generate homology models of the N-domain of ACE protein. Preferably the structural information of the structure co-ordinates of ACE protein are used for domain co-operativity studies.

In a ninth aspect, the present invention relates to a modulator of the N-domain of ACE protein and/or the C-domain of ACE protein identified by the method according to the third aspect and/or the fourth aspect of the present invention. Preferably, the modulator inhibits the N-domain of ACE protein and/or the C-domain of ACE protein.

In a tenth aspect, the present invention relates to a pharmaceutical composition comprising an N-domain of ACE protein modulator and/or a C-domain of ACE protein modulator according to the ninth aspect of the present invention and a pharmaceutically acceptable carrier, diluent, excipient or adjuvant or any combination thereof.

In an eleventh aspect, the present invention relates to a method of preventing and/or treating an ACE related disorder comprising administering a modulator of the N-domain of ACE protein and/or the C-domain of ACE protein according to the ninth aspect of the present invention and/or a pharmaceutical composition according to the tenth aspect of the present invention, wherein said modulator of the N-domain of ACE protein and/or the C-domain of ACE protein and/or said pharmaceutical composition is capable of causing a beneficial preventative and/or therapeutic effect.

In a twelfth aspect, the present invention relates to a computer for producing a three-dimensional representation of the N-domain of ACE protein wherein said computer comprises: (a) a computer-readable data storage medium comprising a data storage material encoded with computer-readable data, wherein said data comprises the structure co-ordinates of the N-domain of ACE protein; (b) a working memory for storing instructions for processing said computer-readable data; (c) a central-processing unit coupled to said working memory and to said computer-readable data storage medium for processing said computer-machine readable data into said three-dimensional representation; and (d) a display coupled to said central-processing unit for displaying said three-dimensional representation.

In a thirteenth aspect, the present invention relates to a machine-readable data storage medium comprising a data storage material encoded with machine-readable data, wherein the data is defined by at least a portion of the structural co-ordinates of the N-domain (SEQ ID NO: 1) of ACE protein set forth in Table A (SEQ ID NOs: 5 and 6) or Table B (SEQ ID NOs: 7 and 8).

In a fourteenth aspect, the present invention relates to the use of an N-domain of ACE protein crystal in the preparation of a medicament to prevent and/or treat an ACE related disorder. Preferably, the ACE related disorder is hypertension, myocardial infarction or congestive heart failure.

In a fifteenth aspect, the present invention relates to the use of at least a portion of the structural co-ordinates set forth in Table A (SEQ ID NOs: 5 and 6) or Table B (SEQ ID NOs: 7 and 8) to screen for modulators of the N-domain of ACE protein and/or C-domain of ACE protein.

In a sixteenth aspect, the present invention relates to the use of at least a portion of the structural co-ordinates set forth in Table A (SEQ ID NO: 5 and 6) or Table B (SEQ ID NOs: 7 and 8) to solve the structure of the crystalline form of any other domain with significant amino acid sequence homology to any functional domain of the N-domain of ACE protein.

In a seventeenth aspect, the present invention relates to the use of at least a portion of the structural co-ordinates set forth in Table A (SEQ ID NOs: 5 and 6) or Table B (SEQ ID NOs: 7 and 8) in molecular design techniques to design, select and synthesise modulators of the N-domain of ACE protein and/or C-domain of ACE protein.

In an eighteenth aspect, the present invention relates to the use of at least a portion of the structural co-ordinates set forth in Table A (SEQ ID NOs: 5 and 6) or Table B (SEQ ID NOs: 7 and 8) in the development of compounds that can isomerise to reaction intermediates in the chemical reaction of a substrate or other compound that binds to the N-domain of ACE protein and/or the C-domain of ACE protein.

In a nineteenth aspect, the present invention relates to the use of at least a portion of the structural co-ordinates set forth in Table A (SEQ ID NOs: 5 and 6) or Table B (SEQ ID NOs: 7 and 8) to screen small molecule databases for chemical entities or compounds that modulate the N-domain of ACE protein and/or C-domain of ACE protein.

In a twentieth aspect, the present invention relates to the use of at least a portion of the structural co-ordinates set forth in Table A (SEQ ID NOs: 5 and 6) or Table B (SEQ ID NOs: 7 and 8) to solve the structure of the crystalline form of any other domain with significant amino acid sequence homology to any functional domain of the N-domain of ACE protein. Preferably, the structure of the crystalline form of any other domain with significant amino acid sequence homology to any functional domain of the N-domain of ACE protein is solved using molecular replacement.

In a twenty first aspect, the present invention relates to the use of at least a portion of the structural co-ordinates set forth in Table A (SEQ ID NOs: 5 and 6) or Table B (SEQ ID NOs: 7 and 8) to identify the binding site of any modulator of the N-domain of ACE protein. Preferably the binding site is that of lisinopril or derivatives thereof.

DETAILED DESCRIPTION OF THE INVENTION

N-Domain of Ace Protein

ACE (EC 3.4.15.1) is a membrane associated peptidyl dipeptidase.

There are two tissues specific isoforms of ACE protein differentially transcribed from the same gene.

Somatic ACE (sACE), a type I transmembrane protein, is composed of two homologous catalytic N- (SEQ ID NO: 1) and C- domains, arising from a gene duplication event (Soubrier et al., 1988).

Germinal ACE (testis ACE, (tACE) (SEQ ID NO: 2)) has a tissue-specific promoter located within intron 12 (Ehlers et al., 1989).

Despite sharing ~60% sequence identity with the C-domain, the N-domain (SEQ ID NO: 1) has its own distinctive physicochemical and functional properties. It has also been reported that the two domains display negative co-operativity effect on each other (Woodman et al., 2005). In the present invention, co-operativity studies between the N- (SEQ ID NO: 1) and C-domains of ACE protein is based on studies carried out by Guy et al., 2003 (Biochemistry, 42:13185-13192) and Towler et al., 2004 (The Journal of Biological Chemistry, 17:17996-18007). In their studies, the authors compare ACE structures with those of the ACE2 (SEQ ID NO: 3) homologue that more closely resembles the N-domain (SEQ ID NO: 1) of the ACE protein. See FIG. 4 below.

As used herein the term "negative co-operativity" refers to the capacity of the two domains of ACE protein to modulate the biochemical activities of each other. By way of example the N-domain may cause steric hindrance of the C-domain by preventing substrate from accessing the active site of the C-domain and vice versa the C-domain may cause steric hindrance of the N-domain by preventing substrate from accessing the active site of the N-domain.

The N- and the C-domains are heavily glycosylated, which has hampered the determination of the 3D structure of the ACE protein.

Previously we described the 3D structure of the C-domain of undeglycosylated ACE protein (see International Patent Application PCT/GB03/03966 (published as WO 04/024765)).

The present inventors have now been able to obtain a minimally glycosylated N-domain of ACE protein.

As used herein the term "minimally glycosylated" means that one or more oligosaccharide chains are linked to one or more amino acid residues in the N-domain of ACE protein. As used herein the term "oligosaccharide" refers to a carbohydrate molecule which comprises less than 10 sugar molecules where the sugar molecules can be any one or more of monosaccharides, di-, tri-, and/or tetra-saccharides.

As used herein, the term "N-domain of ACE protein" includes all vertebrate and mammalian forms of the N-domain of ACE protein and is intended to cover mutants, variants, homologues, derivatives and fragments thereof. Preferably, the mutants, variants, homologues, derivatives and fragments thereof have the activity of the N-domain of ACE protein. Preferably the N-domain of the ACE protein is minimally glycozylated.

Crystal

In one aspect of the present invention, there is provided a crystal structure of the N-domain of ACE protein in its minimally glycozylated form and its ligand-bound form.

As used herein, the term "crystal" means a structure (such as a three dimensional (3D) solid aggregate) in which the plane faces intersect at definite angles and in which there is a regular structure (such as internal structure) of the constituent chemical species. Thus, the term "crystal" can include any one of: a solid physical crystal form such as an experimentally prepared crystal, a 3D model based on the crystal structure, a representation thereof—such as a schematic representation thereof, a diagramatic representation thereof, or a data set thereof for a computer.

The crystals of the present invention may be prepared by purifying the N-domain of ACE protein and then crystallising the purified protein. The N-domain of ACE protein may also be prepared by expressing a nucleotide sequence encoding the N-domain of ACE protein in a suitable host cell.

In one preferred embodiment, the N-domain of ACE crystal comprises the inter-domain linker region.

The N-domain of ACE protein may be purified using various methods known to a person skilled in the art, for example, from conditioned media by affinity chromatography on a Sepharose-28-lisinopril affinity resin (Yu et al. 1997). The protein may be quantified by amino acid analysis and assayed for activity using the substrate hippuryl-L-histidyl-L-leucine, as described previously (Ehlers, M R E, Chen, Y-N, Riordan, J F (1991) *Proc. Natl. Acad. Sci. USA* 88, 1009-1013).

The purified N-domain of ACE proteins may be stored at −20° C. in 5 mM HEPES and 0.1 mM PMSF.

Concentration may be performed with the aid of a filtration system and the protein concentrate may be immediately used for crystallisation purposes. The protein concentrate may be crystallised using, for example, the vapour diffusion hanging drop method at a temperature of from about 4° C. to about 30° C., preferably from about 8° C. to about 20° C., more preferably from about 12° C. to about 18° C., most preferably at about 16° C. The crystallisation temperature may be dependent on the additives present in the protein solution.

Typically, the best crystals for the N-domain of ACE proteins are grown at a temperature in the range of from 10 to 20° C., preferably from 12 to 18° C., most preferably at 16° C. by the vapour diffusion hanging drop method by mixing 1 μl of the protein solution at about 4 mg/ml. The solution comprising HEPES in the range of from 1 to 10 mM, preferably in the range of from 2 to 8 mM, more preferably in the range of from 4 to 6 mM, most preferably 5 mM HEPES and PMSF in the range of from 0.025 to 0.2%, preferably from 0.05 to 0.15%, more preferably from 0.075 to 0.125, most preferably 0.1% PMSF with an equal volume of a reservoir solution. The reservoir solution comprising lithium sulphate in the range of from 0.025 to 0.4M, preferably in the range of from 0.05 to 0.35M, more preferably from 0.075 to 0.3M, most preferably containing 0.2M lithium sulphate, PEG 4000 in the range of from 5% to 25%, preferably from 10% to 20%, most preferably from 15% to 18% PEG 4000, $CH_3COONa.3H_2O$ in the range of from 50 to 150 mM, preferably from 75 to 125 mM, more preferably from 90 to 110 mM, most preferably 100 mM $CH_3COONa.3H_2O$, wherein the $CH_3COONa.3H_2O$ has a pH in the range of from 3.9 to 5.9, preferably a pH from 4.5 to 5.5, more preferably a pH from 4.7 to 5.2, most preferably a pH of 4.9 and $ZnSO_4.7H_2O$ in the range of from 5 to 20 μM, preferably from 7.5 to 12.5 μM, most preferably 10 μM $ZnSO_4.7H_2O$.

Crystals usually appear within 1 to 2 weeks and grow to their maximum size after about a month.

The present invention related to a crystal of the N-domain of ACE comprising atoms arranged in a spatial relationship represented by at least a portion of the structural coordinates set forth in Table A (SEQ ID NOs: 5 and 6) or Table B (SEQ ID NOs: 7 and 8).

Preferably, the crystal belongs to the space group $C222_1$ and unit cell dimensions: a=101.12 Å, b=211.32 Å, c=171.27 Å.

Preferably, the N-domain of ACE protein is the N-domain of any vertebrate and mammalian.

Preferably the N-domain of ACE protein is the N-domain of human ACE protein (SEQ ID NO: 1).

Complexes may be obtained by growing the crystals in the presence of a ligand—such as a test compound. In these experiments the protein solution is mixed with the ligand and an equal volume of the reservoir solution before setting up the crystallisation. Single crystals suitable for diffraction work typically appear after about 1-2 weeks.

Typically, the protein comprising the N-domain of ACE protein is purified to homogeneity for crystallisation. Purity of the N-domain of ACE protein may be measured by typical techniques such as SDS-PAGE, mass spectrometry and hydrophobic HPLC.

The structure of the crystals of the invention may contain a portion—such as at least 25%, at least 50%, at least 75%, or preferably at least 90%, at least 95%, at least 98%, or at least 99% —of the co-ordinates set forth in Table A (SEQ ID NOs: 5 and 6) or Table B (SEQ ID NOs: 7 and 8). Preferably, the crystal structure of the invention contains all of the co-ordinates set forth in Table A (SEQ ID NOs: 5 and 6) or Table B (SEQ ID NOs: 7 and 8)

Preferably, the crystals are usable in X-ray crystallography techniques.

Preferably, the crystals used can withstand exposure to X-ray beams used to produce diffraction pattern data necessary to solve the X-ray crystallographic structure.

Preferably, prior to data collection, the crystals are flash-cooled at about 100 K in a cryoprotectant. The cryoprotectant comprising lithium sulphate in the range of from 0.025 to 0.4M, preferably in the range of from 0.05 to 0.35M, more preferably from 0.075 to 0.3M, most preferably containing 0.2M lithium sulphate, PEG 4000 in the range of from 5% to 25%, preferably from 10% to 20%, most preferably from 15% to 18% PEG 4000, $CH_3COONa.3H_2O$ in the range of from 50 to 150 mM, preferably from 75 to 125 mM, more preferably from 90 to 110 mM, most preferably 100 mM $CH_3COONa.3H_2O$, wherein the $CH_3COONa.3H_2O$ has a pH in the range of from 3.9 to 5.9, preferably a pH from 4.5 to 5.5, more preferably a pH from 4.7 to 5.2, most preferably a pH of 4.9 and $ZnSO_4.7H_2O$ in the range of from 5 to 20 μM, preferably from 7.5 to 12.5 μM, most preferably 10 μM $ZnSO_4.7H_2O$.

The X-ray data may be collected at a Synchrotron Radiation Source. Preferably, the X-ray data are collected at a Synchrotron Radiation Source at 100° K.

Preferably, the crystal has a resolution determined by X-ray crystallography of about 3.5 Å or less, more preferably a resolution of about 3.0 Å or less, more preferably a resolution of about 2.8 Å or less, more preferably, a resolution of about 2 Å or less, more preferably, a resolution of about 1.5 Å or less, most preferably, 1 Å or less.

Glycosylation of the N-Domain of Ace Protein

Many proteins in eukaryotic cells are glycoproteins that contain oligosaccharide chains covalently linked to certain amino acids. Glycosylation is known to affect protein folding, interaction between protein domains, localisation and trafficking, protein solubility, antigenicity, biological activity and half-life, as well as cell-cell interactions.

Protein glycosylation can be divided into four main categories mainly depending on the linkage between the amino acid and the sugar molecule. These are N-linked glycosylation, O-linked glycosylation, C-mannosylation and GPI anchor attachments. N-glycosylation is characterised by the addition of a sugar to the amino group of an asparagine.

For N-glycosylation, the sequence motif Asn-Xaa-Ser/Thr (wherein Xaa is any amino acid other than Pro) has been defined as a prerequisite for glycosylation. Although rare, the sequence motif Asn-Xaa-Cys can also be an acceptor site. N-glycans can be subdivided into three distinct groups called 'high mannose type', 'hybrid type', and 'complex type', with the common pentasaccharide core—Manp(alpha1,6)-(Manp(alpha1,3))-Manp(beta1,4)-GlcpNAc(beta1,4) GlcpNAc(beta1,N)-Asn—occurring in all three groups. The relationship between all three types can be ascribed to the fact that they originate from one precursor oligosaccharide which contains the described common pentasaccharide core Man3-GlcNAc2, and some additional sugar residues and the non-reducing end, and is then processed enzymatically to yield these three types. Since the hydroxyl group of Ser/Thr is thought to be involved in hydrogen bonding during the enzymatic attachment of the oligosaccharide precursor molecule to yield a favourable conformation for the action of the oligosaccharyltransferase, it has been suggested for proline that the steric hindrance might be too large (Kornfeld (1985) *Ann. Rev. Biochem.* 54: 631-64), preventing glycosylation at Pro containing sites. The negative influence of aspartic acid towards glycosylation can be ascribed to the negative charge on the side chain of this residue. In addition some cases have been reported where Ser/Thr is replaced by cysteine. While Ser replacement by Cys generally leads to decreased glycosylation, it has been shown (Kasturi 1995 *J. Biol. Chem.* 270: 14756-61) that substitution by Thr at a given potential glycosylation site can lead to increased glycosylation. This is in accordance with the model of hydrogen bonding being an important factor during the attachment of the precursor molecule to the protein. Although there are usually many potential glycosylation sites in a protein it has been estimated that glycosylation occurs only at one third of them. Mostly at those sites where the surrounding amino acids allow the formation of a beta turn.

Various glycoforms of ACE have been described. By way of example, Sadhukhan & Sen disrupted specific glycosylation sites in rabbit tACE to elucidate the glycosylation requirements for the expression and processing of active testis ACE. There are five potential N-linked glycosylation sites in the rabbit tACE sequence, with an additional six in the somatic form. A null mutant, where all five sites had been disrupted, behaved similarly to wild-type tACE expressed in the presence of the glycosylation-inhibitor, tunicamycin. It was degraded intracellularly and failed to be detected in culture medium, confirming previous findings that tACE requires N-linked glycosylation to be expressed in an active form. Expression of the remaining mutants showed a preference for N-linked glycosylation at the N-terminus and that the presence of sugars at a single N-terminal site was necessary and sufficient to produce enzymatically-active tACE that was solubilised. The presence of glycosylation is not site-specific, as mutants that have either the first site or second site intact are expressed and active. However, glycosylation at the third site alone is not sufficient to produce active protein in HeLa cells, albeit this mutant was expressed in yeast, indicating that the requirements for glycosylation are cell-specific.

N-linked glycosylation of human tACE (SEQ ID NO: 2) expressed in CHO cells at each site has been identified by MALDI-TOF mass spectrometry. There are seven potential N-linked sites in human tACE (SEQ ID NO: 2), five of which are complementary to the sites in rabbit tACE (7a). The unique sites lie within the ectodomain (the fourth site) and in the juxtamembrane stalk region, adjacent to the cleavage site (the seventh site). As with the rabbit form, there appears to be a preference for glycosylation at the N-terminus as evidenced by MALDI-TOF mass spectrometry of glycopeptides (Yu et al., 1997) and mutagenesis (Gordon et al., 2003) of glycosylation sites. Inhibition of complex oligosaccharide formation using a glucosidase I inhibitor N-butyldeoxynojirimycin (NB-DNJ) led to the production of an active glycoform that was electrophoretically homogeneous.

There are ten putative N-glycosylation sites on the human N-domain (SEQ ID NO: 1) of ACE protein and Fourier difference density was observed at five of these sites according to the crystal of the present invention.

Suitably, the crystal of the N-domain of ACE protein may comprise minimally glycosylated N-domain of ACE protein or a fragment thereof. For example, the minimally glycosylated N-domain of ACE protein may comprise the sequence presented as SEQ ID NO: 1.

To obtain a minimally glycosylated N-domain of ACE protein, various methods known to a person skilled in the art may be used. Both chemical and enzymatic methods may be used. Hydrazinolysis of glycoproteins (Kuraya, N & Hase (1992) J Biochem (Tokyo) 112:122-126), is capable of removing both N- and O-linked sugars, although this results in the complete destruction of the protein component and is therefore not suitable if recovery of the protein is desirable. More delicate chemical methods may be used such as trifluoromethanesulphonic acid (TFMS), however this method may also lead to a partial protein destruction. Alternatively, or in addition, other methods—such as site directed mutagenesis of glycosylated amino acids may also be employed.

Enzymatic methods which provide for partial sugar removal with no protein degradation may also be used.

Use of the enzyme PNGase F is an effective method of removing most N-linked oligosaccharides from glycoproteins (Tarentino & Plummer (1994) *Methods in Enzymology,* 230: 44-57). The oligosaccharide is left intact and therefore suitable for further analysis (the asparagine residue from which the sugar is removed is deaminated to aspartic acid, the only modification to the protein).

Other commonly used endoglycosidases include Endoglycosidase H (Kobata (1979) *Anal Biochem* 100:1-14) and Endoglycosidase F (Trimble & Tarentino (1991) *J. Biochem.* 266:1646-1651). In a preferred method, the N-domain of ACE protein is digested with Endoglycosidase H (30 mU) in a suitable buffer—such as 100 mM sodium phosphate, 0.1 mM $ZnCl_2$ and 1% BSA, pH 6.0 for 16 h at 37° C. The endo H-treated protein is passed through a lectin affinity column consisting of equal parts of concanavalin A, wheat germ, and lentil lectin, after equilibration with 20 mM Tris-HCl, 0.5 M NaCl at pH 7.4. The minodeglycosylated ACE is collected in the flowthrough. Free oligosaccharides and any other impurities are removed from the flowthrough fraction by a final lisinopril-Sepharose affinity chromatography step. The homogeneity of the ACE protein after deglycosylation is confirmed by SDS-PAGE on a 4-20% acrylamide gel and MALDI-TOF mass spectrometry.

By way of example, a minimally glycosylated N-domain of ACE protein can be obtained by incubating suitable host cells such as CHO cells until confluent and then substituting the growth medium with medium comprising 1% FCS, 0.05% albumax I (Gibco BRL), 20 μM MSX and 1.5 mM of the glucosidase I inhibitor N-butyldeoxynojirimycin (NB-DNJ) (Toronto Research Chemicals Inc. B691000 Lot 14-EG-91-1 and B691000 12-Cf-146-2).

Preferably, the crystal of the N-domain of ACE protein comprises glycosylated N-domain of ACE protein or a fragment thereof. More preferably, the crystal of the N-domain of ACE protein comprises a minimally glycosylated N-domain of ACE protein or a fragment thereof. More preferably, the crystal of the N-domain of ACE protein comprises N-glycosylation of asparagine residues. More, preferably the asparagine residues are N-glycosylated with high mannose oligosaccharides.

Preferably, one or more of the asparagine residues of the N-domain of ACE protein can be N-glycosylated. More preferably, one or more of the asparagine residue of SEQ ID NO:1 are N-glycosylated. More, preferably one or more of the asparagine residues 25, 45, 117, 289 and 480 of SEQ ID No: 1 can be N-glycosylated.

Preparing a Crystal of the N-Domain of Ace Protein

In another aspect, the present invention relates to a method of preparing a crystal of the N-domain of ACE protein, comprising the steps of (a) culturing host cells comprising N-domain of ACE protein; (b) purifying the N-domain of ACE protein; and (c) crystallising the N-domain of ACE protein.

Preferably, the N-domain of ACE protein comprises an inter-domain linker region.

The N-domain of ACE protein may be purified using the methods described herein.

Preferably, the N-domain of ACE protein is crystallised in the presence of a ligand, for example, a modulator of the N-domain of ACE protein.

Modulators

The role of ACE protein in the pathogenesis of hypertension has resulted in an intensive search for modulators (eg. inhibitors) of the enzyme that could act as antihypertensive drugs (eg. U.S. Pat. Nos. 3,891,616, 3,947,575, 4,052,511 and 4,053,651). Therapeutic vasodepressors—such as the compound captopril (D-2-methyl-3-mercaptopropanoyl-L-proline)—have been synthesised as ACE inhibitors. Numerous synthetic peptide derivatives have also been shown to be ACE inhibitors as disclosed in U.S. Pat. No. 3,832,337.

Natural substances that inhibit ACE include snake venom and those derived from foodstuffs—such as ACE inhibiting peptides produced by enzymatic hydrolysis of proteins, such as casein or fish meat protein (by Hiroyuki Ukeda, Nippon Nogei Kagaku Kaishi (*Journal of Japan Society for Bioscience*, Biotechnology, and Agrochemistry, 66(1), 25-29 (1992)).

ACE inhibiting synthetic substances include captopril (D-2-methyl-3-mercaptopropanoyl-L-proline) which has already been put to practical application as an orally administered vasodepressor.

However, many currently used ACE inhibiting substances exhibit side effects in many cases and special attention needs to be exercised.

The present invention offers a novel concept in the field of ACE protein inhibitor design by providing conditions suitable for generating specific inhibitors to more precisely target and regulate the activity of the N- and/or C-domains of ACE protein. Preferably the modulators are N-domain of ACE protein specific and/or C-domain of ACE protein specific. These novel modulators can advantageously have reduced side effects.

The present invention provides the use of molecular design techniques to design, select and synthesise chemical entities and compounds, including ACE modulating compounds, capable of binding to the N-domain of ACE protein, in whole or in part.

Thus, in a further aspect, the present invention relates to a method of screening for a modulator of the N-domain of ACE protein wherein the method comprises the use of a crystal of the N-domain of ACE protein.

Preferably, the method comprises the steps of: (a) providing at least a portion of the structural co-ordinates set forth in Table A (SEQ ID NOs: 5 and 6) or Table B (SEQ ID NOs: 7 and 8); (b) employing at least a portion of the structural co-ordinates set forth in Table A (SEQ ID NOs: 5 and 6) or Table B (SEQ ID NOs: 7 and 8) to design or select or synthesise a putative modulator of the N-domain of ACE protein; (c) contacting the putative modulator of the N-domain of ACE protein with the N-domain of ACE protein or a mutant, variant, homologue, derivative or fragment thereof in the presence of a substrate; and (d) screening the putative modulator of the N-domain of ACE protein in an assay for the potential to modulate the N-domain.

By way of example, the structure co-ordinates may be used to design compounds that bind to the N-domain of ACE enzyme and may alter the physical properties of the compounds (e.g. solubility) or the domain or the enzyme itself. This invention may be used to design compounds that act as modulators—such as competitive inhibitors—of the N-domain of ACE protein by binding to all or a portion of the active site of the N-domain of ACE protein. Compounds may also be designed that act as non-competitive inhibitors of the N-domain of ACE protein. These non-competitive inhibitors may bind to all or a portion of the N-domain of ACE protein already bound to its substrate and may be more potent and specific than known N-domain of ACE protein inhibitors that compete only for the N-domain of ACE protein active site. Similarly, non-competitive inhibitors that bind to and inhibit the N-domain of ACE protein whether or not it is bound to another chemical ligand may be designed using the structure co-ordinates of the N-domain of ACE protein as described herein.

By way of example, it may be found that the COOH-binding active site residue differs between the N- and C-domain of ACE protein active sites and/or that it may be amenable to the incorporation of a functionality that can covalently modify this residue to produce an irreversible domain specific inhibitor design.

Due to the significant structural similarity between the N-domain and the C-domain of ACE protein it is envisaged that the structural co-ordinates of the crystal of the N-domain can also be used to design modulators which are specific for the C-domain of ACE protein.

Accordingly, in a further aspect, the present invention relates to a method of screening for a modulator of the C-domain of ACE protein wherein the method comprises the use of a crystal of the N-domain of ACE protein. Preferably, the method comprises the steps of: (a) providing at least a portion of the structural co-ordinates set forth in Table A (SEQ ID NOs: 5 and 6) or Table B (SEQ ID NOs: 7 and 8); (b) employing at least a portion of the structural coordinates set forth in Table A (SEQ ID NOs: 5 and 6) or Table B (SEQ ID NOs: 7 and 8) to design or select or synthesise a putative modulator of the C-domain of ACE protein; (c) contacting the putative modulator of the C-domain of ACE protein with the C-domain of ACE protein or a mutant, variant, homologue, derivative or fragment thereof in the presence of a substrate; and (d) screening the putative modulator of the C-domain of ACE protein in an assay for the potential to modulate the C-domain.

By way of example, the structure co-ordinates of the N-domain may be used to design compounds that bind to the C-domain of ACE enzyme and may alter the physical properties of the compounds (e.g. solubility) or the domains or the enzyme itself. This invention may be used to design compounds that act as modulators—such as competitive inhibitors—of the C-domain of ACE protein by binding to all or a portion of the active site of the C-domain of ACE protein. Compounds may also be designed that act as non-competitive inhibitors of the C-domain of ACE protein. These non-competitive inhibitors may bind to all or a portion of the C-domain of ACE protein already bound to its substrate and may be more potent and specific than known C-domain of ACE protein inhibitors that compete only for the C-domain of ACE protein active site. Similarly, non-competitive inhibitors that bind to and inhibit the C-domain of ACE protein whether or not it is bound to another chemical ligand may be designed using the structure co-ordinates of the N-domain of ACE protein as described herein. Advantageously, the specific modulators of the C-domain of ACE protein do not adversely affect the enzymatic activity of the N-domain of ACE protein. By way of example, such C-domain specific inhibitors can permit the N-domain to hydrolyse the vasodilator bradykinin and thus alleviate side effects such as persistent cough and angioedema. Accordingly, the C-domain specific modulators identified by the screening methods described herein may have the capacity to overcome certain side effects.

By way of a further example, the C-domain specific inhibitors can also permit the hydrolysis of the N-domain specific hemoregulatory peptide AcSDKP.

In a preferred embodiment, at least a portion of the structural co-ordinates set forth in Table A (SEQ ID NOs: 5 and 6) or Table B (SEQ ID NOs: 7 and 8) and/or the putative modulator of the N-domain of ACE protein or C-domain of ACE protein and/or the substrate are provided on a machine-readable data storage medium comprising a data storage material encoded with machine readable data.

A crystal of the N-domain of ACE may be probed with a variety of different chemical entities or test compounds to determine optimal sites for interaction between modulators of the N-domain of ACE protein or the C-domain of ACE protein and the enzyme. For example, X-ray diffraction data collected from crystals grown in the presence of chemical entities or test compounds may allow the elucidation of how the chemical entities or test compounds interact with the N-domain of ACE protein or the C-domain of ACE protein. Molecules that bind to those sites can then be designed and synthesised and tested for their capacity to modulate the activity of the N-domain of ACE protein.

The present invention may also allow the development of compounds that can isomerise to reaction intermediates in the chemical reaction of a substrate or other compound that bind to the N-domain of ACE protein or the C-domain of ACE protein. Thus, the time-dependent analysis of structural changes in the N-domain of ACE protein during its interaction with other molecules may be performed. The reaction intermediates of the N-domain of ACE protein or the C-domain of ACE protein may also be deduced from the reaction product in complex with the N-domain of ACE protein. Such information is especially useful to design improved analogues of known N-domain or C-domain modulators or to design new N-domain or C-domain modulators based on the reaction intermediates and the modulator complex. This may provide a new route for designing N-domain or C-domain of ACE protein modulators with high domain specificity and stability. Preferably, this provides a new route for designing N-domain or C-domain of ACE protein modulators with high domain specificity, high stability and low toxicity.

Small molecule databases or test compounds may be screened for chemical entities or compounds that can bind in whole, or in part, to the N-domain or C-domain of ACE protein. Thus, in a preferred embodiment, the putative N-domain or C-domain modulator is selected from a library of compounds or a database. In this screening, the quality of fit of such entities or compounds to the binding site may be judged by various methods—such as shape complementarity or estimated interaction energy (Meng, E. C. et al., *J. Comp. Chem.,* 13, pp. 505-524 (1992)).

Because the N-domain of ACE protein or a mutant, variant, homologue, derivative or fragment thereof may crystallise in more than one crystal form, the structure co-ordinates of the N-domain of ACE protein, or portions thereof, may be particularly useful to solve the structure of other crystal forms of the N-domain of ACE protein. They may also be used to solve the structure of the N-domain of ACE protein mutants, N-domain of ACE protein variants, N-domain of ACE protein homologues, N-domain of ACE protein derivatives, N-domain of ACE protein fragments and N-domain of ACE protein complexes.

Preferably, the structure co-ordinates of the N-domain of ACE protein are used to solve the structure of the crystalline form of any other protein with significant amino acid sequence homology to any functional domain of the N-domain of ACE protein. By way of example, molecular replacement may be used. In this method, the unknown crystal structure, whether it is another crystal form of the N-domain of ACE protein, N-domain of ACE protein mutant, N-domain of ACE protein variant, N-domain of ACE protein homologue (eg. another protein with significant amino acid sequence homology to any functional domain of the N-domain of ACE protein), N-domain of ACE protein derivative, N-domain of ACE protein fragments or N-domain of ACE protein complex may be determined using the N-domain of ACE protein structure co-ordinates of the present invention. This method will provide a more accurate structural form for the unknown crystal more quickly and efficiently than attempting to determine such information ab initio.

Preferably, the structural co-ordinates of the N-domain of ACE protein are used for domain interplay or also referred to as domain co-operativity studies. By way of example, molecular replacement may be used. In this method, unknown domain co-operativity with N-domain of ACE protein, N-domain of ACE protein mutant, N-domain of ACE protein variant, N-domain of ACE protein homologue (e.g. another protein with significant amino acid sequence homology to the N-domain of ACE protein), N-domain of ACE protein derivative, N-domain of ACE protein fragments or N-domain of ACE protein complex may be determined using the N-domain of ACE protein structure co-ordinates of the present invention. This method will provide a more accurate structural form for the unknown crystal more quickly and efficiently than attempting to determine such information ab initio.

As used herein the term "domain co-operativity" refers to the capacity of each of the domains of ACE protein to modulate the biochemical activities of each other. As used herein the term "modulate" means to affect, to vary, to adjust, to increase, to decrease or generally to be able to regulate or modify the biochemical activity of the N- or C-domain of ACE ptoein.

Preferably the structural co-ordinates of N-domain of ACE protein are used to study co-operativity between the N-domain of ACE protein and the C-domain of ACE protein.

In a preferred embodiment of the present invention, the crystal of the N-domain of ACE protein further comprises a ligand bound to the ACE protein or a portion thereof. For example, the N-domain of ACE protein may be crystallised in a complex with a ligand that is an inhibitor of the N-domain of ACE protein e.g. lisinopril, captopril or RXP407.

By way of example the inhibitor is bound to the N-domain of ACE protein or a portion thereof by contacting one of more residues of the N-domain (SEQ ID NO: 1) of ACE protein selected from: Gln259, Tyr369, Lys489 and Tyr498.

The crystal structures of a series of such complexes may then be solved by molecular replacement or in combination with MAD (Multiwavelength Anomalous Dispersion) and/or MIRAS (Multiple Isomorphous Replacement with Anomalous Scattering) procedures—and compared with that of minimally glycosylated N-domain of ACE protein. Potential sites for modification within the binding sites of the N-domain may thus be identified. This information provides an additional tool for determining the most efficient binding interactions, for example, increased hydrophobic interactions, between the N-domain of ACE protein and a ligand or a compound.

The information will also provide ideal conditions for designing domain specific inhibitors to more precisely regulate the biochemical functions of the N- and C-domains of ACE protein.

The structures and complexes of the N-domain of ACE protein may be refined using computer software—such as X-PLOR (*Meth. Enzymol*., vol. 114 & 115, H. W. Wyckoff et al., eds., Academic Press (1985)), MLPHARE (Collaborative computational project Number 4. The CCP4 Suite: Programs for Protein Crystallography (1994) *Acta Crystallogr. D* 50, 760-763) and SHARP [De La Fortelle, E. & Bricogne, G. Maximum-likelihood heavy-atom parameters refinement in the MIR and MAD methods (1997) *Methods Enzymol.* 276, 472-494). Preferably, the complexes are refined using the program CNS (Brünger et al., (1998) *Acta Crystallogr*. D 54, 905-921). During the final stages of refinement water molecules, ions and inhibitor molecules may be inserted in the structure. This information may thus be used to optimise known classes of modulators of the N-domain of ACE protein, eg. inhibitors, and more importantly, to design and synthesise novel classes of domain specific modulators.

The overall figure of merit may be improved by iterative solvent flattening, phase combination and phase extension with the program SOLOMON (Abrahams, J. P. & Leslie, A. G. W. Methods used in structure determination of bovine mitochondrial F1 ATPase. (1996) *Acta Crystallogr*. D 52, 110-119).

The structure co-ordinates of the mutants of the N-domain of ACE provided in this invention also facilitate the identification of related domains or enzymes analogous to the N-domain of ACE protein in function, structure or both, thereby further leading to novel therapeutic modes for treating or preventing ACE related diseases.

The design of compounds that bind to or modulate the N-domain of ACE protein or the C-domain of ACE protein according to the present invention generally involves consideration of two factors.

First, the compound must be capable of physically and structurally associating with the N-domain or the C-domain of ACE protein. Non-covalent molecular interactions important in the association of the N-domain of ACE with its substrate may include hydrogen bonding, van der Waals and hydrophobic interactions.

Second, the compound must be able to assume a conformation that allows it to associate with the N-domain or C-domain of ACE protein. Although certain portions of the compound may not directly participate in the association with the N-domain or C-domain of ACE, those portions may still influence the overall conformation of the molecule. This may have a significant impact on potency of the compound. Such conformational requirements include the overall three-dimensional structure and orientation of the chemical ligand or compound in relation to all or a portion of a binding site of the N-domain or C-domain of ACE, or the spacing between functional groups of a compound comprising several chemical entities that directly interact with the N-domain or C-domain of ACE.

The potential modulating or binding effect of a chemical compound on the N-domain or the C-domain of ACE may be analysed prior to its actual synthesis and testing by the use of computer modelling techniques. If the theoretical structure of the given compound suggests insufficient interaction and association with the N-domain or the C-domain of ACE, then synthesis and testing of the compound may be obviated. However, if computer modelling indicates a strong interaction, the molecule may be synthesised and tested for its ability to bind to the N-domain or the C-domain of ACE and modulate (e.g. inhibit) using the fluorescent substrate assay of Thornberry et al., (2000) *Methods Enzymol.* 322, 100-110. In this manner, synthesis of inactive compounds may be avoided.

A modulating or other binding compound of the N-domain or the C-domain of ACE may be computationally evaluated and designed by means of a series of steps in which chemical entities or test compounds are screened and selected for their ability to associate with the N-domain or the C-domain of ACE.

A person skilled in the art may use one of several methods to screen chemical entities or test compounds for their ability to associate with the N-domain or the C-domain of ACE and more particularly with the individual binding sites of the N-domain or the C-domain of ACE. This process may begin by visual inspection of, for example, the active site on the computer screen based on the N-domain or the C-domain of ACE co-ordinates of the present invention. Selected chemical entities or test compounds may then be positioned in a variety of orientations, or docked, with the N-domain or the C-domain of ACE. Docking may be accomplished using software such as Quanta and Sybyl, followed by energy minimisation and molecular dynamics with standard molecular mechanics force fields—such as CHARMM and AMBER.

Specialised computer programs may also assist in the process of selecting chemical entities or test compounds. These include but are not limited to MCSS (Miranker and Karplus (1991) *Proteins: Structure, Function and Genetics,* 11, 29-34); GRID (Goodford (1985) *J. Med. Chem.,* 28, 849-857) and AUTODOCK (Goodsell and Olsen (1990), *Proteins: Structure. Function, and Genetics,* 8, 195-202).

Once suitable chemical entities or test compounds have been selected, they may be assembled into a single compound capable of modulating the domains of the ACE protein e.g. the N-domain and/or the C-domain of the ACE protein. Assembly may proceed by visual inspection of the relationship of the chemical entities or test compounds in relation to the structure co-ordinates of the N-domain of ACE protein. This may be followed by manual model building using software—such as Quanta, Sybyl or O [Jones, T. A., Zou, J. Y., Cowan, S. W. & Kjeldgaard, M. Improved methods for building protein models in electron density maps and the location of errors in these models (1991) *Acta Crystallogr*. A 47, 110-119].

Refinement of the model may be carried out using the program CNS [Brünger, A. T. et al., Crystallography & NMR System: A new software suite for macromolecular structure determination. (1998) *Acta Crystallogr*. D 54, 905-921].

Various programs may be used by a skilled person to connect the individual chemical entities or test compounds—such as 3D Database systems (Martin (1992) *J. Med. Chem.,* 35, 2145-2154) and CAVEAT (Bartlett et al., (1989) *Royal Chem. Soc.* 78, 182-196).

Rather than build an inhibitor of the N-domain or the C-domain of ACE protein one chemical ligand at a time, modelling of other N-domain or C-domain binding compounds may be designed as a whole or de novo using either an empty binding site or optionally including some portion(s) of a known inhibitor(s). Such compounds may be designed using programs that may include but are not limited to LEGEND (Nishibata and Itai (1991) Tetrahedron, 47, 8985) and LUDI (Bohm (1992) *J. Comp. Aid. Molec. Design,* 6, 61-78). Other molecular modelling techniques may also be employed in accordance with this invention—such as those described by Cohen et al., *J. Med. Chem.,* 33, 883-894 (1990); Navia and Murcko (1992) *Current Opinions in Structural Biology,* 2, 202-210 (1992).

Once a compound has been designed or selected by the above methods, the efficiency with which that compound may bind to the N-domain or the C-domain of ACE protein may be computationally evaluated. Specific computer software may be used to evaluate the efficiency of binding (eg. to evaluate compound deformation energy and electrostatic interaction)—such as QUANTA/CHARMM (Accelrys Inc., USA) and Insight II/Discover (Biosym Technologies Inc., San Diego, Calif., USA). These programs may be implemented, for instance, using a suitable workstation. Other hardware systems and software packages will be known to those persons skilled in the art.

Once a modulating compound has been selected or designed, as described above, substitutions may be made (eg. in atoms or side groups) to improve or modify the binding properties. The substitutions may be conservative i.e. the replacement group may have approximately the same size, shape, hydrophobicity and charge as the original group. Such substituted chemical compounds may then be analysed for efficiency of binding to the N-domain or C-domain of ACE by the same computer methods described above.

Test compounds and modulators of the N-domain or C-domain of ACE protein which are identified using the crystal and the methods of the present invention may be screened in assays. Screening can be, for example in vitro, in cell culture, and/or in vivo. Biological screening assays preferably centre on activity-based response models, binding assays (which measure how well a compound binds), and bacterial, yeast and animal cell lines (which measure the biological effect of a compound in a cell). The assays can be automated for high capacity-high throughput screening (HTS) in which large numbers of compounds can be tested to identify compounds with the desired activity.

Current screening technologies are described in Handbook of Drug Screening, edited by Ramakrishna Seethala, Prabhavathi B. Fernandes. New York, N.Y., Marcel Dekker, (2001).

Disorders

These include, but are not limited to, treatment of high blood pressure; treatment of heart failure; prolonging survival of patients who have had a heart attack; preventing death by heart attack and stroke in patients with vascular disease and in diabetics with other vascular risk factors; prolonging survival of patients with weak heart muscle; helping leaking heart valves; preserving kidney function in diabetics; and the treatment of new indications (e.g. polycythemia). Special groups of patients may also be treated with N-domain or C-domain of ACE inhibitors, including patients with chronic pulmonary disease, patients with schleroderma, patients with atheroschlerosis, and patients with hyperuricemia.

It is also envisaged that the modulators identified by the methods described herein may be used to treat Alzheimer's disease and other degenerative diseases, conditions or disorders of the CNS.

ACE Constructs

The N-domain of ACE protein produced by a host recombinant cell may be secreted or may be contained intracellularly depending on the nucleotide sequence and/or the vector used.

The skilled person would understand that expression vectors containing the N-domain of ACE protein encoding nucleotide sequence or a mutant, variant, homologue, derivative or fragment thereof, may be designed with signal sequences which direct secretion of the N-domain of ACE protein coding sequences across a particular prokaryotic or eukaryotic cell membrane.

The N-domain encoding sequence may be fused (e.g. ligated) to nucleotide sequences encoding a polypeptide domain which will facilitate purification of soluble proteins (Kroll D J et al., (1993) *DNA Cell Biol* 12:441-53). Preferably, the polypeptide domain which facilitates purification of soluble proteins is fused in frame with the N-domain of the ACE protein encoding sequence. Such purification facilitating domains include, but are not limited to, metal chelating peptides—such as histidine-tryptophan modules that allow purification on immobilised metals (Porath J (1992) *Protein Expr Purif* 3, 263-281), protein A domains that allow purification on immobilised immunoglobulin, and the domain utilised in the FLAGS extension/affinity purification system (Immunex Corp, Seattle, Wash.). The inclusion of a cleavable linker sequence such as Factor XA or enterokinase (Invitrogen, San Diego, Calif.) between the purification domain and ACE is useful to facilitate purification.

Preferably the N-domain of ACE protein sequence is fused with the glutathione synthetase (GS) signal.

Preferably, the N-domain of ACE protein is secreted in a soluble form host cells and can be harvested from the growth medium.

Preferably, the N-domain of ACE construct is pEE14 N-domain which encodes the N-domain of human tACE (SEQ ID NO: 2). This construct comprises the inter-domain linker region.

Host Cell

As used herein, the term "host cell" refers to any cell that comprises nucleotide sequences that are of use in the present invention, for example, nucleotide sequences encoding the N-domain of ACE protein.

Host cells may be transformed or transfected with a nucleotide sequence contained in a vector e.g. a cloning vector. Preferably, said nucleotide sequence is carried in a vector for the replication and/or expression of the nucleotide sequence. The cells will be chosen to be compatible with the said vector and may for example be prokaryotic such as bacterial or eukaryotic such as fungal, yeast or plant cells.

The gram-negative bacterium *E. coli* is widely used as a host for cloning nucleotide sequences. This organism is also widely used for heterologous nucleotide sequence expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide and/or the desirability for further processing of the expressed protein, eukaryotic hosts including yeast or other fungi may be preferred.

In general, yeast cells are preferred over fungal cells because yeast cells are easier to manipulate. However, some proteins are either poorly secreted from the yeast cell, or in some cases are not processed properly (e.g. hyperglycosylation). In these instances, a different fungal host organism should be selected.

Examples of expression hosts are fungi—such as *Aspergillus* species (such as those described in EP-A-0184438 and EP-A-0284603) and *Trichoderma* species; bacteria—such as *Bacillus* species (such as those described in EP-A-0134048 and EP-A-0253455), *Streptomyces* species and *Pseudomonas* species; yeast—such as *Kluyveromyces* species (such as those described in EP-A-0096430 and EP-A-0301670) and *Saccharomyces* species; mammalian cells—such as CHO-K1 cells.

The use of host cells may provide for post-translational modifications (e.g. glycosylation) as may be needed to confer optimal biological activity on recombinant expression products of the present invention.

Aspects of the present invention also relate to host cells comprising the N-domain of ACE protein constructs of the present invention. The N-domain of ACE protein constructs may comprise a nucleotide sequence for replication and expression of the sequence. The cells will be chosen to be compatible with the vector and may for example be prokaryotic such as bacterial or eukaryotic such as fungal, yeast or plant cells.

In a preferred embodiment, the host cells are mammalian cells—such as CHO-K1 cells. CHO-K1 cells expressing the N-domain of ACE protein may be grown and maintained in accordance with Yu et al. (1997).

Nucleotide Sequences

As used herein, the term "nucleotide sequence" refers to nucleotide sequences, oligonucleotide sequences, polynucleotide sequences and variants, homologues, fragments and derivatives thereof (such as portions thereof) which comprise the nucleotide sequences encoding the N-domain of ACE protein, for example, the N-domain of testis ACE protein (SEQ ID NO: 2) or the N-domain (SEQ ID NO: 1) of somatic ACE protein.

The nucleotide sequence may be DNA or RNA of genomic or synthetic or recombinant origin, which may be double-stranded or single-stranded whether representing the sense or antisense strand or combinations thereof.

Preferably, the term nucleotide sequence is prepared by use of recombinant DNA techniques (e.g. recombinant DNA). The nucleotide sequences may include within them synthetic or modified nucleotides. A number of different types of modification to oligonucleotides are known in the art. These include methylphosphonate and phosphorothioate backbones addition of acridine or polylysine chains at the 3' and/or 5' ends of the molecule. For the purposes of the present invention, it is to be understood that the nucleotide sequences described herein may be modified by any method available in the art.

It will be understood by a skilled person that numerous different nucleotide sequences can encode the same protein as a result of the degeneracy of the genetic code. In addition, it is to be understood that skilled persons may, using routine techniques, make nucleotide substitutions that do not substantially affect the activity encoded by the nucleotide sequence of the present invention to reflect the codon usage of any particular host organism in which the target is to be expressed.

The terms "variant", "homologue" or "derivative" in relation to nucleotide sequences include any substitution of, variation of, modification of, replacement of, deletion of or addition of one (or more) nucleic acid from or to the sequence providing the resultant nucleotide sequence encodes a functional protein according to the present invention (or even a modulator of the N-domain of ACE protein according to the present invention if said modulator comprises a nucleotide sequence).

Amino Acid Sequences

As used herein, the term "amino acid sequence" is synonymous with the term "polypeptide" and/or the term "protein". In some instances, the term "amino acid sequence" is synonymous with the term "peptide".

Aspects of the present invention concern the use of amino acid sequences, which may be available in databases. These amino acid sequences may comprise N-domain of ACE proteins.

The amino acid sequence may be isolated from a suitable source, or it may be made synthetically or it may be prepared by use of recombinant DNA techniques.

The terms "variant", "homologue" or "derivative" in relation to amino acid sequences include any substitution of, variation of, modification of, replacement of, deletion of or addition of one (or more) amino acid from the functional protein according to the present invention (or even a modulator of the N-domain of ACE protein according to the present invention if said modulator comprises an amino acid sequence).

Preferably, the N-domain of ACE protein comprises SEQ ID NO: 1 or a mutant, variant, homologue, derivative or a fragment thereof.

Purity

Preferably the protein solution used for crystallisation is at least 95.5% pure. More preferably the protein solution used for crystallisation is at least 97.5% pure. More preferably, the protein solution used for crystallisation is at least 99.0% pure. Most preferably, the protein solution used for crystallisation is at least 99.5% pure.

Model

As used herein, the term "model" refers to a structural model such as a three dimensional (3D) structural model (or representation thereof) comprising the N-domain of ACE protein.

Test compounds can be modelled that bind spatially and preferentially to the N-domain of ACE protein—such as to bind spatially and preferentially to the N-domain of ACE protein—for example, the active site of the N-domain of ACE protein.

Preferably, the crystal model comprising the N-domain of ACE is built from all or a portion of the structural co-ordinates set forth in Table A (SEQ ID NOs: 5 and 6) or Table B (SEQ ID NOs: 7 and 8).

Mutant

As used herein, the term "mutant" refers to the N-domain of ACE protein comprising any one or more changes in the wild-type ACE sequence shown as SEQ ID NO: 1.

The term "mutant" is not limited to any of the mutations described herein which are reflected in amino acid substitutions of the amino acid residues in the N-domain of ACE protein, but are not limited to, other deletions or insertions of nucleotides which may result in changes in the amino acid residues in the amino acid sequence of the N-domain of ACE protein.

The present invention also enables the solving of the crystal structure of mutants of the N-domain of ACE protein. More particularly, by virtue of the present invention, the location of the active site of the N-domain of ACE protein based on its crystal structure permits the identification of desirable sites for mutation. For example, one or more mutations may be directed to a particular site—such as the active site—or combination of sites. Similarly, only a location on, at or near the inter-domain linker region may be replaced, resulting in an altered domain co-operativity by changing the charge of one or more charge units, as compared to the wild-type N-domain. Alternatively, an amino acid residue in the inter-domain linker region of the N-domain of ACE may be chosen for replacement based on its hydrophilic or hydrophobic characteristics.

Such mutants may be characterised by any one of several different properties as compared with wild-type N-domain of ACE protein. For example, such mutants may have altered surface charge of one or more charge units, or have an increased stability to subunit dissociation, or an altered substrate specificity in comparison with, or a higher specific activity than, wild-type of the N-domain of ACE protein.

The mutants may be prepared in a number of ways that are known by a person skilled in the art. For example, mutations may be introduced by means of oligonucleotide-directed mutagenesis or other conventional methods. Alternatively, mutants of the N-domain of ACE protein may be generated by site specific replacement of a particular amino acid with an unnaturally occurring amino acid. This may be achieved by growing a host organism capable of expressing either the wild-type or mutant polypeptide on a growth medium depleted of one or more natural amino acids but enriched in one or more corresponding unnaturally occurring amino acids.

The expression, activity (e.g. kinetic constants) and/or the crystallisation properties of the mutants may be determined using the methods described herein.

Variants/Homologues/Derivatives/Fragments

The N-domain of ACE protein described herein is intended to include any polypeptide, which has the activity of the naturally occurring N-domain and includes all vertebrate and mammalian forms. Such terms also include polypeptides that differ from naturally occurring forms of the N-domain by having amino acid deletions, substitutions, and additions, but which retain the activity of the N-domain of ACE protein.

The term "variant" is used to mean a naturally occurring polypeptide or nucleotide sequences which differs from a wild-type or a native sequence.

The term "fragment" indicates that a polypeptide or nucleotide sequence comprises a fraction of a wild-type or a native sequence. It may comprise one or more large contiguous sections of sequence or a plurality of small sections. The sequence may also comprise other elements of sequence, for example, it may be a fusion protein with another protein. Preferably the sequence comprises at least 50%, more preferably at least 65%, more preferably at least 80%, most preferably at least 90% of the wild-type sequence.

The present invention also encompasses the use of variants, homologues and derivatives of nucleotide and amino acid sequences. Here, the term "homologue" means an entity having a certain homology with amino acid sequences or nucleotide sequences. Here, the term "homology" can be equated with "identity".

In the present context, a homologous sequence is taken to include an amino acid sequence which may be at least 75%, 85% or 90% identical, preferably at least 95% or 98% identical to the subject sequence. Although homology can also be considered in terms of similarity (i.e. amino acid residues having similar chemical properties/functions), it is preferred here to express homology in terms of sequence identity.

Homologous sequence is taken to include a nucleotide sequence which may be at least 75%, 85% or 90% identical, preferably at least 95% or 98% identical to the subject sequence.

Homology comparisons can be conducted by eye, or more usually, with the aid of readily available sequence comparison programs. These commercially available computer programs can calculate % homology between two or more sequences.

Homology when based on percentage (%) may be calculated over contiguous sequences, i.e. one sequence is aligned with the other sequence and each amino acid in one sequence is directly compared with the corresponding amino acid in the other sequence, one residue at a time. This is usually referred to "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, *Nucleic Acids Research* 12:387). Examples of other software than can perform sequence comparisons include, but are not limited to, the BLAST package (see Ausubel et al., 1999 ibid—Chapter 18), FASTA (Atschul et al., 1990, *J. Mol. Biol.,* 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see *FEMS Microbiol Lett* 1999 174(2): 247-50; *FEMS Microbiol Lett* 1999 177(1): 187-8)

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

By way of example, homologous sequences of the N-domain of ACE protein include, but are not limited to human $ACE_s$ somatic ACE (accession number: J04144), human $ACE_T$ testis ACE (accession number: M26657) (SEQ ID NO: 2), human ACEH/ACE2 (accession numbers: AAF78220; BAB40370; AAF99721) (SEQ ID NO: 3), chimp $ACE_T$ (accession number: AF193487_2), rabbit $ACE_T$ mature protein (accession number: P22968), rabbit $ACE_T$ full pre-protein (accession number: P22968), mouse $ACE_T$ testis ACE (accession number: P22967), bovine Cdom $ACE_s$ C-domain, rat Cdom $ACE_s$ C-domain (derived from accession number P47820; starting D616), human Ndom $ACE_s$ N-domain (SEQ ID NO: 1) (derived from accession number P12821 (J04144)), chimp Ndom $ACE_s$ N-domain (derived from accession number AF193487_1), rabbit Ndom $ACE_s$ N-domain (derived from P12822), bovine Ndom (Bovine {Bos taurus} $ACE_s$ N-domain), mouse Ndom $ACE_s$ N-domain (derived from accession number P09470), rat Ndom $ACE_s$ N-domain (derived from accession number P47820), chick ACE (partial ACE accession number Q10751), dros AnCE (derived from accession number Q10714), dros ACEr (derived from accession number X96913), buffalo fly ACE (derived from accession number Q10715), and silkworm ACE (derived from accession number BAA97657), tick ACE (derived from accession number U62809).

The sequences may also have deletions, insertions or substitutions of amino acid residues, which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

The term "derivative" or "derivatised" as used herein includes chemical modification of a ligand—such as test compound or a modulator of the N-domain of ACE protein. Illustrative of such chemical modifications would be replacement of hydrogen by a halo group, an alkyl group, an acyl group or an amino group.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol*. (1995) 13(4), 132-134.

Test Compound

As used herein, the term "test compound" includes, but is not limited to, a compound which may be obtainable from or produced by any suitable source, whether natural or not.

The test compound may be designed or obtained from a small molecule library of compounds, which may comprise peptides, as well as other compounds, such as small organic molecules and particularly new lead compounds. By way of example, the test compound may be a natural substance, a biological macromolecule, or an extract made from biological materials—such as bacteria, fungi, or animal (particularly mammalian) cells or tissues, an organic or an inorganic molecule, a synthetic test compound, a semi-synthetic test compound, a structural or functional mimetic, a peptide, a peptidomimetics, a derivatised test compound, a peptide cleaved from a whole protein, or a peptide synthesised synthetically (such as, by way of example, either using a peptide synthesiser or by recombinant techniques or combinations thereof, a recombinant test compound, a natural or a non-natural test compound, a fusion protein or equivalent thereof and mutants, derivatives or combinations thereof. The test compound may even be a compound that is a modulator of the N-domain or C-domain of ACE protein—such as a known inhibitor of the N-domain or C-domain of ACE protein—that has been modified in some way e.g. by recombinant DNA techniques or chemical synthesis techniques.

Typically, the test compound will be prepared by recombinant DNA techniques and/or chemical synthesis techniques.

Once a test compound capable of interacting with the N-domain or C-domain of ACE protein has been identified, further steps may be carried out to select and/or to modify the test compounds and/or to modify existing compounds, such that they are able to modulate the N-domain or C-domain of ACE protein.

The present invention also relates to a test compound which may be a domain specific compound such as a domain specific inhibitor capable of modulating the activity of the ACE protein in a domain specific manner. That is the compound is capable of modulating the N-domain and/or C-domain of ACE protein.

Modulating the Activity of ACE

As herein, the term "modulating" refers to preventing, suppressing, inhibiting, alleviating, restoring, elevating, increasing or otherwise affecting the N-domain or C-domain of ACE protein.

The term "modulator of N-domain or C-domain of ACE" may refer to a single ligand or a combination of ligands.

The modulator of the N-domain or C-domain of ACE protein may be an antagonist or an agonist of the N-domain or the C-domain of ACE.

As used herein, the term "agonist" means any ligand, which is capable of interacting (e.g. binding) with N-domain or C-domain of ACE protein and which is capable of increasing a proportion of the N-domain or C-domain of ACE that is in an active form, resulting in an increased biological response.

As used herein, the term "antagonist" means any ligand, which is capable of interacting (e.g. binding) with N-domain or C-domain of ACE protein and which is capable of decreasing (eg. inhibiting) a proportion of the N-domain or C-domain of ACE that is in an active form, resulting in a decreased biological response.

Preferably, the modulators of the N-domain or C-domain of ACE protein of the present invention are antagonists of the N-domain or C-domain of ACE protein.

The modulator may be an organic compound or other chemical. The modulator may be a compound, which is obtainable from or produced by any suitable source, whether natural or artificial. The modulator may be an amino acid molecule, a polypeptide, or a chemical derivative thereof, or a combination thereof. The modulator may even be a polynucleotide molecule—which may be a sense or an anti-sense molecule. The modulator may even be an antibody.

The modulator of the N-domain or C-domain of ACE protein may be designed or obtained from a small molecule library of compounds, which may comprise peptides, as well as other compounds or small organic molecules.

By way of example, the modulator of the N-domain or C-domain of ACE protein may be a natural substance, a biological macromolecule, or an extract made from biological materials such as bacteria, fungi, or animal (particularly mammalian) cells or tissues, an organic or an inorganic molecule, a synthetic agent, a semi-synthetic agent, a structural or functional mimetic, a peptide, a peptidomimetic, a derivatised agent, a peptide cleaved from a whole protein, or a peptide synthesised synthetically (such as, by way of example, either using a peptide synthesiser or by recombinant techniques or combinations thereof, a recombinant agent, an antibody, a natural or a non-natural agent, a fusion protein or equivalent thereof and mutants, derivatives or combinations thereof).

Typically, the modulator of the N-domain or C-domain of ACE protein will be an organic compound. Typically, the organic compounds will comprise two or more hydrocarbyl groups. Here, the term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. For some applications, preferably the modulator of the N-domain or C-domain of ACE protein comprises at least one cyclic group. The cyclic group may be a polycyclic group, such as a non-fused polycyclic group. For some applications, the modulator of the N-domain or C-domain of ACE protein comprises at least the one of said cyclic groups linked to another hydrocarbyl group.

The modulator of the N-domain or C-domain of ACE protein may contain halo groups, for example, fluoro, chloro, bromo or iodo groups.

The modulator of the N-domain or C-domain of ACE protein may contain one or more of alkyl, alkoxy, alkenyl, alkylene and alkenylene groups—which may be unbranched- or branched-chain.

The modulator of the N-domain or C-domain of ACE protein may be in the form of a pharmaceutically acceptable salt—such as an acid addition salt or a base salt—or a solvate thereof, including a hydrate thereof. For a review on suitable salts see Berge et al., (1977) *J. Pharm. Sci.* 66, 1-19.

The modulator of the N-domain or C-domain of ACE protein may be a structurally novel modulator.

The modulators of the N-domain or C-domain of ACE protein may be analogues to other known modulators—such as known inhibitors of the N-domain of ACE protein (for example, snake venom, peptides produced by enzymatic hydrolysis of casein or fish meat protein, or Benazepril, Captopril, Cilazapril, Enalapril, Fosinopril, Lisinopril, Moexipril, Perindopril, Quinapril, Ramipril, Trandolapril and Enalaprilat).

Preferably the inhibitor of the N-domain or C-domain of ACE protein is Lisinopril (N2-[(S)-1-carboxy-3-phenylpropyl]-L-lysyl-L-proline; also known as Prinivil or Zestril).

Preferably, the N-domain or C-domain of ACE protein modulators have improved properties over those previously available, for example, fewer side effects—such as cough (e.g. dry, persistent); fever and chills; hoarseness; swelling of face, mouth, hands, or feet; trouble in swallowing or breathing; itching of skin; yellow eyes or skin; dizziness, light-headedness, or fainting; skin rash, with or without itching; fever, or joint pain; abdominal pain, abdominal distention; nausea, or vomiting; chest pain, confusion; irregular heartbeat; nervousness; numbness or tingling in hands, feet, or lips; weakness or heaviness of legs; headache, diarrhoea; loss of taste; nausea; unusual tiredness and angioedema.

The modulator of the N-domain or C-domain of ACE protein may be a mimetic.

The modulator of the N-domain or C-domain of ACE protein may also be chemically modified.

The modulator of the N-domain or C-domain of ACE protein may be capable of displaying other therapeutic properties.

The modulator of the N-domain or C-domain of ACE protein may be used in combination with one or more other pharmaceutically active agents.

If combinations of active agents are administered, then these may be administered simultaneously, separately or sequentially.

Mimetic

As used herein, the term "mimetic" relates to any chemical including, but not limited to, peptide, polypeptide, antibody or other organic chemical with the same qualitative activity or effect as a known compound. That is, the mimetic is a functional equivalent of a known compound.

Stereo and Geometric Isomers

Modulators of the N-domain or C-domain of ACE protein may exist as stereoisomers and/or geometric isomers—e.g. they may possess one or more asymmetric and/or geometric centres and so may exist in two or more stereoisomeric and/or geometric forms. The present invention contemplates the use of all of the individual stereoisomers and geometric isomers, and mixtures thereof.

Pharmaceutical Salt

Modulators of the N-domain or C-domain of ACE protein may be administered in the form of a pharmaceutically acceptable salt.

Pharmaceutically-acceptable salts are well known to those skilled in the art, and for example include those mentioned by Berge et al., (1977) *J. Pharm. Sci.,* 66, 1-19. Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate and p-toluenesulphonate salts.

When one or more acidic moieties are present, suitable pharmaceutically acceptable base addition salts can be formed from bases which form non-toxic salts and include the aluminium, calcium, lithium, magnesium, potassium, sodium, zinc, and pharmaceutically-active amines such as diethanolamine, salts.

A pharmaceutically acceptable salt of a modulator of the N-domain or C-domain of ACE protein may be readily prepared by mixing together solutions of the modulator and the desired acid or base, as appropriate. The salt may precipitate from solution and be collected by filtration or may be recovered by evaporation of the solvent.

The modulator of the N-domain or C-domain of ACE protein may exist in polymorphic form.

The modulator of the N-domain or C-domain of ACE protein may contain one or more asymmetric carbon atoms and therefore exists in two or more stereoisomeric forms. Where a modulator of the N-domain or C-domain of ACE protein contains an alkenyl or alkenylene group, cis (E) and trans (Z) isomerism may also occur. The present invention includes the individual stereoisomers of the modulator of the N-domain or C-domain of ACE protein and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of the modulator of the N-domain or C-domain of ACE protein or a suitable salt or derivative thereof. An individual enantiomer of the modulator of the N-domain or C-domain of ACE may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The modulator of the N-domain or C-domain of ACE may also include all suitable isotopic variations of the modulator or a pharmaceutically acceptable salt thereof. An isotopic variation of an modulator of the N-domain or C-domain of ACE or a pharmaceutically acceptable salt thereof is defined as one in which at least one atom is replaced by an atom having the same atomic number but an atomic mass different from the atomic mass usually found in nature. Examples of isotopes that can be incorporated into the modulator of ACE and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the modulator the N-domain or C-domain of ACE and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the modulator of the N-domain or C-domain of ACE and pharmaceutically acceptable salts thereof of this invention can generally be prepared by conventional procedures using appropriate isotopic variations of suitable reagents.

It will be appreciated by those skilled in the art that the agent may be derived from a prodrug. Examples of prodrugs include entities that have certain protected group(s) and which may not possess pharmacological activity as such, but may, in certain instances, be administered (such as orally or parenterally) and thereafter metabolised in the body to form the modulator of the N-domain or C-domain of ACE which is pharmacologically active.

It will be further appreciated that certain moieties known as "pro-moieties", for example as described in "Design of Prodrugs" by H. Bundgaard, Elsevier, 1985 (the disclosured of which is hereby incorporated by reference), may be placed on appropriate functionalities of the modulator of the N-domain or C-domain of ACE protein. Such prodrugs are also contemplated within the scope of the invention.

Pharmaceutically Active Salt

The modulator of the N-domain or C-domain of ACE protein may be administered as a pharmaceutically acceptable salt. Typically, a pharmaceutically acceptable salt may be readily prepared by using a desired acid or base, as appropriate. The salt may precipitate from solution and be collected by filtration or may be recovered by evaporation of the solvent.

Chemical Synthesis Methods

The modulator of the N-domain or C-domain of ACE protein of the present invention may be prepared by chemical synthesis techniques.

It will be apparent to those skilled in the art that sensitive functional groups may need to be protected and deprotected during synthesis of a compound of the invention. This may be achieved by conventional techniques, for example as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

It is possible during some of the reactions that any stereocentres present could, under certain conditions, be racemised, for example if a base is used in a reaction with a substrate having an having an optical centre comprising a base-sensitive group. This is possible during e.g. a guanylation step. It should be possible to circumvent potential problems such as this by choice of reaction sequence, conditions, reagents, protection/deprotection regimes, etc. as is well-known in the art.

The compounds and salts may be separated and purified by conventional methods.

Separation of diastereomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base.

The N-domain or C-domain of ACE protein, modulators of the N-domain or C-domain of ACE protein or variants, homologues, derivatives, fragments or mimetics thereof may be produced using chemical methods to synthesise the N-domain or C-domain of ACE protein or the modulator of the N-domain or C-domain of ACE protein in whole or in part. For example, the N-domain or C-domain peptide or a modulator of the N-domain or C-domain of ACE protein that is a peptide can be synthesised by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic peptides may be confirmed by amino acid analysis or sequencing (e.g., the Edman degradation procedure; Creighton, supra).

Synthesis of peptides (or variants, homologues, derivatives, fragments or mimetics thereof) may be performed using various solid-phase techniques (Roberge J Y et al (1995) Science 269: 202-204) and automated synthesis may be achieved, for example, using the ABI 43 1 A Peptide Synthesizer (Perkin Elmer) in accordance with the instructions provided by the manufacturer. Additionally, the amino acid sequences comprising the modulator of the N-domain or C-domain of ACE protein, may be altered during direct synthesis and/or combined using chemical methods with a sequence from other subunits, or any part thereof, to produce a variant modulator of the N-domain or C-domain of ACE protein.

Chemical Modification

The modulator of the N-domain or C-domain of ACE protein may be a chemically modified modulator.

The chemical modification of a modulator of the N-domain or C-domain of ACE protein may either enhance or reduce interactions between the modulator of the N-domain or C-domain of ACE protein and the target—such as hydrogen bonding interactions, charge interactions, hydrophobic interactions, van der Waals interactions or dipole interactions.

In one aspect, the modulator of the N-domain or C-domain of ACE protein may act as a model (for example, a template) for the development of other compounds.

Pharmaceutical Compositions

The components may be administered alone but will generally be administered as a pharmaceutical composition—e.g. when the components are in a mixture with a suitable pharmaceutical excipient, diluent or carrier selected with regard to the intended route of administration and standard pharmaceutical practice.

For example, the components can be administered in the form of tablets, capsules, ovules, elixirs, solutions or suspensions, which may contain flavouring or colouring agents, for immediate-, delayed-, modified-, sustained-, pulsed- or controlled-release applications.

If the pharmaceutical is a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders—such as polyvinylpyrrolidone, hydroxypropylmethylcellulose (HPMC), hydroxypropylcellulose (HPC), sucrose, gelatin and acacia. Additionally, lubricating agents—such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the modulator of the N-domain or C-domain of ACE protein may be combined with various sweetening or flavouring agents, colouring matter or dyes, with emulsifying and/or suspending agents and with diluents such as water, ethanol, propylene glycol and glycerin, and combinations thereof.

The routes for administration (delivery) may include, but are not limited to, one or more of oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intraventricular, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

Pharmaceutical compositions of the present invention may comprise a therapeutically effective amount of the N-domain of ACE protein, one or more modulators of the N-domain of ACE protein, one or more modulators of the C-domain of ACE protein or combinations thereof.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be administered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

If the modulator of the N-domain or C-domain of ACE protein is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions may be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or the pharmaceutical compositions can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The modulators of the N-domain or C-domain of ACE protein may be used in combination with a cyclodextrin. Cyclodextrin molecules are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

If the modulator of the N-domain or C-domain of ACE is a protein, then said protein modulator may be prepared in situ in the subject being treated. In this respect, nucleotide sequences encoding said protein may be delivered by use of non-viral techniques (e.g. by use of liposomes) and/or viral techniques (e.g. by use of retroviral vectors) such that the said protein is expressed from said nucleotide sequence.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

The modulators of the N-domain of ACE protein or the C-domain of ACE protein may be administered separately, concomitantly or sequentially.

Formulation

The component(s) may be formulated into a pharmaceutical composition, such as by mixing with one or more of a suitable carrier, diluent or excipient, by using techniques that are known in the art.

Vector

Aspects of the present invention relate to a vector comprising a nucleotide sequence—such as a nucleotide sequence encoding the N-domain or the C-domain of ACE protein or a modulator of the N-domain or the C-domain of ACE protein—administered to a subject.

Preferably, the N-domain or the C-domain of ACE and/or the modulator are prepared and/or delivered using a genetic vector.

It is well known in the art, that a vector is a tool that allows or facilitates the transfer of information from one environment to another. In accordance with the present invention, and by way of example, some vectors used in recombinant DNA techniques allow entities, such as a segment of DNA (such as a heterologous DNA segment, such as a heterologous cDNA segment), to be transferred into a host and/or a target cell for the purpose of replicating the vectors comprising nucleotide sequences and/or expressing the proteins encoded by the nucleotide sequences. Examples of vectors used in recombinant DNA techniques include, but are not limited to, plasmids, chromosomes, artificial chromosomes or viruses.

The term "vector" includes expression vectors such as transfection vectors, transduction vectors or transformation vectors.

The term "expression vector" means a construct capable of in vivo or in vitrolex vivo expression.

The terms "transfection vectors", "transduction vectors" or "transformation vectors" describe different constructs capable of being transferred from one organism to another of from one species to another.

Regulatory Sequences

In some applications, nucleotide sequences are operably linked to a regulatory sequence which is capable of providing for the expression of the nucleotide sequence, such as by a chosen host cell. By way of example, a vector comprising the N-domain or the C-domain of ACE nucleotide sequence is operably linked to such a regulatory sequence i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

Enhanced expression of a nucleotide sequence, for example, a nucleotide sequence encoding the N-domain or the C-domain of ACE protein—may also be achieved by the selection of heterologous regulatory regions, e.g. promoter, secretion leader and terminator regions, which serve to increase expression and, if desired, secretion levels of the protein of interest from the chosen expression host and/or to provide for the inducible control of the expression of the N-domain or the C-domain of ACE protein. In eukaryotes, polyadenylation sequences may be operably connected to the C-terminus of the nucleotide sequence of the N-domain or the C-domain of ACE protein.

Preferably, the N-domain or the C-domain of ACE protein nucleotide sequence is operably linked to at least a promoter.

Aside from the promoter native to the nucleotide sequence described herein, other promoters may be used to direct its expression. The promoter may be selected for its efficiency in directing the expression of the N-domain or the C-domain of ACE nucleotide sequence in the desired expression host.

In another embodiment, a constitutive promoter may be selected to direct the expression of the N-domain or the C-domain of ACE nucleotide sequence of the present invention. Such an expression construct may provide additional advantages since it circumvents the need to culture the expression hosts on a medium containing an inducing substrate.

Hybrid promoters may also be used to improve inducible regulation of the expression construct.

The promoter can additionally include features to ensure or to increase expression in a suitable host. For example, the features can be conserved regions such as a Pribnow Box or a TATA box. The promoter may even contain other sequences to affect (such as to maintain, enhance, decrease)

the levels of expression of the N-domain or C-domain of ACE nucleotide sequence. For example, suitable other sequences include the Shl-intron or an ADH intron. Other sequences include inducible elements—such as temperature, chemical, light or stress inducible elements. Also, suitable elements to enhance transcription or translation may be present.

Expression Vector

Preferably, nucleotide sequences—such as nucleotide sequences encoding the N-domain or C-domain of ACE or modulators of the N-domain or C-domain of ACE—are inserted into a vector that is operably linked to a control sequence that is capable of providing for the expression of the coding sequence by the host cell.

Nucleotide sequences produced by a host recombinant cell may be secreted or may be contained intracellularly depending on the sequence and/or the vector used. As will be understood by those of skill in the art, expression vectors can be designed with signal sequences, which direct secretion of the nucleotide sequence through a particular prokaryotic or eukaryotic cell membrane.

The expression vector may be pEE14 N-domain (SEQ ID NO: 4) which encodes the N-domain of human ACE and is truncated in the interdomain linker region.

Preferably, the expression vectors are stably expressed in CHO-K1 cells as described previously (Ehlers et al., (1996) *Biochemistry* 35, 9549-9559).

Fusion Proteins

The N-domain or C-domain of ACE protein or a modulator of the N-domain or C-domain of ACE protein may be expressed as a fusion protein to aid extraction and purification and/or delivery of the modulator of the N-domain or C-domain of ACE or the N-domain or C-domain of ACE protein to an individual and/or to facilitate the development of a screen for modulators of the N-domain or C-domain of ACE protein.

Examples of fusion protein partners include glutathione-S-transferase (GST), 6×His, GAL4 (DNA binding and/or transcriptional activation domains) and β-galactosidase.

It may also be convenient to include a proteolytic cleavage site between the fusion protein partner and the protein sequence of interest to allow removal of fusion protein sequences. Preferably, the fusion protein will not hinder the activity of the protein of interest.

The fusion protein may comprise an antigen or an antigenic determinant fused to the substance of the present invention. In this embodiment, the fusion protein may be a non-naturally occurring fusion protein comprising a substance, which may act as an adjuvant in the sense of providing a generalised stimulation of the immune system. The antigen or antigenic determinant may be attached to either the amino or carboxy terminus of the substance.

Organism

The term “organism” in relation to the present invention includes any organism that could comprise the N-domain or C-domain of ACE protein and/or modulators of the N-domain or C-domain of ACE protein. Examples of organisms may include mammals, fungi, yeast, plants or bacteria.

Preferably, the organism is as vertebrate or a mammal. More preferably, the organism is a human.

Transformation

As indicated earlier, the host organism can be a prokaryotic or a eukaryotic organism. Examples of suitable prokaryotic hosts include *E. coli* and *Bacillus subtilis*. Teachings on the transformation of prokaryotic hosts are well documented in the art, for example see Sambrook et al., (Molecular Cloning: A Laboratory Manual, 2nd edition, 1989, Cold Spring Harbor Laboratory Press) and Ausubel et al., Current Protocols in Molecular Biology (1995), John Wiley & Sons, Inc. Examples of suitable eukaryotic hosts include mammalian cells.

If a prokaryotic host is used then the nucleotide sequence—such as the N-domain of ACE nucleotide sequence—may need to be suitably modified before transformation—such as by removal of introns.

Thus, the present invention also relates to the transformation of a host cell with a nucleotide sequence—such as those coding for the N-domain or C-domain of ACE protein or a modulator of the N-domain or C-domain of ACE protein. Host cells transformed with the nucleotide sequence may be cultured under conditions suitable for the expression and recovery of the encoded protein from cell culture. The protein produced by a recombinant cell may be secreted or may be contained intracellularly depending on the sequence and/or the vector used. As will be understood by those of skill in the art, expression vectors containing coding sequences can be designed with signal sequences which direct secretion of the coding sequences through a particular prokaryotic or eukaryotic cell membrane. Other recombinant constructions may join the coding sequence to nucleotide sequence encoding a polypeptide domain, which will facilitate purification of soluble proteins (Kroll D J et al., (1993) *DNA Cell Biol* 12:441-53) e.g. 6-His or Glutathione-S-transferase.

Transfection

Vectors comprising for example, the nucleotide sequence coding for the N-domain or C-domain of ACE protein, may be introduced into host cells, for example, mammalian cells, using a variety of methods.

Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (*Nature Biotech.* (1996) 14, 556), multivalent cations such as spermine, cationic lipids or polylysine, 1, 2,-bis (oleoyloxy)-3-(trimethylammonio) propane (DOTAP)-cholesterol complexes (Wolff and Trubetskoy (1998) *Nature Biotech.* 16, 421) and combinations thereof.

Uptake of nucleic acid constructs by mammalian cells is enhanced by several known transfection techniques for example those including the use of transfection agents. Example of these agents include cationic agents (for example calcium phosphate and DEAE-dextran) and lipofectants (for example Lipofectam™ and Transfectam™). Typically, nucleic acid constructs are mixed with the transfection agent to produce a composition.

Such methods are described in many standard laboratory manuals—such as Sambrook et al., Molecular Cloning: A Laboratory Manual, 2d ed. (1989) Cold Spring Harbor Laboratory Press, Cold Spring Harbor, N.Y.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual, Second Edition, Books* 1-3, Cold Spring Harbor Laboratory Press; Ausubel, F. M. et al., (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques, John* Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

DESCRIPTION OF THE DRAWINGS

This patent or application file contains at least one drawing executed in color. Copies of this patent or patent application publication with color drawing(s) will be provided by the Office upon request and payment of the necessary fee.

Table 1. Crystallographic Data

Figure 1:
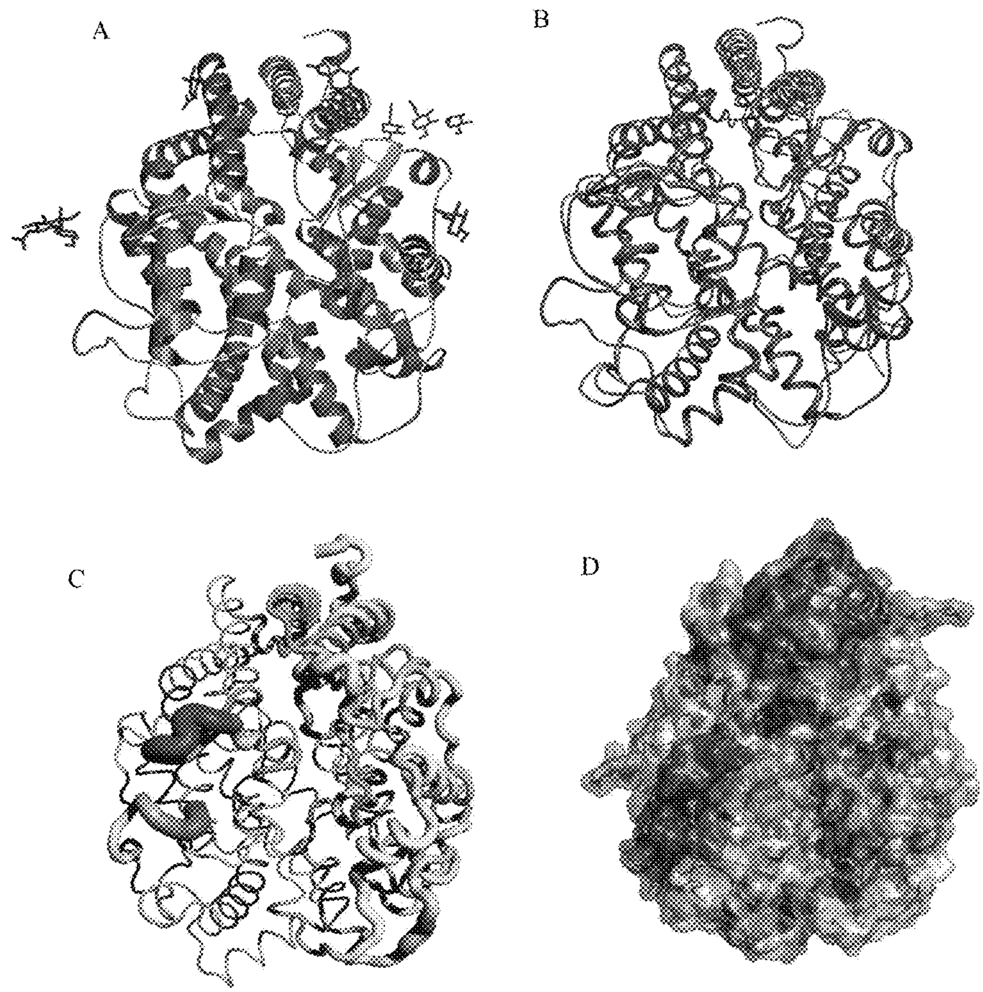
FIG. 1. (A) Overall structure of the N-domain (SEQ ID NO: 1) with the zinc ion in green, the chloride ion in red and the oligosaccharides in pink. (B) Superposition of the N-domain (SEQ ID NO: 1) (turquoise) and tACE (pink) (SEQ ID NO: 2) with the zinc ion in green. (C) Backbone coloured according to thermal vibration (B factor) with blue for the lowest B factors and red for the highest. (D) Surface diagram showing the lid (dark blue), N-linked glycans (green) and the protruding surface patch (pink) comprising the linker and the flexible loop.

Table 2. Active site residues that differ between the N (SEQ ID NO:1) and C domains (C domain numbering is as for tACE (SEQ ID NO: 2)).

Table A (SEQ ID NOs: 5 and 6). Structure co-ordinates of N-domain of ACE protein.

Table B (SEQ ID NOs: 7 and 8). Structure co-ordinates of N-domain of ACE protein complexed with lisinopril.

The invention will now be further described by way of Examples, which are meant to serve to assist one of ordinary skill in the art in carrying out the invention and are not intended in any way to limit the scope of the invention.

EXAMPLES

Example 1

Materials & Methods

Construction of Expression Vectors

An N-domain (SEQ ID NO: 4) construct (D629) cloned into the vector pECE (a kind gift from Sergei Danilov) and encoding the first 629 residues of somatic ACE, was subcloned into pBlueScript using the restriction endonucleases Xbal and EcoRI. The fragment was then sequenced to verify that the correct fragment was cloned. D629 was then again subcloned into pcDNA3.1(+) using the same restriction enzymes. This N-domain (SEQ ID NO: 4) construct was then introduced into the CHO cell glutamine synthetase (GS) expression vector pEE14 using the restriction endonucleases HindIII and XbaI. The identity of the construct and its correct orientation was confirmed via restriction enzyme digests and further sequencing. The new expression vector was termed pEE14 N-domain.

Cell Culture and Transfections

CHO-K1 cells were co-transfected with pEE14-N-domain (SEQ ID NO: 4) and pSV2neo (10:1). Geneticin (G418) (Sigma) resistant clones expressing soluble N-domain (SEQ ID NO: 4, residues 1-629) were further selected for resistance to methionine sulfoximine (MSX) (Yu et al., 1997). Cells stably expressing the N-domain were grown in Glasgow Minimum Essential Medium (GMEM) supplemented with 10% dialysed foetal calf serum (Gibco BRL) and 20 μM MSX. When confluent growth medium was changed to 1% dialysed FCS, 0.05% albumax I (Gibco BRL), 20 μM MSX and 1.5 mM N-butyldeoxynojirimycin (NB-DNJ) (Toronto Research Chemicals Inc.B691000 Lot 14-EG-91-1 and B691000 12-Cf-146-2).

Construct Purification

Medium containing recombinantly expressed soluble N-domain (N-domain (SEQ ID NO: 4, residues 1-629) of ACE protein) was harvested and purified in tandem over a protein-G Agarose (Sigma) column followed by an N-domain specific monoclonal antibody (5C5) protein G Agarose column. N-domain was eluted with 50 mM ethanolamine pH 11.5. The eluted solution was then dialysed against 5mM HEPES pH 7.5, 0.1 mM PMSF and concentrated in a 30 kDa Amicon concentrator at 1000-2000 g and 4° C. to a concentration of 10mg/ml, and stored at 4° C.

Western Blot Analysis

The N-domain (SEQ ID NO: 4, residues 1-629) of ACE protein was detected and its purity assessed by Western Blot analysis using 10% SDS-PAGE and transferred on nitrocellulose membrane (Hybond-C, Amersham). The membrane is probed with N-domain specific monoclonal antibody (5C5) and developed with using the ECP chemiluminescent kit (Amersham) and visualised on autoradiographic film according to the manufacturer's instructions.

Crystallisation and X-Ray Diffraction Data Collection

1 μl of the purified N-domain (SEQ ID NO: 4, residues 1-629) of ACE protein at 4mg/ml was mixed with 1 μl reservoir solution (0.2M lithium sulphate, 0.1M sodium acetate, pH 4.9, 10 μM zinc sulphate, 15% polyethylene glycol 4000) and suspended above the reservoir as a hanging drop at 16° C. Crystals grew within 1-2 weeks.

A single crystal was cryocooled (100 K) using reservoir solution plus 25% glycerol as a cryoprotectant. Diffraction data to 3.0 Å were collected on station PX14.1 of the synchrotron radiation source (Daresbury, U.K.) using a Quantum 4 charge-coupled-device detector (Area Detection Systems, Poway, Calif.). The data were processed and scaled by using the HKL2000 software package (HKL Research, Charlottesville, Va.) (Otwinowski, W. Oscillation data reduction program. in *Proceedings of the CCP*4 *weekend* 56-62 (Daresbury Laboratory, Warrington, U K, 1993). The symmetry and systematic absences were consistent with the $C222_1$ space group (unit cell dimensions, a=101.12 Å; b=211.32 Å; and c=171.27 Å) with two proteins per asymmetric unit. The crystals contained ~54% solvent. Data reduction was carried out by using the CCP4 program TRUNCATE (CCP4. The CCP4 suite: Programs for protein crystallography. *Acta Crystallogr*. D 50, 760-763 (1994)).

The structure of the N-domain (SEQ ID NO: 1) was solved with the program MOLREP (Vagin, A. & Teplyakov, A. An approach to multi-copy search in molecular replacement. *Acta Crystallogr*. D56, 1622-1624 (2000)) using a homology model of the N-domain (SEQ ID NO: 1) based on the tACE (SEQ ID NO: 2) structure (protein data bank entry 1O8A) as a search model. Initial refinement was performed using REFMAC Murshudov, G.N. Refinement of macromolecular structures by the maximum-likelihood method. *Acta Crystallogr*. D53, 240-255 (1997) through the CCP4i interface (CCP4. The CCP4 suite: Programs for protein crystallography. *Acta Crystallogr*. D50, 760-763 (1994)). 4% of reflections was kept aside for Rfree calculation (Brunger, A.T. Free R value: a novel statistical quantity for assessing the accuracy of crystal structures. *Nature* 355, 472-475 (1992)). A large part of the C terminal region not present in the tACE (SEQ ID NO: 2) structure could be built after the first round of refinement using the program Coot (Emsley, P. & Cowtan, K. Coot: Model building tools for molecular graphics. *Acta Crystallogr*. 60, 2126-2132 (2004)). Further rounds of refinement and model building allowed the building of the N terminus and the addition of water, carbohydrate and glycerol molecules plus an acetate ion. Final refinement was done using the CNS suite (Brunger, A.T. et al. Crystallography & NMR system: A new software suite for macromolecular structure determination. *Acta Crystallogr*. D54, 905-921 (1998)).

Figure 4:
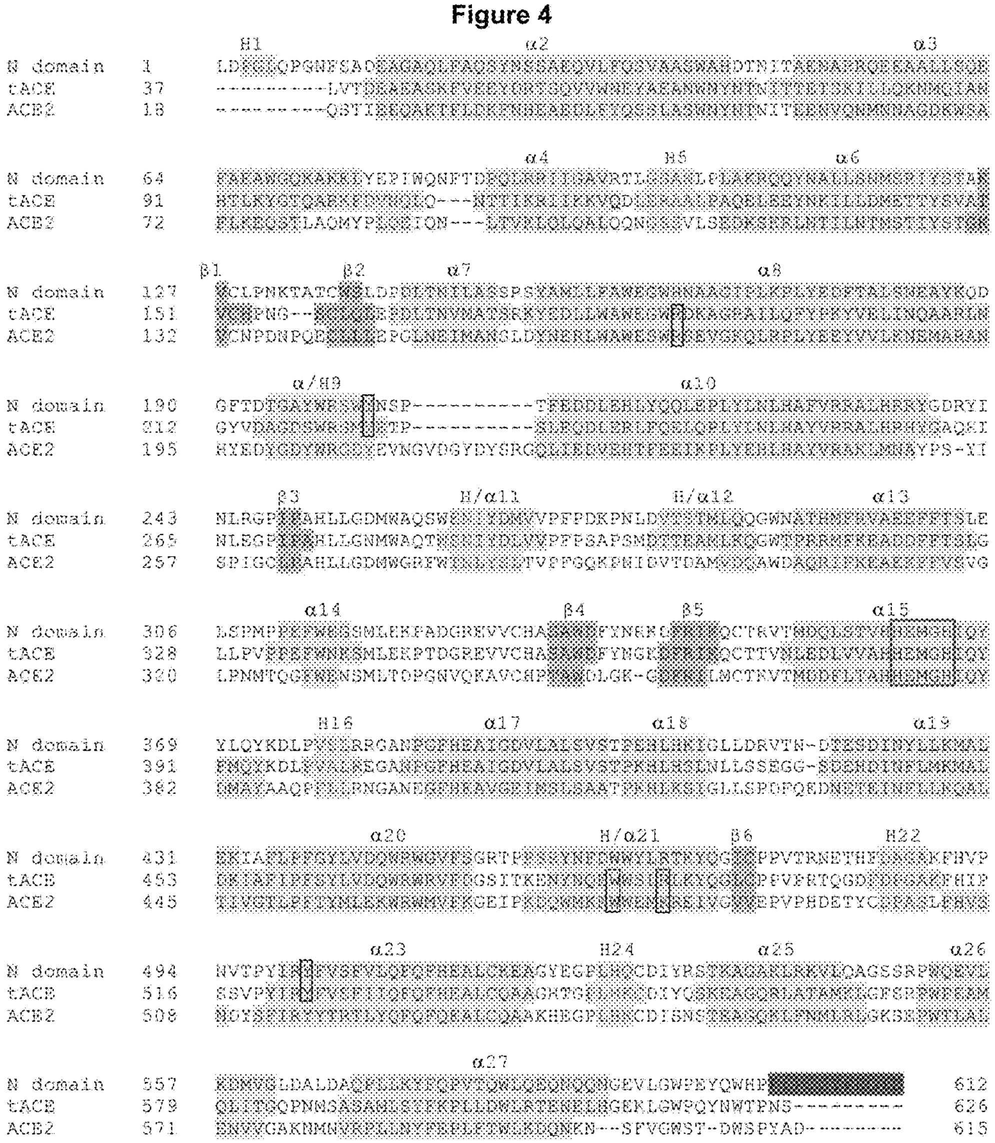
FIG. 4. Sequence alignment of the sACE N-domain (SEQ ID NO: 1) with tACE (SEQ ID NO: 2) and ACE2 (SEQ ID NO: 3). Helices are highlighted in yellow and strands in blue. The linker region is shown in pink. Helices are numbered sequentially whether α or $3_{10}$, and $3_{10}$ helices are shown with red letters. Chloride I coordinating residues are boxed in dark blue, chloride II in black, and the zinc binding motif in red.

Sequence alignment of the sACE N-domain (SEQ ID NO: 1) with tACE (SEQ ID NO: 2) and ACE2 (SEQ ID NO: 3) is shown in FIG. 4.

The N-domain (SEQ ID NO: 4)/lisinopril inhibitor complex—4 mg/ml of purified N-domain (SEQ ID NO: 4, residues 1-629) was incubated with 5 mM lisinopril for 5 hours at 4° C. 1 μl N-domain (SEQ ID NO: 4, residues 1-629) with lisinopril was mixed with 1 μreservoir solution (0.2M lithium sulphate, 0.1M sodium acetate, pH 4.9, 10 μM zinc sulphate, 18% polyethylene glycol 4000) and suspended above the reservoir as a hanging drop at 16° C. Crystals grew within 1-2 weeks in the same form as the minimally glycosylated N-domain of ACE protein. Single crystal consistent with the $C222_1$ space group (unit cell dimensions, a =101.32 Å; b =211.90 Å; and c =171.03 Å). Diffraction data to 2.8 Å were collected as for the minimally glycosylated N-domain data set. The data were processed with MOSFLM (Leslie, A.G.W. Recent changes to the MOSFLM package for processing film and image plate data. Joint CCP4+ESF-EAMCB *Newsletter on Protein Crystallography* 26(1992)), scaled with SCALA (CCP4. The CCP4 suite: Programs for protein crystallography. *Acta Crystallogr*. D50, 760-763 (1994)) and data reduction carried out by TRUNCATE (CCP4. The CCP4 suite: Programs for protein crystallography. *Acta Crystallogr*. D50, 760-763 (1994)).

Refinement (with 2.3% of the reflection kept for the Rfree calculation) of the minimally glycosylated N-domain structure with the CNS suite (Brünger, A. T. et al. Crystallography & NMR system: A new software suite for macromolecular structure determination. *Acta Crystallogr*. D 54, 905-921 (1998)) showed clear difference density for the lisinopril, which was modelled with the program Coot (Emsley, P. & Cowtan, K. Coot: Model building tools for molecular graphics. *Acta Crystallogr.* 60, 2126-2132 (2004)), along with a few water, carbohydrate, glycerol molecules and an acetate ion.

The atomic coordinates have been deposited with the Protein Data Bank, www.rcsb.org, and the accession codes are 2C6F and 2C6N for the minimally glycosylated and lisinopril complexes for sACE N-domain respectively.

All crystals are isomorphous.

Example 2

I. Overall structure of the N-domain The N-domain (SEQ ID NO: 4, residues 1-629) was crystallised with two molecules per asymmetric unit. The overall fold consists of a mainly helical secondary structure, with the same topology as tACE (SEQ ID NO: 2). The N-domain has the ellipsoid shape with a central groove dividing it into two subdomains, one containing the N-terminal lid that covers the central binding cavity. There are 27 helices, of which 18 of them are α helices, 5 are short 3 helices and 4 are mixed (Woodman, Z.L. et al., The N-domain of somatic angiotensin-converting enzyme negatively regulates ectodomain shedding and catalytic activity. *Biochem* J. 389, 739-744 (2005)). There are also 6 short (β-strands. The structures of both molecules in the asymmetric are very similar with a root mean square deviation for the Cα □atoms of 0.50 Å. Analysis of the Ramachandran plot using the program PROCHECK shows that 94% of the residues lie in the most favoured region, with none in the disallowed region (Laskowski, R.A., MacArthur, M.W., Moss, D.S. & Thronton, J.M. PROCHECK -A program to check the stereochemical quality of protein structures. J. *Appl. Crystallogr.* 26, 283-291 (1993)). Both termini are well ordered with all the residues (1-612) being modelled for molecule A and only the N-terminal residue missing in molecule B.

The catalytic zinc ion was observed at the active site and one chloride, equivalent to chloride 2 of tACE, adjacent to Arg500. There are ten putative N-glycosylation sites on the human N-domain protein and Fourier difference density was observed at five of these sites in our structure (FIG. 1(A)). Seven N-acetyl glucosamine residues were modelled on molecule A at asparagines 25, 45, 117, 289 and 480, and six on molecule B at residues 25, 45, 117 and 480. A mannose residue was also modelled on both molecules at the end of the disaccharide at Asn25. Although the B-factors for these sugars are high, they are modelled on the basis of clear difference density, at least for the ring portions. Twentyfive water molecules were modelled by visual inspection and a glycerol molecule was modelled on the surface of each molecule adjacent to Glu219. Three acetate molecules were also modelled, one on the surface next to the symmetry axis and one in each of the active sites adjacent to Lys489, where a carboxyalanine was modelled in the tACE structure (Natesh, R., Schwager, S. L. U., Sturrock, E. D. & Acharya, K. R. Crystal structure of the human angiotensin-converting enzyme-lisinopril complex. *Nature* 421, 551-554 (2003)). We attempted to model N-carboxyalanine at this position however the density-was smaller in the N domain structure.

The N-domain (SEQ ID NO: 4, residues 1-629) protein was also crystallised in the presence of 5 mM lisinopril, for which clear difference density was observed upon refinement with the minimally glycosylated N-domain structure. The overall structure is as the minimally glycosylated N-domain, although the lack of completeness in the data results in poorly defined density for the first 30 residues of the N-terminus. The lisinopril is bound at the active site in the same position and conformation as observed for tACE (SEQ ID NO: 2) (Natesh, R., Schwager, S.L.U., Sturrock, E.D. & Acharya, K.R. Crystal structure of the human angiotensin-converting enzyme-lisinopril complex. *Nature* 421, 551-554 (2003)). Four N-acetyl glucosamine residues each were modelled on both molecules at asparagines 25, 117, and 480. Nineteen water molecules, two glycerols and one acetate ion were modelled. The acetate ion was modelled near the symmetry axis and the two the glycerols at equivalent surface positions on the two molecules, similar to as observed in the minimally glycosylated structure.

Comparison of the N and C Domains

The N- and C- domains of somatic ACE have ~60% sequence identity and hence share the same overall topology as well as the highly conserved zinc binding motif at the active site (see figure x which will be a sequence alignment). The most easily observable difference between the N- (based on SEQ ID NO: 1) and C- domains (based on tACE (SEQ ID NO: 2)) when superimposed (FIG. 1(B)) is the extra length of the N- domain (SEQ ID NO: 1) at the N- terminus and the C terminus, which includes the inter-domain linker. The N terminus of the N-domain protein (SEQ ID NO: 1), whilst having higher than average B factors, is well defined and packs against helix 3. Also, the loop between helices 19 and 20 (residues 409-417) that was not visible in the tACE (SEQ ID NO: 2) structure, is well defined. Three other flexible loops, between helices 3 and 4, strands 1 and 2 and strand 6 and helix 23, show small differences between the domains.

The N-domain has been observed to be activated at lower chloride concentrations and to a lesser extent than the C-domain (Wei, L., Clauser, E., Alhenc-Gelas, F. & Corvol, P. The two homologous domains of human angiotensin I-converting enzyme interact differently with competitive inhibitors. *J. Biol. Chem.* 267, 13389-13405 (1992)). Consistent with this is the observation of only one chloride bound to the N-domain (SEQ ID NO: 1), rather than the two observed for tACE (SEQ ID NO: 2). The chloride ion is observed at the identical site as chloride II in tACE (SEQ ID NO: 2), bound between Tyr 202 and Arg 500. At the equivalent position to the tACE (SEQ ID NO: 2) chloride I site, a crucial arginine is substituted by a histidine in the N-domain (SEQ ID NO: 1). Interestingly, ACE2 (SEQ ID NO: 3), which was also only observed to bind one chloride ion in the crystal structure, binds chloride in the equivalent position to chloride I in tACE (SEQ ID NO: 2).

The domain arrangement of sACE

The complex kinetics of the somatic ACE catalysis is partly due to the presence of an active site in both the N and C domains and also the potential for interaction between them. The N and C-domains of sACE are joined by a linker that is susceptible to proteolysis and is assumed to be partly flexible (Sturrock, E.D., Danilov, S.M. & Riordan, J.F. Limited proteolysis of human kidney angiotensin-converting enzyme and generation of catalytically active N- and C-terminal domains. *Biochem. Biophys. Res. Com.* 236, 16-19 (1997)). The inclusion of the linker in the N-domain (SEQ ID NO: 1) construct allowed us to visualise this region for the first time. The majority of the linker (residues 602-612) was well defined in the electron density map after the first couple of rounds of refinement and was built into the model without ambiguity. The first part of the linker appears to be rigid in our model and is held in place by a hydrogen bond between Tyr607 and Glu161. The last four residues are more flexible as they have high B factors and their side chains are not visible (FIG. 1(C)). They form a prominent surface patch, away from the core of the N-domain, with a very flexible loop that is anchored by the disulphide bond between Cys128 and Cys136 (FIG. 1(C)-(D)). Although this flexible loop is on the symmetry axis, neither its nor the linker's conformation appear to be involved in any crystal packing interactions. Hence it is most likely that the N-terminus of the C-domain would interact with this patch, and that it could adapt its conformation to one or more arrangements.

There is some evidence that only one domain of sACE is capable of catalysis at one time and that the N-domain may be a negative regulator of the C domain Andújar-Sánchez, M., Cámara-Artigas, A. & Jara-Pérez, V. A calorimetric study of the binding of lisinopril, enalaprilat and captopril to angiotensin-converting enzyme. *Biophys. Chem.* 111, 183-189 (2004); Binevski, P. V., Sizova, E. A., Pozdnev, V. F. & Kost, O. A. Evidence for the negative cooperativity of the two active sites within bovine somatic angiotensin-converting enzyme. *FEBS Lett.* 550, 84-88 (2003); Woodman, Z. L. et al., The N domain of somatic angiotensin-converting enzyme negatively regulates ectodomain shedding and catalytic activity. *Biochem J.* 389, 739-744 (2005)). As the flexible region of the linker appears to be short, then it suggests that the N-domain would interact with the N-terminal lid region of the C-domain. The lid region comprise the three (largest) N terminal α-helices in both the N- and C-domains that partly covers the substrate channel (Natesh, R., Schwager, S. L. U., Sturrock, E. D. & Acharya, K. R. Crystal structure of the human angiotensin-converting enzyme-lisinopril complex. *Nature* 421, 551-554 (2003)). It is thought that a change in conformation of the lid may be necessary for entry of the substrate and might also contribute to the substrate specificity of the domains. The interaction of the N-domain with the C-domain lid might reduce the flexibility of this region to regulate the entry of substrate to the C-domain active site or even to form a surface that partially blocked the cavity opening. By contrast, the position of the linker ensures that the C-domain is unlikely to interact with the lid region of the N-domain, although it could block the product channel.

The specific interactions between the domains are not obvious, however, particularly as the terminal three residues of the linker are not available in our structure. Furthermore, several side chains on the linker and the flexible loop, which one might assume to play a part in the interaction, are disordered and not visible. We know from the sequence, however, that the flexible loop contains a positively charged lysine, and the linker, three negatively charged residues.

These may interact with some of the charged residues protruding from the C-domain lid. The N- and C-domain lids have a different shape, size (due to the extra N-terminal residues) and charge distribution. These differences have been suggested to have a link to the substrate specificity of the two domains, but it seems likely that the shape and charge of the C-domain lid will also influence its interaction with the N-domain linker.

Figure 2:
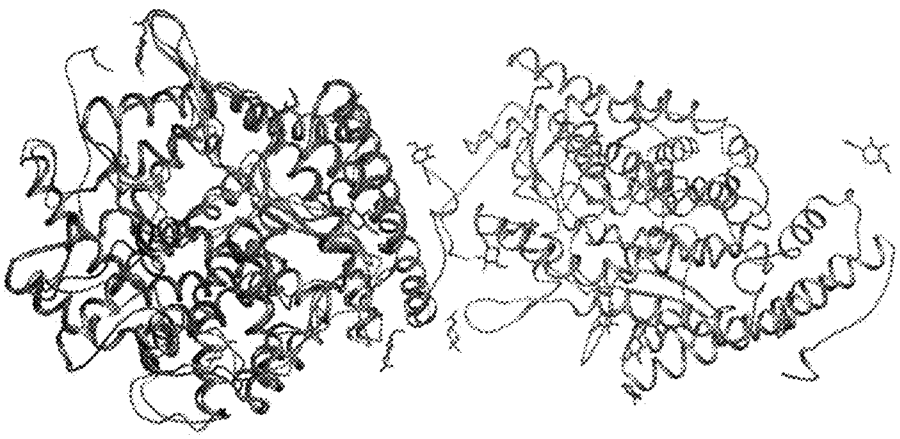
FIG. 2. The top image depicts a model of the possible domain orientation of ACE. The N-terminus and C-terminal linker of two N-domains (SEQ ID NO: 1) (grey) were overlapped and tACE (pink) (SEQ ID NO: 2) superimposed. Sugars moieties visible in the N-domain (SEQ ID NO: 1) and tACE (SEQ ID NO: 2) structures are shown in green, and N-glycosylation sequons where no sugar was observed have been marked by a hypothetical sugar in yellow. The zinc ion in each domain is in green. The bottom image depicts a close-up of the N-domain linker and flexible loop (grey). Pink domain lid showing the residues that might be involved in the inter-domain interaction. Charged residues on the C-terminal lid are shown in red (negative) and blue (positive) with the sugar linked asparagine shown in green. Charged and sugar linked residues are marked by the same colours on the N-domain (SEQ ID NO: 1) ACE, but their side chains are not visible in the structure.
Figure 2:
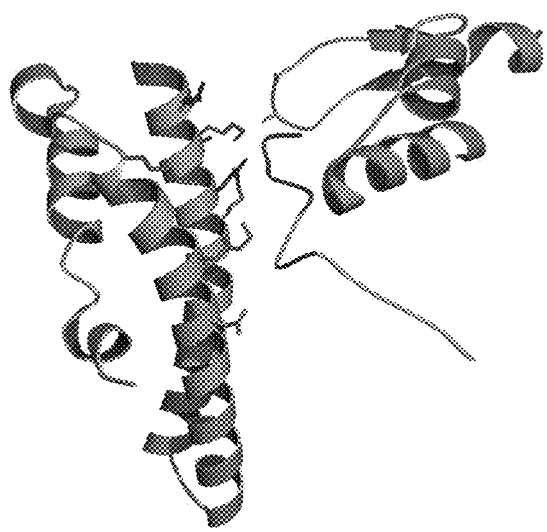

Based on this analysis, and the conformation of the linker, we propose a tentative domain arrangement for sACE. We suggest that the inter-domain linker could pack against the lid of the C-domain, in a similar manner to how the extra N terminal residues of the N-domain, pack against the N-domain lid. To visualise this, two N-domains (SEQ ID NO: 1) were overlapped with the N-terminus of one overlaying the linker of the other (allowing for the missing 3 residues), and then the C-domain (using tACE (SEQ ID NO: 2)) was superimposed (FIG. 2(A)). The initial arrangement caused the C-domain to overlap the flexible loop, suggesting that this loop might mould to the C-domain. Allowing free rotation around the linker produced a model from which it was easier to observe the residues that could be involved in the interaction. FIG. 2(B) shows the charged residues on the N- and C-domains which may help form interactions between them. To complicate matters further, though, there is an N-glycosylation sequon on the flexible loop of the N-domain and the top part of the C-domain lid (FIG. 2(A)), suggesting that inter-domain interactions and movements may be mediated or aided by sugars.

Binding of Lisinopril and specificity

The lisinopril bound to the active site was clearly defined, despite the poor electron density map in some other regions of the structure. The binding followed the same orientation as observed for tACE (SEQ ID NO: 2) with the central carboxylate coordinating the zinc ion and the phenyl group pointing up towards the lid. The active site residues and the lisinopril molecules for the two structures superimpose well (r.m.s. deviation for Cα atoms, 0.31 Å) with nearly all the lisinopril binding residues conserved in the N-domain (SEQ ID NO: 4). tACE Glu 162 (SEQ ID NO: 2), which interacts electrostatically with the amine on the lysyl side chain, is replaced by Asp 140 in the N-domain (SEQ ID NO: 4) away from the P1' group (FIG. 3(A)). Asp 377 of tACE (SEQ ID NO: 2), which forms water mediated interactions with the lysyl group, is also not conserved in the N-domain and is replaced by Gln355. Gln355 could potentially form a hydrogen bond with the lysyl group of lisinopril, although this does not appear to be the case in our structure as it is about 4 Å away. However, it might form water mediated interactions, but water molecules were not visible due to limited resolution of our structure.

A burgeoning area in the field of ACE inhibitor design is the generation of domain specific inhibitors to more precisely regulate the actions of the N- and C-domains of sACE. The structures of two new inhibitors have been published, RXP407 and RXPA380, which are highly specific for the N- and C-domains, respectively. The structural determinants of RXP470 are known to be the N-terminal aspartate and N-acetyl groups in the $P_2$ position and the C-terminal amide.

The difference in phosphinic peptides at the $P_2$ position utilises the differences in the N- and C-domain active site at the $S_2$ subsite (Table 2). RXPA380 has a large hydrophobic phenyl group at this position, whereas the N-domain specific RXP407 has a charged aspartate residue and an N-terminus acetyl group. This corresponds to the exchange of a phenylalanine residue in the C-domain to Tyr 369 in the N-domain (SEQ ID NO: 4). It is probable that the RXPA380 phenyl residue would form a stacking interaction with the Phe391 of tACE (SEQ ID NO: 2), whereas the aspartate or carbonyl (if the aspartate group forms electrostatic interactions with Arg500) of RXP407 would interact with the hydroxyl group of Tyr369 in the N-domain (SEQ ID NO: 4). Interestingly, in both the minimally glycosylated and lisinopril-bound N-domain (SEQ ID NO: 4) structure, a patch of difference density was observed adjacent to Tyr369. This was modelled as a water molecule in the minimally glycosylated structure and a cluster of 2-3 water molecules in the lisinopril-bound structure as it was not possible to tell if it was a larger ligand, e.g. from the crystallisation solution, at this resolution. It is possible that these water molecules in some way mimic the interactions the N-domain would have with extended inhibitors such as RXP407. Indeed, RXP407 can be modelled to make a similar interaction with Tyr369 (FIG. 3(B)).

Figure 3:
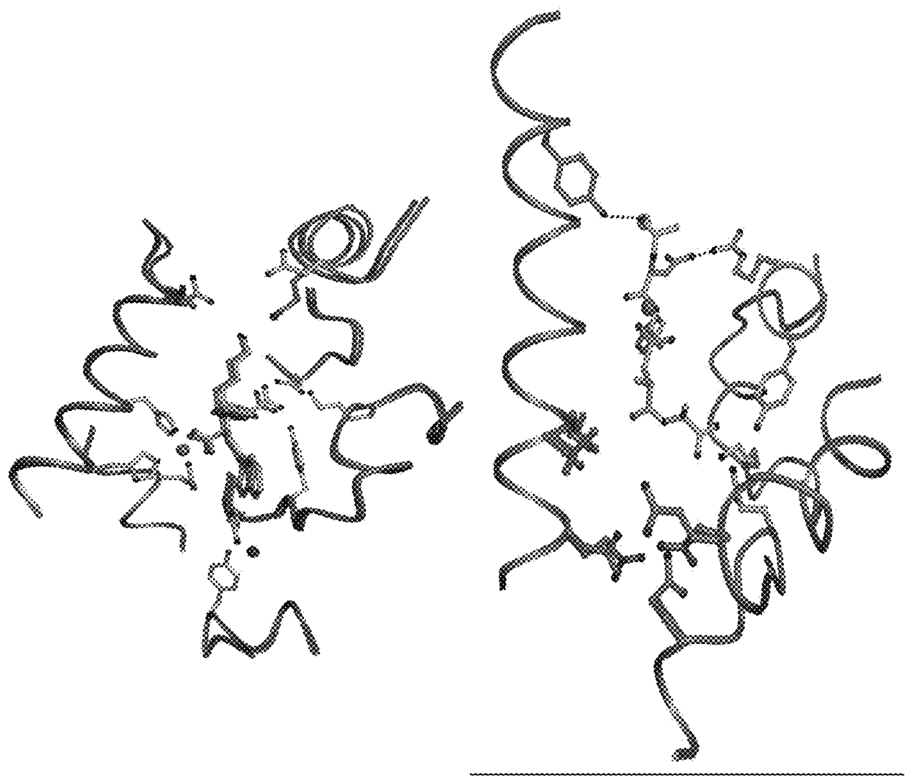
FIG. 3. The image on the left depicts a close-up of the active site of the N-domain (SEQ ID NO: 1) ACE (blue with white residues) and tACE (pink with purple residues) (SEQ ID NO: 2) with the zinc ion in green and the conserved chloride ion in red. Lisinopril is shown in white/purple and the differing residues between the N- and C-domains shown in ball and stick at the top of the picture. The image on the right depicts a close-up of the minimally glycosylated N-domain (SEQ ID NO: 1) active site (blue) with a model of RXP407 (yellow) overlapping the water molecule (grey) adjacent to Tyr 369. Residues differing between the N- and C-domains in the $S_2$ subsite are also shown in ball and stick along with the conserved residues of the $S_1$ subsite that interact with lisinopril. Residues conserved between the N- (SEQ ID NO: 1) and C- domains are shown in white, N-domain (SEQ ID NO: 1) residues shown in blue and C-domain residues shown in pink. The zinc ion is shown in green.

In our structure of the N-domain (SEQ ID NO: 4) protein, the triad of residues (Gln259, Lys489, Tyr498), which interact with the carboxyl group of lisinopril, are best placed to interact with the C terminal amide. However, this triad in conserved in the C-domain and the residues that differ between the N- and C-domains are all located further down the cavity. These include Ser357 and Thr358 (both valine in the C-domain) and a patch of acidic residues (FIG. 3*b*). Although the C-domain also has a patch of 2, rather than 3 acidic residues, they are either different in length or position (Table 2). These residues adopt random conformations in our structure, which lack partner/s in the $S_2$ subsite for them to interact with, but could possibly extend towards the active site and interact in the presence of RXP407. Although the resolution of our structure hinders a more detailed analysis of the active site, the structural details presented here will aid future rational design of domain specific ACE inhibitors.

In a further aspect, the present invention relates to a composition comprising the N-domain of ACE protein in a crystalline form.

In a further aspect, the present invention relates to a scalable 3D model of the N-domain of ACE protein having at least a portion of the structural co-ordinates set forth in Table A (SEQ ID NOs: 5 and 6) or Table B (SEQ ID NOs: 7 and 8).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

REFERENCES 1

1. Beldent, V., Michaud, A., Wei, L., Chauvet, M. T., and Corvol, P. (1993) J. Biol. Chem. 268, 26428-26434.
2. Schwager, S. L. U., Chubb, A. J., Scholle, R. R., Brandt, W. F., Riordan, J. F., Mentele, R., Sturrock, E. D and Ehlers, M. R. W. (1999) *Biochemistry* 38, 10388-10397.
3. Schwager, S. L. U., Chubb, A. J., Woodman, Z. L., Yan, L., Mentele, R., Ehlers, M. R. W., and Sturrock, E. D. (2001) *Biochemistry* 40, 15624-15630.

4. Yu, X. C., Sturrock, E. D., Wu, Z., Biemann, K., Ehlers, M. R. W., and Riordan, J. F. (1997) *J. Biol. Chem.* 272, 3511-3519.

5. Sturrock, E. D., Yu, X. C., Wu, Z., Biemann, K., and Riordan, J. F. (1996) *Biochemistry* 35, 9560-9566.

REFERENCES 2

1a. Junot, C., Gonzales, M. F., Ezan, E., Cotton, J., Vazeux, G., Michaud, A., Azizi, M., Vassiliou, S., Yiotakis, A., Corvol, P., and Dive, V. (2001) *J. Pharmacol. Exp. Ther.* 297, 606-611.

2a. Esther, C. R., Marino, E. M., Howard, T. E., Machaud, A., Corvol, P., Capecchi, M. R., and Bernstein, K. E. (1997) *J. Clin. Invest* 99, 2375-2385.

3a. Sadhukhan, R. and Sen, I. (1996) *J. Biol. Chem.* 271, 6429-6434.

4a. Kumar, R. S., Kusari, J., Roy, S. N., Soffer, R. L., and Sen, G. C. (1989) *J. Biol. Chem.* 264, 16754-16758.

5a. Kasturi, S., Jabbar, M. A., Sen, G. C., and Sen, I. (1994) *Biochemistry* 33, 6228-6234.

6a. Ehlers, M. R., Chen, Y. N., and Riordan, J. F. (1992) *Biochem. Biophys. Res. Commun.* 183, 199-205.

7a. Yu, X. C., Sturrock, E. D., Wu, Z., Biemann, K., Ehlers, M. R., and Riordan, J. F. (1997) *J. Biol. Chem.* 272, 3511-3519.

8a. Ehlers, M. R., Schwager, S. L., Scholle, R. R., Manji, G. A., Brandt, W. F., and Riordan, J. F. (1996) *Biochemistry* 35, 9549-9559.

9a. Schwager, S. L., Chubb, A. J., Scholle, R. R., Brandt, W. F., Eckerskorn, C., Sturrock, E. D., and Ehlers, M. R. (1998) *Biochemistry* 37, 15449-15456.

10a. Wei, L., Alhenc-Gelas, F., Corvol, P., and Clauser, E. (1991) *J. Biol. Chem.* 266, 9002-9008.

11a. Nachon, F., Nicolet, Y., Viguie, N., Masson, P., Fontecilla-Camps, J. C., and Lockridge, O. (2002) *Eur. J. Biochem.* 269, 630-637.

12a. Couvineau, A., Fabre, C., Gaudin, P., Maoret, J. J., and Laburthe, M. (1996) *Biochemistry* 35, 1745-1752.

13a. Zhou, A. T., Assil, I., and Abou-Samra, A. B. (2000) *Biochemistry* 39, 6514-6520.

14a. Schwager, S. L., Chubb, A. J., Scholle, R. R., Brandt, W. F., Mentele, R., Riordan, J. F., Sturrock, E. D., and Ehlers, M. R. (1999) *Biochemistry* 38, 10388-10397.

15a. Davis, S. J., Davies, E. A., Barclay, A. N., Daenke, S., Bodian, D. L., Jones, E. Y., Stuart, D. I., Butters, T. D., Dwek, R. A., and van der Merwe, P. A. (1995) *J. Biol. Chem.* 270, 369-375.

16a. Wheeler, S. F., Rudd, P. M., Davis, S. J., Dwek, R. A., and Harvey, D. J. (2002) *Glycobiology* 12, 261-271.

REFERENCES 3

Abrahams, J. P. & Leslie, A. G. W. Methods used in structure determination of bovine mitochondrial F1 ATPase. *Acta Crystallogr.* D 52, 110-119 (1996).

Brünger, A. T. Free R value: a novel statistical quantity for assessing the accuracy of crystal structure. *Nature* 355, 472-475 (1992).

Brünger, A. T. et al. Crystallography & NMR System: A new software suite for macromolecular structure determination. *Acta Crystallogr.* D 54, 905-921 (1998).

Chubb A. J. Schwager S. L. U., Woodman Z. L., Ehlers, M. R. E., and Sturrock E. D. Defining the ectodomain of angiotensin-converting enzyme. *Biochem. Biophys. Res. Comm.* (2002) in press.

Collaborative computational project Number 4. The CCP4 Suite: Programs for Protein Crystallography. *Acta Crystallogr.* D 50, 760-763 (1994).

Corval, P., Williams, T. A. & Soubrier, F. Peptidyl dipeptidase.A: angiotensin I-converting enzyme. *Methods Enzymol.* 248, 283-305 (1995).

Cushman, D. W., Cheung, H. S., Sabo, E. F. & Ondetti, M. A. Design of potent competitive inhibitors of angiotensin-converting enzyme. Carboxyalkanoyl and mercaptoalkanoyl amino acids. *Biochemistry,* 16, 5484-5491 (1977).

De La Fortelle, E. & Bricogne, G. Maximum-likelihood heavy-atom parameters refinement in the MIR and MAD methods. *Methods Enzymol.* 276, 472-494 (1997).

Holm, L. & Sander, C. Protein folds and families: sequence and structure alignments. *Nucleic Acid Res.* 27, 244-247 (1999).

Hooper, N. M. Families of zinc metalloproteases. *FEBS Lett.* 354, 1-6 (1994).

Jones, T. A., Zou, J. Y., Cowan, S. W. & Kjeldgaard, M. Improved methods for building protein models in electron density maps and the location of errors in these models. *Acta Crystallogr. A* 47, 110-119 (1991).

Kraulis, P. MOLSCRIPT: a program to produce both detailed and schematic plots of protein structures. *J. Appl. Crystallogr.* 24, 946-950 (1991).

Liu, X., Fernandez, M., Wouters, M. A., Heyberger, S. & Husain, A. Arg-1098 is critical for the chloride dependence of human angiotensin-1 converting enzyme C-domain catalytic activity. *J. Biol. Chem.* 276, 33518-33525 (2001).

Merritt, E. A. & Bacon, D. J. Raster 3D:photorealistic molecular graphics. *Methods Enzymol.* 277, 505-524 (1997).

Otwinowski, M. & Minor, W. Processing of X-ray diffraction data collected in oscillation mode. *Methods Enzymol* 276, 307-326 (1997).

Rawlings, N. D. & Barrett, A. J. Evolutionary families of metallopeptidases. *Methods Enzymol.* 248, 182-228 (1995).

Waller, C. L. & Marshall, G. R. Three-dimensional quantitative structure-activity relationship of angiotesin-converting enzyme and thermolysin inhibitors. II. A comparison of CoMFA models incorporating molecular orbital fields and desolvation free energies based on active-analog and complementary-receptor-field alignment rules. *J. Med. Chem.* 36, 2390-2403 (1993).

Wei, L., Alhenc-Gelas, F., Corvol, P. & Clauser, E. The two homologous domains of human angiotensin-1 converting enzyme are both catalytically active. *J. Biol. Chem.* 266, 9002-9008 (1991).

Williams, T. A., Corvol, O. & Soubrier, F. Identification of two active site residues in human angiotensin I-converting enzyme. *J. Biol. Chem.* 269, 29430-29434 (1994).

REFERENCES 4

Natesh, R., Schwager, S. L. U., Sturrock, E. D. & Acharya, K. R. Crystal structure of the human angiotensin-converting enzyme-lisinopril complex. *Nature* 421, 551-554 (2003).

Ehlers, M. R. W. & Riordan, J. F. Angiotensin-converting enzyme: Zinc- and inhibitor-binding stoichiometries of the somatic and testis enzymes. *Biochemistry* 30, 7118-7125 (1991).

Fuchs, S. et al. Role of the N-terminal catalytic domain of ACE investigated by targeted inactivation in mice. *J. Biol. Chem.* 279, 15946-15953 (2004).

Azizi, M. et al. Acute angiotensin-converting enzyme inhibition increases the plasma level of the natural stem cell regulator N-acetyl-serly-aspartyl-lysyl-proline. *J. Clin. Invest.* 97, 839-844 (1996).

Rousseau, A., Michaud, A., Chauvet, M. T., Lenfant, M. & Corvol, P. The hemoregulatory peptide N-acetyl-Ser-Asp-Lys-Pro is a natural and specific substrate of the N-terminal active site of human angiotensin-converting enzyme. *J. Biol. Chem.* 270, 3656-3661 (1995).

Wei, L., Clauser, E., Alhenc-Gelas, F. & Corvol, P. The two homologous domains of human angiotensin I-converting enzyme interact differently with competitive inhibitors. *J. Biol. Chem.* 267, 13389-13405 (1992).

Jaspard, E., Wei, L. & Alhenc-Gelas, F. Differences in the properties and enzymatic specificities of the two active sites of the two active sites of angiotensin I-converting enzyme (kininase II). studies with bradykinin and other natural peptides. *J. Biol. Chem.* 268, 9496-9503 (1993).

Andújar-Sánchez, M., Cámara-Artigas, A. & Jara-Pérez, V. A calorimetric study of the binding of lisinopril, enalaprilat and captopril to angiotensin-converting enzyme. *Biophys. Chem.* 111, 183-189 (2004).

Binevski, P. V., Sizova, E. A., Pozdnev, V. F. & Kost, O. A. Evidence for the negative cooperativity of the two active sites within bovine somatic angiotensin-converting enzyme. *FEBS Lett.* 550, 84-88 (2003).

Woodman, Z. L. et al. The N domain of somatic angiotensin-converting enzyme negatively regulates ectodomain shedding and catalytic activity. *Biochem J.* 389, 739-744 (2005).

Pang, S. et al. Roles of the juxtamembrane and extracellular domains of angiotensin-converting enzyme in ectodomain shedding. *Biochem J.* 358, 185-192 (2001).

Sturrock, E. D., Danilov, S. M. & Riordan, J. F. Limited proteolysis of human kidney angiotensin-converting enzyme and generation of catalytically active N- and C-terminal domains. *Biochem. Biophys. Res. Com.* 236, 16-19 (1997).

Voronov, S., Zueva, N., Orlov, V., Arutyunyan, A. & Kost, O. Temperature-induces selective death of the C-domain within angiotensin-converting enzyme molecule. *FEBS Lett.* 522, 77-82 (2002).

Hagaman, J. R. et al. Angiotensin-converting enzyme and male fertility. *Proc. Natl. Acad. Sci. U.S.A.* 95, 2552-2557 (1998).

Kondoh, G. et al. Angiotensin-converting enzyme is a GPI-anchored protein releasing factor crucial for fertilisation. *Nat. Med.* 11, 160-166 (2005).

Natesh, R., Schwager, S. L. U., Evans, H. R., Sturrock, E. D. & Acharya, K. R. Structural details on the binding of antihypertensive drugs captopril and enalaprilat to human testicular angiotensin I-converting enzyme. *Biochemistry* 43, 8718-8724 (2004).

Kim, H. M., Shin, D. R., Yoo, O. J., Lee, H. & Lee, J. O. Crystal structure of *Drosophila* angiotensin I-converting enzyme bound to captopril and lisinopril. *FEBS Lett.* 538, 65-70 (2003).

Towler, P. et al. ACE2 structures reveal a large hinge-bending motion important for inhibitor binding and catalysis. *J. Biol. Chem.* 279, 17996-18007 (2004).

Otwinowski, W. Oscillation data reduction program. in *Proceedings of the CCP*4 *weekend* 56-62 (Daresbury Laboratory, Warrington, U K, 1993).

CCP4. The CCP4 suite: Programs for protein crystallography. *Acta Crystallogr.* D 50, 760-763 (1994).

Vagin, A. & Teplyakov, A. An approach to multi-copy search in molecular replacement. *Acta Crystallogr.* D 56, 1622-1624 (2000).

Murshudov, G. N. Refinement of macromolecular structures by the maximum-likelihood method. *Acta Crystallogr.* D 53, 240-255 (1997).

Brünger, A. T. Free R value: a novel statistical quantity for assessing the accuracy of crystal structures. *Nature* 355, 472-475 (1992).

Emsley, P. & Cowtan, K. Coot: Model building tools for molecular graphics. *Acta Crystallogr.* 60, 2126-2132 (2004).

Brünger, A. T. et al. Crystallography & NMR system: A new software suite for macromolecular structure determination. *Acta Crystallogr.* D 54, 905-921 (1998).

Leslie, A. G. W. Recent changes to the MOSFLM package for processing film and image plate data. *Joint CCP*4+ *ESF-EAMCB Newsletter on Protein Crystallography* 26 (1992).

Laskowski, R. A., MacArthur, M. W., Moss, D. S. & Thronton, J. M. PROCHECK—A program to check the stereochemical quality of protein structures. *J. Appl. Crystallogr.* 26, 283-291 (1993).

Kost, O. A. et al. Epitope-dependent blocking of the angiotensin-converting enzyme dimerization by monoclonal antibodies to the N-terminal domain of ACE: possible link of ACE dimerization and shedding from the cell surface. *Biochemistry* 42, 6965-6976 (2003).

Balyasnikova, I. V. et al. Localization of an N-domain region of angiotensin-converting enzyme involved in the regulation of ectodomain shedding using monoclonal antibodies. *J. Proteome. Res.* 4, 258-267 (2005).

Danilov, S. M. et al. Structure-function analysis of angiotensin I-converting enzyme using monoclonal antibodies. *J. Biol. Chem.* 269, 26806-26814 (1994).

TABLE 1

| Crystallographic Data | | |
|---|---|---|
| | Native | Lisinopril complex |
| Resolution range, Å | 48.5-3.0 | 50-2.8 |
| No. of reflections measured | 70398 | 160032 |
| No. of unique reflections | 36858 | 40318 |
| //□(/) (outer shell*) | 9.0 (2.2) | 9.2 (1.3) |
| Completeness (outer shell*), % | 99.8 (99.7) | 89.0 (57.3) |
| Rsymm (outer shell*), % | 14.1 (59.5) | 12.6 (52.8) |
| Rcryst, % | 22.5 | 29.8 |
| Rfree, % | 27.4 | 31.4 |
| Average temperature factor $Å^2$ | | |
| Protein (mol A/mol B) | 35.4/38.5 | 39.3/40.2 |
| Carbohydrate (mol A/mol B) | 71.8/74.6 | 71.8/69.8 |
| Ligand | | 48.8/43.2 |
| Solvent [no. of water molecules] | 24.5 [25] | 18.3 [16] |
| $Zn^{2+}$ ion/$Cl^{2-}$ ion | 31.6/40.1 | 39.3/35.3 |
| RMSD from ideal values | | |
| Bond lengths, Å | 0.02 | 0.017 |
| Bond angles, ° | 1.7 | 2.4 |

RMSD, root-mean-square deviation.

Outer shell, 3.11-3.00 Å and 2.95-2.8 Å for the native data and lisinopril complex respectively.

Rfree calculation used 4% and 2.3% of the reflections for the native data and lisinopril complex respectively.

TABLE 2

Active site residues that differ between the N and C domains (C domain numbering is as for tACE).

| | | | | | | | | | |
|---|---|---|---|---|---|---|---|---|---|
| $S_1$ | tACE/C domain | V518 | | | | | | | |
| | N domain | T496 | | | | | | | |
| $S_2$ | tACE/C domain | N70 | E143 | S516 | A63 | Y62 | F391 | V81 | Y69 |
| | N domain | D43 | S119 | N494 | V36 | S35 | Y369 | N54 | H42 |
| $S_1'$ | tACE/C domain | E162 | N374 | E376 | D377 | V380 | N277 | S284 | |
| | N domain | D140 | T352 | D354 | N355 | T358 | D255 | E262 | |
| $S_2'$ | tACE/C domain | D453 | S284 | V380 | V379 | E376 | | | |
| | N domain | E431 | D262 | T358 | S357 | D354 | | | |

The invention claimed is:

1. A crystal of an N-Domain of ACE protein wherein the crystal belongs to the space group $C222_1$, or wherein the crystal has the unit cell dimensions: a=101.12 Å, b=211.32 Å, c=171.27 Å, and wherein the N-domain of ACE comprises an amino acid sequence that shares at least 98% sequence identity to amino acids 1-629 of SEQ ID NO: 4.

2. A crystal according to claim 1, wherein the N-domain of ACE protein is minimally glycosylated at amino acids 25, 45, 117, 289 and 480 of SEQ ID NO: 4.

3. A crystal according to claim 1 comprising atoms arranged in a spatial relationship represented by at least a portion of the structure co-ordinates of Table A or Table B.

4. A crystal according to claim 3 wherein the portion comprises at least 90% of co-ordinates set forth in Table A or Table B.

5. A crystal according to claim 3 wherein the portion comprises at least 99% of co-ordinates set forth in Table A or Table B.

6. A crystal according to claim 1 wherein the crystal further comprises a ligand bound to the N domain of the ACE protein.

7. A crystal according to claim 6 wherein the ligand is bound to the N-domain of the ACE protein by contacting one or more residues of the N-domain of the ACE protein selected from: Gln259, Lys489, and Tyr498.

8. A crystal according to claim 6 wherein the ligand modulates the activity of ACE.

9. A crystal according to claim 6 wherein the ligand is an inhibitor of ACE.

10. A crystal according to claim 6 wherein the ligand is an inhibitor of the N-domain of ACE protein.

11. A crystal according to claim 10 wherein the inhibitor of ACE is lisinopril, captopril, or RXP407, or a derivative thereof.

* * * * *

SEQUENCE LISTING

```
<160> NUMBER OF SEQ ID NOS: 8

<210> SEQ ID NO 1
<211> LENGTH: 612
<212> TYPE: PRT
<213> ORGANISM: Homo sapiens

<400> SEQUENCE: 1

Leu Asp Pro Gly Leu Gln Pro Gly Asn Phe Ser Ala Asp Glu Ala Gly
1               5                   10                  15

Ala Gln Leu Phe Ala Gln Ser Tyr Asn Ser Ser Ala Glu Gln Val Leu
            20                  25                  30

Phe Gln Ser Val Ala Ala Ser Trp Ala His Asp Thr Asn Ile Thr Ala
        35                  40                  45

Glu Asn Ala Arg Arg Gln Glu Glu Ala Ala Leu Leu Ser Gln Glu Phe
    50                  55                  60

Ala Glu Ala Trp Gly Gln Lys Ala Lys Glu Leu Tyr Glu Pro Ile Trp
65                  70                  75                  80

Gln Asn Phe Thr Asp Pro Gln Leu Arg Arg Ile Ile Gly Ala Val Arg
                85                  90                  95

Thr Leu Gly Ser Ala Asn Leu Pro Leu Ala Lys Arg Gln Gln Tyr Asn
            100                 105                 110

Ala Leu Leu Ser Asn Met Ser Arg Ile Tyr Ser Thr Ala Lys Val Cys
        115                 120                 125

Leu Pro Asn Lys Thr Ala Thr Cys Trp Ser Leu Asp Pro Asp Leu Thr
    130                 135                 140

Asn Ile Leu Ala Ser Ser Arg Ser Tyr Ala Met Leu Leu Phe Ala Trp
145                 150                 155                 160

Glu Gly Trp His Asn Ala Ala Gly Ile Pro Leu Lys Pro Leu Tyr Glu
                165                 170                 175

Asp Phe Thr Ala Leu Ser Asn Glu Ala Tyr Lys Gln Asp Gly Phe Thr
            180                 185                 190

Asp Thr Gly Ala Tyr Trp Arg Ser Trp Tyr Asn Ser Pro Thr Phe Glu
        195                 200                 205

Asp Asp Leu Glu His Leu Tyr Gln Gln Leu Glu Pro Leu Tyr Leu Asn
    210                 215                 220

Leu His Ala Phe Val Arg Arg Ala Leu His Arg Arg Tyr Gly Asp Arg
225                 230                 235                 240

Tyr Ile Asn Leu Arg Gly Pro Ile Pro Ala His Leu Leu Gly Asp Met
                245                 250                 255

Trp Ala Gln Ser Trp Glu Asn Ile Tyr Asp Met Val Val Pro Phe Pro
            260                 265                 270

Asp Lys Pro Asn Leu Asp Val Thr Ser Thr Met Leu Gln Gln Gly Trp
        275                 280                 285
```

```
Asn Ala Thr His Met Phe Arg Val Ala Glu Glu Phe Phe Thr Ser Leu
    290                 295                 300

Glu Leu Ser Pro Met Pro Pro Glu Phe Trp Glu Gly Ser Met Leu Glu
305                 310                 315                 320

Lys Pro Ala Asp Gly Arg Glu Val Val Cys His Ala Ser Ala Trp Asp
                325                 330                 335

Phe Tyr Asn Arg Lys Asp Phe Arg Ile Lys Gln Cys Thr Arg Val Thr
            340                 345                 350

Met Asp Gln Leu Ser Thr Val His His Glu Met Gly His Ile Gln Tyr
        355                 360                 365

Tyr Leu Gln Tyr Lys Asp Leu Pro Val Ser Leu Arg Arg Gly Ala Asn
    370                 375                 380

Pro Gly Phe His Glu Ala Ile Gly Asp Val Leu Ala Leu Ser Val Ser
385                 390                 395                 400

Thr Pro Glu His Leu His Lys Ile Gly Leu Leu Asp Arg Val Thr Asn
                405                 410                 415

Asp Thr Glu Ser Asp Ile Asn Tyr Leu Leu Lys Met Ala Leu Glu Lys
            420                 425                 430

Ile Ala Phe Leu Pro Phe Gly Tyr Leu Val Asp Gln Trp Arg Trp Gly
        435                 440                 445

Val Phe Ser Gly Arg Thr Pro Pro Ser Arg Tyr Asn Phe Asp Trp Trp
    450                 455                 460

Tyr Leu Arg Thr Lys Tyr Gln Gly Ile Cys Pro Pro Val Thr Arg Asn
465                 470                 475                 480

Glu Thr His Phe Asp Ala Gly Ala Lys Phe His Val Pro Asn Val Thr
                485                 490                 495

Pro Tyr Ile Arg Tyr Phe Val Ser Phe Val Leu Gln Phe Gln Phe His
            500                 505                 510

Glu Ala Leu Cys Lys Glu Ala Gly Tyr Glu Gly Pro Leu His Gln Cys
        515                 520                 525

Asp Ile Tyr Arg Ser Thr Lys Ala Gly Ala Lys Leu Arg Lys Val Leu
    530                 535                 540

Gln Ala Gly Ser Ser Arg Pro Trp Gln Glu Val Leu Lys Asp Met Val
545                 550                 555                 560

Gly Leu Asp Ala Leu Asp Ala Gln Pro Leu Leu Lys Tyr Phe Gln Pro
                565                 570                 575

Val Thr Gln Trp Leu Gln Glu Gln Asn Gln Gln Asn Gly Glu Val Leu
            580                 585                 590

Gly Trp Pro Glu Tyr Gln Trp His Pro Pro Leu Pro Asp Asn Tyr Pro
        595                 600                 605

Glu Gly Ile Asp
    610
```

<210> SEQ ID NO 2
<211> LENGTH: 589
<212> TYPE: PRT
<213> ORGANISM: Homo sapiens

<400> SEQUENCE: 2

```
Leu Val Thr Asp Glu Ala Glu Ala Ser Lys Phe Val Glu Glu Tyr Asp
1               5                   10                  15

Arg Thr Ser Gln Val Val Trp Asn Glu Tyr Ala Glu Ala Asn Trp Asn
            20                  25                  30

Tyr Asn Thr Asn Ile Thr Thr Glu Thr Ser Lys Ile Leu Leu Gln Lys
```

-continued

```
        35                  40                  45

Asn Met Gln Ile Ala Asn His Thr Leu Lys Tyr Gly Thr Gln Ala Arg
    50                  55                  60

Lys Phe Asp Val Asn Gln Leu Gln Asn Thr Thr Ile Lys Arg Ile Ile
65                  70                  75                  80

Lys Lys Val Gln Asp Leu Glu Arg Ala Ala Leu Pro Ala Gln Glu Leu
                85                  90                  95

Glu Glu Tyr Asn Lys Ile Leu Leu Asp Met Glu Thr Thr Tyr Ser Val
            100                 105                 110

Ala Thr Val Cys His Pro Asn Gly Ser Cys Leu Gln Leu Glu Pro Asp
        115                 120                 125

Leu Thr Asn Val Met Ala Thr Ser Arg Lys Tyr Glu Asp Leu Leu Trp
    130                 135                 140

Ala Trp Glu Gly Trp Arg Asp Lys Ala Gly Arg Ala Ile Leu Gln Phe
145                 150                 155                 160

Tyr Pro Lys Tyr Val Glu Leu Ile Asn Gln Ala Ala Arg Leu Asn Gly
                165                 170                 175

Tyr Val Asp Ala Gly Asp Ser Trp Arg Ser Met Tyr Glu Thr Pro Ser
            180                 185                 190

Leu Glu Gln Asp Leu Glu Arg Leu Phe Gln Glu Leu Gln Pro Leu Tyr
        195                 200                 205

Leu Asn Leu His Ala Tyr Val Arg Arg Ala Leu His Arg His Tyr Gly
    210                 215                 220

Ala Gln His Ile Asn Leu Glu Gly Pro Ile Pro Ala His Leu Leu Gly
225                 230                 235                 240

Asn Met Trp Ala Gln Thr Trp Ser Asn Ile Tyr Asp Leu Val Val Pro
                245                 250                 255

Phe Pro Ser Ala Pro Ser Met Asp Thr Thr Glu Ala Met Leu Lys Gln
            260                 265                 270

Gly Trp Thr Pro Arg Arg Met Phe Lys Glu Ala Asp Asp Phe Phe Thr
        275                 280                 285

Ser Leu Gly Leu Leu Pro Val Pro Pro Glu Phe Trp Asn Lys Ser Met
    290                 295                 300

Leu Glu Lys Pro Thr Asp Gly Arg Glu Val Val Cys His Ala Ser Ala
305                 310                 315                 320

Trp Asp Phe Tyr Asn Gly Lys Asp Phe Arg Ile Lys Gln Cys Thr Thr
                325                 330                 335

Val Asn Leu Glu Asp Leu Val Val Ala His His Glu Met Gly His Ile
            340                 345                 350

Gln Tyr Phe Met Gln Tyr Lys Asp Leu Pro Val Ala Leu Arg Glu Gly
        355                 360                 365

Ala Asn Pro Gly Phe His Glu Ala Ile Gly Asp Val Leu Ala Leu Ser
    370                 375                 380

Val Ser Thr Pro Lys His Leu His Ser Leu Asn Leu Leu Ser Ser Glu
385                 390                 395                 400

Gly Gly Ser Asp Glu His Asp Ile Asn Phe Leu Met Lys Met Ala Leu
                405                 410                 415

Asp Lys Ile Ala Phe Ile Pro Phe Ser Tyr Leu Val Asp Gln Trp Arg
            420                 425                 430

Trp Arg Val Phe Asp Gly Ser Ile Thr Lys Glu Asn Tyr Asn Gln Glu
        435                 440                 445

Trp Trp Ser Leu Arg Leu Lys Tyr Gln Gly Leu Cys Pro Pro Val Pro
    450                 455                 460
```

```
Arg Thr Gln Gly Asp Phe Asp Pro Gly Ala Lys Phe His Ile Pro Ser
465                 470                 475                 480

Ser Val Pro Tyr Ile Arg Tyr Phe Val Ser Phe Ile Ile Gln Phe Gln
                485                 490                 495

Phe His Glu Ala Leu Cys Gln Ala Ala Gly His Thr Gly Pro Leu His
            500                 505                 510

Lys Cys Asp Ile Tyr Gln Ser Lys Glu Ala Gly Gln Arg Leu Ala Thr
        515                 520                 525

Ala Met Lys Leu Gly Phe Ser Arg Pro Trp Pro Glu Ala Met Gln Leu
    530                 535                 540

Ile Thr Gly Gln Pro Asn Met Ser Ala Ser Ala Met Leu Ser Tyr Phe
545                 550                 555                 560

Lys Pro Leu Leu Asp Trp Leu Arg Thr Glu Asn Glu Leu His Gly Glu
                565                 570                 575

Lys Leu Gly Trp Pro Gln Tyr Asn Trp Thr Pro Asn Ser
            580                 585


<210> SEQ ID NO 3
<211> LENGTH: 598
<212> TYPE: PRT
<213> ORGANISM: Homo sapiens

<400> SEQUENCE: 3

Gln Ser Thr Ile Glu Glu Gln Ala Lys Thr Phe Leu Asp Lys Phe Asn
1               5                   10                  15

His Glu Ala Glu Asp Leu Phe Tyr Gln Ser Ser Leu Ala Ser Trp Asn
            20                  25                  30

Tyr Asn Thr Asn Ile Thr Glu Glu Asn Val Gln Asn Met Asn Asn Ala
        35                  40                  45

Gly Asp Lys Trp Ser Ala Phe Leu Lys Glu Gln Ser Thr Leu Ala Gln
    50                  55                  60

Met Tyr Pro Leu Gln Glu Ile Gln Asn Leu Thr Val Lys Leu Gln Leu
65                  70                  75                  80

Gln Ala Leu Gln Gln Asn Gly Ser Ser Val Leu Ser Glu Asp Lys Ser
                85                  90                  95

Lys Arg Leu Asn Thr Ile Leu Asn Thr Met Ser Thr Ile Tyr Ser Thr
            100                 105                 110

Gly Lys Val Cys Asn Pro Asp Asn Pro Gln Glu Cys Leu Leu Leu Glu
        115                 120                 125

Pro Gly Leu Asn Glu Ile Met Ala Asn Ser Leu Asp Tyr Asn Glu Arg
    130                 135                 140

Leu Trp Ala Trp Glu Ser Trp Arg Ser Glu Val Gly Lys Gln Leu Arg
145                 150                 155                 160

Pro Leu Tyr Glu Glu Tyr Val Val Leu Lys Asn Glu Met Ala Arg Ala
                165                 170                 175

Asn His Tyr Glu Asp Tyr Gly Asp Tyr Trp Arg Gly Asp Tyr Glu Val
            180                 185                 190

Asn Gly Val Asp Gly Tyr Asp Tyr Ser Arg Gly Gln Leu Ile Glu Asp
        195                 200                 205

Val Glu His Thr Phe Glu Glu Ile Lys Pro Leu Tyr Glu His Leu His
    210                 215                 220

Ala Tyr Val Arg Ala Lys Leu Met Asn Ala Tyr Pro Ser Tyr Ile Ser
225                 230                 235                 240

Pro Ile Gly Cys Leu Pro Ala His Leu Leu Gly Asp Met Trp Gly Arg
```

-continued

```
                245                 250                 255

Phe Trp Thr Asn Leu Tyr Ser Leu Thr Val Pro Phe Gly Gln Lys Pro
            260                 265                 270

Asn Ile Asp Val Thr Asp Ala Met Val Asp Gln Ala Trp Asp Ala Gln
        275                 280                 285

Arg Ile Phe Lys Glu Ala Glu Lys Phe Phe Val Ser Val Gly Leu Pro
    290                 295                 300

Asn Met Thr Gln Gly Phe Trp Glu Asn Ser Met Leu Thr Asp Pro Gly
305                 310                 315                 320

Asn Val Gln Lys Ala Val Cys His Pro Thr Ala Trp Asp Leu Gly Lys
                325                 330                 335

Gly Asp Phe Arg Ile Leu Met Cys Thr Lys Val Thr Met Asp Asp Phe
            340                 345                 350

Leu Thr Ala His His Glu Met Gly His Ile Gln Tyr Asp Met Ala Tyr
        355                 360                 365

Ala Ala Gln Pro Phe Leu Leu Arg Asn Gly Ala Asn Glu Gly Phe His
    370                 375                 380

Glu Ala Val Gly Glu Ile Met Ser Leu Ser Ala Ala Thr Pro Lys His
385                 390                 395                 400

Leu Lys Ser Ile Gly Leu Leu Ser Pro Asp Phe Gln Glu Asp Asn Glu
                405                 410                 415

Thr Glu Ile Asn Phe Leu Leu Lys Gln Ala Leu Thr Ile Val Gly Thr
            420                 425                 430

Leu Pro Phe Thr Tyr Met Leu Glu Lys Trp Arg Trp Met Val Phe Lys
        435                 440                 445

Gly Glu Ile Pro Lys Asp Gln Trp Met Lys Lys Trp Trp Glu Met Lys
    450                 455                 460

Arg Glu Ile Val Gly Val Val Glu Pro Val Pro His Asp Glu Thr Tyr
465                 470                 475                 480

Cys Asp Pro Ala Ser Leu Phe His Val Ser Asn Asp Tyr Ser Phe Ile
                485                 490                 495

Arg Tyr Tyr Thr Arg Thr Leu Tyr Gln Phe Gln Phe Gln Glu Ala Leu
            500                 505                 510

Cys Gln Ala Ala Lys His Glu Gly Pro Leu His Lys Cys Asp Ile Ser
        515                 520                 525

Asn Ser Thr Glu Ala Gly Gln Lys Leu Phe Asn Met Leu Arg Leu Gly
    530                 535                 540

Lys Ser Glu Pro Trp Thr Leu Ala Leu Glu Asn Val Val Gly Ala Lys
545                 550                 555                 560

Asn Met Asn Val Arg Pro Leu Leu Asn Tyr Phe Glu Pro Leu Phe Thr
                565                 570                 575

Trp Leu Lys Asp Gln Asn Lys Asn Ser Phe Val Gly Trp Ser Thr Asp
            580                 585                 590

Trp Ser Pro Tyr Ala Asp
        595
```

<210> SEQ ID NO 4
<211> LENGTH: 658
<212> TYPE: PRT
<213> ORGANISM: Homo sapiens
<220> FEATURE:
<221> NAME/KEY: mat_peptide
<222> LOCATION: (30)..(658)

<400> SEQUENCE: 4

-continued

```
Met Gly Ala Ala Ser Gly Arg Arg Gly Pro Gly Leu Leu Leu Pro Leu
                -25                 -20                 -15

Pro Leu Leu Leu Leu Leu Pro Pro Gln Pro Ala Leu Ala Leu Asp Pro
            -10                 -5              -1  1

Gly Leu Gln Pro Gly Asn Phe Ser Ala Asp Glu Ala Gly Ala Gln Leu
    5                   10                  15

Phe Ala Gln Ser Tyr Asn Ser Ser Ala Glu Gln Val Leu Phe Gln Ser
20                  25                  30                  35

Val Ala Ala Ser Trp Ala His Asp Thr Asn Ile Thr Ala Glu Asn Ala
                40                  45                  50

Arg Arg Gln Glu Glu Ala Ala Leu Leu Ser Gln Glu Phe Ala Glu Ala
            55                  60                  65

Trp Gly Gln Lys Ala Lys Glu Leu Tyr Glu Pro Ile Trp Gln Asn Phe
        70                  75                  80

Thr Asp Pro Gln Leu Arg Arg Ile Ile Gly Ala Val Arg Thr Leu Gly
    85                  90                  95

Ser Ala Asn Leu Pro Leu Ala Lys Arg Gln Gln Tyr Asn Ala Leu Leu
100                 105                 110                 115

Ser Asn Met Ser Arg Ile Tyr Ser Thr Ala Lys Val Cys Leu Pro Asn
                120                 125                 130

Lys Thr Ala Thr Cys Trp Ser Leu Asp Pro Asp Leu Thr Asn Ile Leu
            135                 140                 145

Ala Ser Ser Arg Ser Tyr Ala Met Leu Leu Phe Ala Trp Glu Gly Trp
        150                 155                 160

His Asn Ala Ala Gly Ile Pro Leu Lys Pro Leu Tyr Glu Asp Phe Thr
    165                 170                 175

Ala Leu Ser Asn Glu Ala Tyr Lys Gln Asp Gly Phe Thr Asp Thr Gly
180                 185                 190                 195

Ala Tyr Trp Arg Ser Trp Tyr Asn Ser Pro Thr Phe Glu Asp Asp Leu
                200                 205                 210

Glu His Leu Tyr Gln Gln Leu Glu Pro Leu Tyr Leu Asn Leu His Ala
            215                 220                 225

Phe Val Arg Arg Ala Leu His Arg Arg Tyr Gly Asp Arg Tyr Ile Asn
        230                 235                 240

Leu Arg Gly Pro Ile Pro Ala His Leu Leu Gly Asp Met Trp Ala Gln
    245                 250                 255

Ser Trp Glu Asn Ile Tyr Asp Met Val Val Pro Phe Pro Asp Lys Pro
260                 265                 270                 275

Asn Leu Asp Val Thr Ser Thr Met Leu Gln Gln Gly Trp Asn Ala Thr
                280                 285                 290

His Met Phe Arg Val Ala Glu Glu Phe Phe Thr Ser Leu Glu Leu Ser
            295                 300                 305

Pro Met Pro Pro Glu Phe Trp Glu Gly Ser Met Leu Glu Lys Pro Ala
        310                 315                 320

Asp Gly Arg Glu Val Val Cys His Ala Ser Ala Trp Asp Phe Tyr Asn
    325                 330                 335

Arg Lys Asp Phe Arg Ile Lys Gln Cys Thr Arg Val Thr Met Asp Gln
340                 345                 350                 355

Leu Ser Thr Val His His Glu Met Gly His Ile Gln Tyr Tyr Leu Gln
                360                 365                 370

Tyr Lys Asp Leu Pro Val Ser Leu Arg Arg Gly Ala Asn Pro Gly Phe
            375                 380                 385

His Glu Ala Ile Gly Asp Val Leu Ala Leu Ser Val Ser Thr Pro Glu
```

```
        390                 395                 400

His Leu His Lys Ile Gly Leu Leu Asp Arg Val Thr Asn Asp Thr Glu
    405                 410                 415

Ser Asp Ile Asn Tyr Leu Leu Lys Met Ala Leu Glu Lys Ile Ala Phe
420                 425                 430                 435

Leu Pro Phe Gly Tyr Leu Val Asp Gln Trp Arg Trp Gly Val Phe Ser
                440                 445                 450

Gly Arg Thr Pro Pro Ser Arg Tyr Asn Phe Asp Trp Trp Tyr Leu Arg
            455                 460                 465

Thr Lys Tyr Gln Gly Ile Cys Pro Pro Val Thr Arg Asn Glu Thr His
        470                 475                 480

Phe Asp Ala Gly Ala Lys Phe His Val Pro Asn Val Thr Pro Tyr Ile
    485                 490                 495

Arg Tyr Phe Val Ser Phe Val Leu Gln Phe Gln Phe His Glu Ala Leu
500                 505                 510                 515

Cys Lys Glu Ala Gly Tyr Glu Gly Pro Leu His Gln Cys Asp Ile Tyr
                520                 525                 530

Arg Ser Thr Lys Ala Gly Ala Lys Leu Arg Lys Val Leu Gln Ala Gly
            535                 540                 545

Ser Ser Arg Pro Trp Gln Glu Val Leu Lys Asp Met Val Gly Leu Asp
        550                 555                 560

Ala Leu Asp Ala Gln Pro Leu Leu Lys Tyr Phe Gln Pro Val Thr Gln
    565                 570                 575

Trp Leu Gln Glu Gln Asn Gln Gln Asn Gly Glu Val Leu Gly Trp Pro
580                 585                 590                 595

Glu Tyr Gln Trp His Pro Pro Leu Pro Asp Asn Tyr Pro Glu Gly Ile
                600                 605                 610

Asp Leu Val Thr Asp Glu Ala Glu Ala Ser Lys Phe Val Glu Glu Tyr
            615                 620                 625

Asp Leu


<210> SEQ ID NO 5
<211> LENGTH: 612
<212> TYPE: PRT
<213> ORGANISM: Homo sapiens

<400> SEQUENCE: 5

Ala Asp Pro Gly Leu Gln Pro Gly Asn Phe Ser Ala Asp Glu Ala Gly
1               5                   10                  15

Ala Gln Leu Phe Ala Gln Ser Tyr Asn Ser Ser Ala Glu Gln Val Leu
            20                  25                  30

Phe Gln Ser Val Ala Ala Ser Trp Ala His Asp Thr Asn Ile Thr Ala
        35                  40                  45

Glu Asn Ala Arg Arg Gln Glu Glu Ala Ala Leu Leu Ser Gln Glu Phe
    50                  55                  60

Ala Glu Ala Trp Gly Gln Lys Ala Lys Glu Leu Tyr Glu Pro Ile Trp
65                  70                  75                  80

Gln Asn Phe Thr Asp Pro Gln Leu Arg Arg Ile Ile Gly Ala Val Arg
                85                  90                  95

Thr Leu Gly Ser Ala Asn Leu Pro Leu Ala Lys Arg Gln Gln Tyr Asn
            100                 105                 110

Ala Leu Leu Ser Asn Met Ser Arg Ile Tyr Ser Thr Ala Lys Val Cys
        115                 120                 125

Leu Pro Asn Lys Thr Ala Thr Cys Trp Ser Leu Asp Pro Asp Leu Thr
```

-continued

```
    130                 135                 140

Asn Ile Leu Ala Ser Ser Arg Ser Tyr Ala Met Leu Leu Phe Ala Trp
145                 150                 155                 160

Glu Gly Trp His Asn Ala Ala Gly Ile Pro Leu Lys Pro Leu Tyr Glu
                165                 170                 175

Asp Phe Thr Ala Leu Ser Asn Glu Ala Tyr Lys Gln Asp Gly Phe Thr
            180                 185                 190

Asp Thr Gly Ala Tyr Trp Arg Ser Trp Tyr Asn Ser Pro Thr Phe Glu
        195                 200                 205

Asp Asp Leu Glu His Leu Tyr Gln Gln Leu Glu Pro Leu Tyr Leu Asn
    210                 215                 220

Leu His Ala Phe Val Arg Arg Ala Leu His Arg Arg Tyr Gly Asp Arg
225                 230                 235                 240

Tyr Ile Asn Leu Arg Gly Pro Ile Pro Ala His Leu Leu Gly Asp Met
                245                 250                 255

Trp Ala Gln Ser Trp Glu Asn Ile Tyr Asp Met Val Val Pro Phe Pro
            260                 265                 270

Asp Lys Pro Asn Leu Asp Val Thr Ser Thr Met Leu Gln Gln Gly Trp
        275                 280                 285

Asn Ala Thr His Met Phe Arg Val Ala Glu Glu Phe Phe Thr Ser Leu
    290                 295                 300

Glu Leu Ser Pro Met Pro Pro Glu Phe Trp Glu Gly Ser Met Leu Glu
305                 310                 315                 320

Lys Pro Ala Asp Gly Arg Glu Val Val Cys His Ala Ser Ala Trp Asp
                325                 330                 335

Phe Tyr Asn Arg Lys Asp Phe Arg Ile Lys Gln Cys Thr Arg Val Thr
            340                 345                 350

Met Asp Gln Leu Ser Thr Val His His Glu Met Gly His Ile Gln Tyr
        355                 360                 365

Tyr Leu Gln Tyr Lys Asp Leu Pro Val Ser Leu Arg Arg Gly Ala Asn
    370                 375                 380

Pro Gly Phe His Glu Ala Ile Gly Asp Val Leu Ala Leu Ser Val Ser
385                 390                 395                 400

Thr Pro Glu His Leu His Lys Ile Gly Leu Leu Asp Arg Val Thr Asn
                405                 410                 415

Asp Thr Glu Ser Asp Ile Asn Tyr Leu Leu Lys Met Ala Leu Glu Lys
            420                 425                 430

Ile Ala Phe Leu Pro Phe Gly Tyr Leu Val Asp Gln Trp Arg Trp Gly
        435                 440                 445

Val Phe Ser Gly Arg Thr Pro Pro Ser Arg Tyr Asn Phe Asp Trp Trp
    450                 455                 460

Tyr Leu Arg Thr Lys Tyr Gln Gly Ile Cys Pro Pro Val Thr Arg Asn
465                 470                 475                 480

Glu Thr His Phe Asp Ala Gly Ala Lys Phe His Val Pro Asn Val Thr
                485                 490                 495

Pro Tyr Ile Arg Tyr Phe Val Ser Phe Val Leu Gln Phe Gln Phe His
            500                 505                 510

Glu Ala Leu Cys Lys Glu Ala Gly Tyr Glu Gly Pro Leu His Gln Cys
        515                 520                 525

Asp Ile Tyr Arg Ser Thr Lys Ala Gly Ala Lys Leu Arg Lys Val Leu
    530                 535                 540

Gln Ala Gly Ser Ser Arg Pro Trp Gln Glu Val Leu Lys Asp Met Val
545                 550                 555                 560
```

```
Gly Leu Asp Ala Leu Asp Ala Gln Pro Leu Leu Lys Tyr Phe Gln Pro
                565                 570                 575

Val Thr Gln Trp Leu Gln Glu Gln Asn Gln Gln Asn Gly Glu Val Leu
            580                 585                 590

Gly Trp Pro Glu Tyr Gln Trp His Pro Pro Leu Pro Asp Asn Tyr Pro
        595                 600                 605

Ala Gly Ala Ala
    610


<210> SEQ ID NO 6
<211> LENGTH: 611
<212> TYPE: PRT
<213> ORGANISM: Homo sapiens

<400> SEQUENCE: 6

Ala Pro Gly Leu Gln Pro Gly Asn Phe Ser Ala Asp Glu Ala Gly Ala
1               5                   10                  15

Gln Leu Phe Ala Gln Ser Tyr Asn Ser Ser Ala Glu Gln Val Leu Phe
            20                  25                  30

Gln Ser Val Ala Ala Ser Trp Ala His Asp Thr Asn Ile Thr Ala Glu
        35                  40                  45

Asn Ala Arg Arg Gln Glu Glu Ala Ala Leu Leu Ser Gln Glu Phe Ala
    50                  55                  60

Glu Ala Trp Gly Gln Lys Ala Lys Glu Leu Tyr Glu Pro Ile Trp Gln
65                  70                  75                  80

Asn Phe Thr Asp Pro Gln Leu Arg Arg Ile Ile Gly Ala Val Arg Thr
                85                  90                  95

Leu Gly Ser Ala Asn Leu Pro Leu Ala Lys Arg Gln Gln Tyr Asn Ala
            100                 105                 110

Leu Leu Ser Asn Met Ser Arg Ile Tyr Ser Thr Ala Lys Val Cys Leu
        115                 120                 125

Pro Asn Lys Thr Ala Thr Cys Trp Ser Leu Asp Pro Asp Leu Thr Asn
    130                 135                 140

Ile Leu Ala Ser Ser Arg Ser Tyr Ala Met Leu Leu Phe Ala Trp Glu
145                 150                 155                 160

Gly Trp His Asn Ala Ala Gly Ile Pro Leu Lys Pro Leu Tyr Glu Asp
                165                 170                 175

Phe Thr Ala Leu Ser Asn Glu Ala Tyr Lys Gln Asp Gly Phe Thr Asp
            180                 185                 190

Thr Gly Ala Tyr Trp Arg Ser Trp Tyr Asn Ser Pro Thr Phe Glu Asp
        195                 200                 205

Asp Leu Glu His Leu Tyr Gln Gln Leu Glu Pro Leu Tyr Leu Asn Leu
    210                 215                 220

His Ala Phe Val Arg Arg Ala Leu His Arg Arg Tyr Gly Asp Arg Tyr
225                 230                 235                 240

Ile Asn Leu Arg Gly Pro Ile Pro Ala His Leu Leu Gly Asp Met Trp
                245                 250                 255

Ala Gln Ser Trp Glu Asn Ile Tyr Asp Met Val Val Pro Phe Pro Asp
            260                 265                 270

Lys Pro Asn Leu Asp Val Thr Ser Thr Met Leu Gln Gln Gly Trp Asn
        275                 280                 285

Ala Thr His Met Phe Arg Val Ala Glu Glu Phe Phe Thr Ser Leu Glu
    290                 295                 300

Leu Ser Pro Met Pro Pro Glu Phe Trp Glu Gly Ser Met Leu Glu Lys
```

305 310 315 320

Pro Ala Asp Gly Arg Glu Val Val Cys His Ala Ser Ala Trp Asp Phe
325 330 335

Tyr Asn Arg Lys Asp Phe Arg Ile Lys Gln Cys Thr Arg Val Thr Met
340 345 350

Asp Gln Leu Ser Thr Val His His Glu Met Gly His Ile Gln Tyr Tyr
355 360 365

Leu Gln Tyr Lys Asp Leu Pro Val Ser Leu Arg Arg Gly Ala Asn Pro
370 375 380

Gly Phe His Glu Ala Ile Gly Asp Val Leu Ala Leu Ser Val Ser Thr
385 390 395 400

Pro Glu His Leu His Lys Ile Gly Leu Leu Asp Arg Val Thr Asn Asp
405 410 415

Thr Glu Ser Asp Ile Asn Tyr Leu Leu Lys Met Ala Leu Glu Lys Ile
420 425 430

Ala Phe Leu Pro Phe Gly Tyr Leu Val Asp Gln Trp Arg Trp Gly Val
435 440 445

Phe Ser Gly Arg Thr Pro Pro Ser Arg Tyr Asn Phe Asp Trp Trp Tyr
450 455 460

Leu Arg Thr Lys Tyr Gln Gly Ile Cys Pro Pro Val Thr Arg Asn Glu
465 470 475 480

Thr His Phe Asp Ala Gly Ala Lys Phe His Val Pro Asn Val Thr Pro
485 490 495

Tyr Ile Arg Tyr Phe Val Ser Phe Val Leu Gln Phe Gln Phe His Glu
500 505 510

Ala Leu Cys Lys Glu Ala Gly Tyr Glu Gly Pro Leu His Gln Cys Asp
515 520 525

Ile Tyr Arg Ser Thr Lys Ala Gly Ala Lys Leu Arg Lys Val Leu Gln
530 535 540

Ala Gly Ser Ser Arg Pro Trp Gln Glu Val Leu Lys Asp Met Val Gly
545 550 555 560

Leu Asp Ala Leu Asp Ala Gln Pro Leu Leu Lys Tyr Phe Gln Pro Val
565 570 575

Thr Gln Trp Leu Gln Glu Gln Asn Gln Gln Asn Gly Glu Val Leu Gly
580 585 590

Trp Pro Glu Tyr Gln Trp His Pro Pro Leu Pro Asp Asn Tyr Pro Ala
595 600 605

Gly Ala Ala
610

<210> SEQ ID NO 7
<211> LENGTH: 612
<212> TYPE: PRT
<213> ORGANISM: Homo sapiens

<400> SEQUENCE: 7

Ala Asp Pro Gly Leu Gln Pro Gly Asn Phe Ser Ala Asp Glu Ala Gly
1 5 10 15

Ala Gln Leu Phe Ala Gln Ser Tyr Asn Ser Ser Ala Glu Gln Val Leu
20 25 30

Phe Gln Ser Val Ala Ala Ser Trp Ala His Asp Thr Asn Ile Thr Ala
35 40 45

Glu Asn Ala Arg Arg Gln Glu Glu Ala Ala Leu Leu Ser Gln Glu Phe
50 55 60

-continued

```
Ala Glu Ala Trp Gly Gln Lys Ala Lys Glu Leu Tyr Glu Pro Ile Trp
65                  70                  75                  80

Gln Asn Phe Thr Asp Pro Gln Leu Arg Arg Ile Ile Gly Ala Val Arg
                85                  90                  95

Thr Leu Gly Ser Ala Asn Leu Pro Leu Ala Lys Arg Gln Gln Tyr Asn
            100                 105                 110

Ala Leu Leu Ser Asn Met Ser Arg Ile Tyr Ser Thr Ala Lys Val Cys
        115                 120                 125

Leu Pro Asn Lys Thr Ala Thr Cys Trp Ser Leu Asp Pro Asp Leu Thr
    130                 135                 140

Asn Ile Leu Ala Ser Ser Arg Ser Tyr Ala Met Leu Leu Phe Ala Trp
145                 150                 155                 160

Glu Gly Trp His Asn Ala Ala Gly Ile Pro Leu Lys Pro Leu Tyr Glu
                165                 170                 175

Asp Phe Thr Ala Leu Ser Asn Glu Ala Tyr Lys Gln Asp Gly Phe Thr
            180                 185                 190

Asp Thr Gly Ala Tyr Trp Arg Ser Trp Tyr Asn Ser Pro Thr Phe Glu
        195                 200                 205

Asp Asp Leu Glu His Leu Tyr Gln Gln Leu Glu Pro Leu Tyr Leu Asn
    210                 215                 220

Leu His Ala Phe Val Arg Arg Ala Leu His Arg Arg Tyr Gly Asp Arg
225                 230                 235                 240

Tyr Ile Asn Leu Arg Gly Pro Ile Pro Ala His Leu Leu Gly Asp Met
                245                 250                 255

Trp Ala Gln Ser Trp Glu Asn Ile Tyr Asp Met Val Val Pro Phe Pro
            260                 265                 270

Asp Lys Pro Asn Leu Asp Val Thr Ser Thr Met Leu Gln Gln Gly Trp
        275                 280                 285

Asn Ala Thr His Met Phe Arg Val Ala Glu Glu Phe Phe Thr Ser Leu
    290                 295                 300

Glu Leu Ser Pro Met Pro Pro Glu Phe Trp Glu Gly Ser Met Leu Glu
305                 310                 315                 320

Lys Pro Ala Asp Gly Arg Glu Val Val Cys His Ala Ser Ala Trp Asp
                325                 330                 335

Phe Tyr Asn Arg Lys Asp Phe Arg Ile Lys Gln Cys Thr Arg Val Thr
            340                 345                 350

Met Asp Gln Leu Ser Thr Val His His Glu Met Gly His Ile Gln Tyr
        355                 360                 365

Tyr Leu Gln Tyr Lys Asp Leu Pro Val Ser Leu Arg Arg Gly Ala Asn
    370                 375                 380

Pro Gly Phe His Glu Ala Ile Gly Asp Val Leu Ala Leu Ser Val Ser
385                 390                 395                 400

Thr Pro Glu His Leu His Lys Ile Gly Leu Leu Asp Arg Val Thr Asn
                405                 410                 415

Asp Thr Glu Ser Asp Ile Asn Tyr Leu Leu Lys Met Ala Leu Glu Lys
            420                 425                 430

Ile Ala Phe Leu Pro Phe Gly Tyr Leu Val Asp Gln Trp Arg Trp Gly
        435                 440                 445

Val Phe Ser Gly Arg Thr Pro Pro Ser Arg Tyr Asn Phe Asp Trp Trp
    450                 455                 460

Tyr Leu Arg Thr Lys Tyr Gln Gly Ile Cys Pro Pro Val Thr Arg Asn
465                 470                 475                 480

Glu Thr His Phe Asp Ala Gly Ala Lys Phe His Val Pro Asn Val Thr
```

```
                485                 490                 495

Pro Tyr Ile Arg Tyr Phe Val Ser Phe Val Leu Gln Phe Gln Phe His
            500                 505                 510

Glu Ala Leu Cys Lys Glu Ala Gly Tyr Glu Gly Pro Leu His Gln Cys
        515                 520                 525

Asp Ile Tyr Arg Ser Thr Lys Ala Gly Ala Lys Leu Arg Lys Val Leu
    530                 535                 540

Gln Ala Gly Ser Ser Arg Pro Trp Gln Glu Val Leu Lys Asp Met Val
545                 550                 555                 560

Gly Leu Asp Ala Leu Asp Ala Gln Pro Leu Leu Lys Tyr Phe Gln Pro
                565                 570                 575

Val Thr Gln Trp Leu Gln Glu Gln Asn Gln Gln Asn Gly Glu Val Leu
            580                 585                 590

Gly Trp Pro Glu Tyr Gln Trp His Pro Pro Leu Pro Asp Asn Tyr Pro
        595                 600                 605

Ala Gly Ala Ala
    610


<210> SEQ ID NO 8
<211> LENGTH: 519
<212> TYPE: PRT
<213> ORGANISM: Homo sapiens

<400> SEQUENCE: 8

Ala Pro Gly Leu Gln Pro Gly Asn Phe Ser Ala Asp Glu Ala Gly Ala
1               5                   10                  15

Gln Leu Phe Ala Gln Ser Tyr Asn Ser Ser Ala Glu Gln Val Leu Phe
            20                  25                  30

Gln Ser Val Ala Ala Ser Trp Ala His Asp Thr Asn Ile Thr Ala Glu
        35                  40                  45

Asn Ala Arg Arg Gln Glu Glu Ala Ala Leu Leu Ser Gln Glu Phe Ala
    50                  55                  60

Glu Ala Trp Gly Gln Lys Ala Lys Glu Leu Tyr Glu Pro Ile Trp Gln
65                  70                  75                  80

Asn Phe Thr Asp Pro Gln Leu Arg Arg Ile Ile Gly Ala Val Arg Thr
                85                  90                  95

Leu Gly Ser Ala Asn Leu Pro Leu Ala Lys Arg Gln Gln Tyr Asn Ala
            100                 105                 110

Leu Leu Ser Asn Met Ser Arg Ile Tyr Ser Thr Ala Lys Val Cys Leu
        115                 120                 125

Pro Asn Lys Thr Ala Thr Cys Trp Ser Leu Asp Pro Asp Leu Thr Asn
    130                 135                 140

Ile Leu Ala Ser Ser Arg Ser Tyr Ala Met Leu Leu Phe Ala Trp Glu
145                 150                 155                 160

Gly Trp His Asn Ala Ala Gly Ile Pro Leu Lys Pro Leu Tyr Glu Asp
                165                 170                 175

Phe Thr Ala Leu Ser Asn Glu Ala Tyr Lys Gln Asp Gly Phe Thr Asp
            180                 185                 190

Thr Gly Ala Tyr Trp Arg Ser Trp Tyr Asn Ser Pro Thr Phe Glu Asp
        195                 200                 205

Asp Leu Glu His Leu Tyr Gln Gln Leu Glu Pro Leu Tyr Leu Asn Leu
    210                 215                 220

His Ala Phe Val Arg Arg Ala Leu His Arg Arg Tyr Gly Asp Arg Tyr
225                 230                 235                 240
```

-continued

```
Ile Asn Leu Arg Gly Pro Ile Pro Ala His Leu Leu Gly Asp Met Trp
                245                 250                 255

Ala Gln Ser Trp Glu Asn Ile Tyr Asp Met Val Val Pro Phe Pro Asp
            260                 265                 270

Lys Pro Asn Leu Asp Val Thr Ser Thr Met Leu Gln Gln Gly Trp Asn
        275                 280                 285

Ala Thr His Met Phe Arg Val Ala Glu Glu Phe Phe Thr Ser Leu Glu
    290                 295                 300

Leu Ser Pro Met Pro Pro Glu Phe Trp Glu Gly Ser Met Leu Glu Lys
305                 310                 315                 320

Pro Ala Asp Gly Arg Glu Val Val Cys His Ala Ser Ala Trp Asp Phe
                325                 330                 335

Tyr Asn Arg Lys Asp Phe Arg Ile Lys Gln Cys Thr Arg Val Thr Met
            340                 345                 350

Asp Gln Leu Ser Thr Val His His Glu Met Gly His Ile Gln Tyr Tyr
        355                 360                 365

Leu Gln Tyr Lys Asp Leu Pro Val Ser Leu Arg Arg Gly Ala Asn Pro
    370                 375                 380

Gly Phe His Glu Ala Ile Gly Asp Val Leu Ala Leu Ser Val Ser Thr
385                 390                 395                 400

Pro Glu His Leu His Lys Ile Gly Leu Leu Asp Arg Val Thr Asn Asp
                405                 410                 415

Thr Glu Ser Asp Ile Asn Tyr Leu Leu Lys Met Ala Leu Glu Lys Ile
            420                 425                 430

Ala Phe Leu Pro Phe Gly Tyr Leu Val Asp Gln Trp Arg Trp Gly Val
        435                 440                 445

Phe Ser Gly Arg Thr Pro Pro Ser Arg Tyr Asn Phe Asp Trp Trp Tyr
    450                 455                 460

Leu Arg Thr Lys Tyr Gln Gly Ile Cys Pro Pro Val Thr Arg Asn Glu
465                 470                 475                 480

Thr His Phe Asp Ala Gly Ala Lys Phe His Val Pro Asn Val Thr Pro
                485                 490                 495

Tyr Ile Arg Tyr Phe Val Ser Phe Val Leu Gln Phe Gln Phe His Glu
            500                 505                 510

Ala Leu Cys Lys Glu Ala Gly
        515
```